US 11,149,080 B2

(12) United States Patent
Chandran et al.

(10) Patent No.: US 11,149,080 B2
(45) Date of Patent: Oct. 19, 2021

(54) METHODS OF TREATING FILOVIRUS INFECTIONS UTILIZING BISPECIFIC ANTIBODIES AND FUSION PROTEINS THAT BIND EBOV AND NPC1

(71) Applicant: ALBERT EINSTEIN COLLEGE OF MEDICINE, Bronx, NY (US)

(72) Inventors: Kartik Chandran, Brooklyn, NY (US); Anna Z. Wec, Bronx, NY (US); Elisabeth K. Nyakatura, New York, NY (US); Jonathan R. Lai, Dobbs Ferry, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 16/445,497

(22) Filed: Jun. 19, 2019

(65) Prior Publication Data

US 2020/0199202 A1    Jun. 25, 2020

Related U.S. Application Data

(63) Continuation of application No. 15/571,512, filed as application No. PCT/US2016/030652 on May 4, 2016, now Pat. No. 10,377,815.

(60) Provisional application No. 62/157,104, filed on May 5, 2015.

(51) Int. Cl.
| | |
|---|---|
| *C07K 16/28* | (2006.01) |
| *C07K 16/10* | (2006.01) |
| *A61K 39/00* | (2006.01) |
| *A61K 39/395* | (2006.01) |
| *C07K 16/46* | (2006.01) |
| *A61P 31/14* | (2006.01) |

(52) U.S. Cl.
CPC .............. *C07K 16/10* (2013.01); *A61K 39/00* (2013.01); *A61K 39/395* (2013.01); *A61P 31/14* (2018.01); *C07K 16/28* (2013.01); *C07K 16/468* (2013.01); *C07K 2317/31* (2013.01); *C07K 2317/56* (2013.01); *C07K 2317/622* (2013.01); *C07K 2317/76* (2013.01); *C07K 2317/92* (2013.01); *C07K 2319/00* (2013.01); *C07K 2319/01* (2013.01); *C12N 2760/14111* (2013.01)

(58) Field of Classification Search
CPC ................. C07K 16/28; C07K 16/10
See application file for complete search history.

(56) References Cited

U.S. PATENT DOCUMENTS

| | | |
|---|---|---|
| 10,377,815 B2 | 8/2019 | Chandran et al. |
| 2003/0092038 A1 | 5/2003 | Carstea et al. |
| 2010/0009461 A1 | 1/2010 | Garcia-Calvo |
| 2014/0329834 A1 | 11/2014 | Cunningham et al. |
| 2020/0199202 A1 | 6/2020 | Chandran, III et al. |

OTHER PUBLICATIONS

Messaoudi, I., et al., Nov. 2015, Filovirus pathogenesis and immune evasion: insights from Ebola virus and Marburg virus, Nat. Rev. Microbiol. 13:663-676.*
Gonzalez-Gonzalez, E., et al., 2017, Anti-Ebola therapies based on monoclonal antibodies: current state and challenges ahead, Crit. Rev. Biotech. 37(1):53-68 (published online Dec. 1, 2015).*
Kugelman, J. R., et al., Sep. 2015, Emergence of Ebola virus escape variants in infected nonhuman primates treated with the MB-003 antibody cocktail, Cell Reports 12:2111-2120.*
Moekotte, A. L., et al., Oct. 2016, Monoclonal antibodies for the treatment of Ebola virus disease, Exp. Opin. Invest. Drugs 25(11):1325-1335.*
PCT International Search Report and Written Opinion dated Sep. 9, 2016 for PCT International Patent Application No. PCT/US2016/030652, 9 pages.
Miller E H et al., "Ebola virus entry requires the host-programmed recognition of an intracellular receptor," The EMBO Journal, (2012), vol. 31, No. 8, 1947-1960.
Bornholdt Z A et al., "Host-Primed Ebola Virus GP Exposes a Hydrophobic NPC1 Receptor-Binding Pocket, Revealing a Target for Broadly Neutralizing Antibodies," mBio, Jan./Feb. 2016, vol. 7, Issue 1, e02154-15. 1-11.
Kugelman, J. R., et al., Sep. 2015, Emergence of Ebola virus escape variants in infected nonhuman primates treated with the MB-003 cocktail, Cell Reports 12:2111-2120.
Moekotte, A. L., et al., 2016, Monoclonal antibodies for the treatment of Ebola virus disease, Exp. Opin. Invest. Drugs, 25(11):1325-1335.
Gonzalez-Gonzalez, E., et al., Dec. 2015, Anti-Ebola therapies based on monoclonal antibodies: current state and challenges ahead, Crit. Rev. Biotech. 37(1):53-68.

* cited by examiner

*Primary Examiner* — Jeffrey S Parkin
(74) *Attorney, Agent, or Firm* — Foley Hoag LLP

(57) ABSTRACT

Disclosed are bispecific antibodies and bispecific fusion constructs that bind to Niemann-Pick C1 (NPC1) receptor for treating or preventing filovirus infections, pharmaceutical compositions comprising the bispecific antibodies, and therapeutic methods using the bispecific antibodies.

18 Claims, 24 Drawing Sheets

Specification includes a Sequence Listing.

| Antibody | Antigen | pH | $k_a(M^{-1}S^{-1})^a$ | $k_d(S^{-1})^b$ | $K_D(nM)^c$ |
|---|---|---|---|---|---|
| 548 | Human NPC1-C | 7.5 | $(1.870\pm0.004)\times10^5$ | $<1.0\times10^{-7}$ | $<0.001$ |
| 548 | Human NPC1-C | 5.5 | $(2.020\pm0.005)\times10^5$ | $<1.0\times10^{-7}$ | $<0.001$ |
| 548 | NHP NPC1-C | 5.5 | $(2.24\pm0.01)\times10^5$ | $<1.0\times10^{-7}$ | $<0.001$ |
| 548 | Mouse NPC1-C | 5.5 | $NA^d$ | NA | NA |

| Antibody | Antigen | pH | $k_a(M^{-1}S^{-1})^a$ | $k_d(S^{-1})^b$ | $K_D(nM)^c$ |
|---|---|---|---|---|---|
| FVM09 | EBOV GP | 7.5 | $(1.200\pm0.004)\times10^4$ | $(5.5\pm0.1)\times10^{-5}$ | $4.50\pm0.09$ |
| 548 | Human NPC1-C | 7.5 | $(1.870\pm0.004)\times10^5$ | $<1.0\times10^{-7}$ | $<0.001$ |
| FVM09~548 | EBOV GP | 7.5 | $(1.220\pm0.004)\times10^4$ | $(2.2\pm0.2)\times10^{-5}$ | $1.79\pm0.07$ |
| FVM09~548 | Mouse NPC1-C | 7.5 | $(8.58\pm0.08)\times10^4$ | $<1.0\times10^{-7}$ | $<0.001$ |

Binding competition:
*C. guereza* NPC1-C vs. 548 | GP$_{CL}$

FIG. 13B

```
                              485                              514
Homo sapiens                  LNYFQNSHSV LDHKKGDDFF VYADYHTHFL
Macaca mulatta                LNYFQNSHSV LDHKKGDDFF VYADYHTHFL
Colobus guereza               LNYFQNSHSV LDHKKGDDFF VYADYHTHFL
Macaca fascicularis           LNYFQNSHSV LDHKKGDDFF VYADYHTHFL
                                         ─────────────────────
                                            548 binding region
```

FIG. 13C

METHODS OF TREATING FILOVIRUS INFECTIONS UTILIZING BISPECIFIC ANTIBODIES AND FUSION PROTEINS THAT BIND EBOV AND NPC1

CROSS-REFERENCE TO RELATED APPLICATIONS

This application is a continuation of U.S. patent application Ser. No. 15/571,512, filed Nov. 3, 2017, which is a U.S. national stage entry under 35 U.S.C. § 371 of PCT International Patent Application No. PCT/US2016/030652, filed May 4, 2016, which claims the benefit of U.S. Provisional Patent Application No. 62/157,104, filed May 5, 2015, the contents of each of which are incorporated herein by reference into the subject application.

STATEMENT OF GOVERNMENT SUPPORT

This invention was made with government support under grant numbers AI101436, AI109762 and AI090249 awarded by the National Institutes of Health. The government has certain rights in the invention.

BACKGROUND OF THE INVENTION

Throughout this application various publications are referred to in parentheses. Full citations for these references may be found at the end of the specification. The disclosures of these publications are hereby incorporated by reference in their entirety into the subject application to more fully describe the art to which the subject invention pertains.

Multiple members of the family Filoviridae of enveloped negative-strand RNA viruses (filoviruses) cause a highly lethal hemorrhagic fever for which no approved treatments are available. While Ebola virus (EBOV) is responsible for the ongoing unprecedented epidemic in West Africa, the antigenically-distinct Sudan virus (SUDV), Bundibugyo virus (BDBV), Marburg virus (MARV), and Ravn virus (RAVV) have also caused outbreaks with high case fatality rates (30-90%). Moreover, novel filoviruses with zoonotic potential likely await discovery in the filovirus-endemic zone of equatorial Africa and elsewhere. As a case in point, the founding member of a distinct Filovirus Glade, Lloviu virus (LLOV), was recently isolated in southern Spain and Portugal, where it is suspected to have caused mass die-offs of insectivorous cave bats (Negredo, *PLoS Pathog,* 2011).

The current outbreak in West Africa has seen ZMapp (Mapp Biopharmaceuticals), a mixture of three humanized mouse monoclonal antibodies (mAbs) against the EBOV spike glycoprotein (GP), emerge as a promising treatment for Ebola virus disease. More generally, it has provided a powerful proof-of-concept for mAb-based prophylactics and therapeutics against filoviruses. However, a major limitation of ZMapp and other planned mAb cocktails is their narrow spectrum of action (against EBOV only), dictated by the high antigenic diversity of filovirus GP proteins. Because the development, stockpiling, and deployment of separate mAb cocktails against each virulent filovirus is impractical, broad-spectrum mAb-based treatments that target multiple filoviruses are highly desirable.

The endo/lysosomal cholesterol transporter Niemann-Pick C1 (NPC1) is a universal intracellular receptor for entry and infection by filoviruses, and is required for in vivo pathogenesis by both EBOV and MARV (and almost certainly by BDBV, SUDV, and RAVV as well) (Carette, *Nature,* 2011; Ng, *Virology,* 2014). NPC1 protein has a cytoplasmic C-terminus, 13 transmembrane domains, and 3 large loops in the lumen of the endosome (Davies et al 2000). One complication in targeting NPC1 with monoclonal antibodies (mAbs) is its exclusive localization to late endosomal compartments, where it is protected from extracellular antibodies.

The present invention uses bispecific antibodies (bsAbs) with potent anti-filovirus activity to address the need for methods for treating subjects infected with filoviruses or who are at risk for infection with filoviruses.

SUMMARY OF THE INVENTION

The invention provides methods of treating or preventing or reducing or inhibiting or reducing the risk or incidence of a filovirus infection in a subject comprising administering to the subject a bispecific antibody or a bispecific fusion construct that binds to Niemann-Pick C1 (NPC1) receptor in an amount effective to treat or prevent or reduce or inhibit or reduce the risk or incidence of a filovirus infection in a subject.

The invention further provides bispecific antibodies and bispecific fusion constructs that bind to Niemann-Pick C1 (NPC1) receptor for treating or preventing or reducing or inhibiting or reducing the risk or incidence of a filovirus infection in a subject.

BRIEF DESCRIPTION OF THE DRAWINGS

FIG. 2A-2D. A illustrates the X-ray crystal structure of a cleaved EBOV GP (GPCL) trimer bound to three copies of a soluble human NPC1 domain C protein. In B, side bottom views of NPC1 domain C are shown, with residues contacting GPCL (left panel) and mAb 548 (right panel) highlighted. C-D demonstrate the kinetics of binding of 548 to human NPC1 domain C by biolayer interferometry (BLI). D shows BLI-derived kinetic binding constants for the interaction of 548 with human and non-human primate (NHP; *Colobus* guereza) NPC1 domain C. 548 recognizes these proteins with picomolar affinity, at both neutral and acid pH.

Figures 9B, 9C:
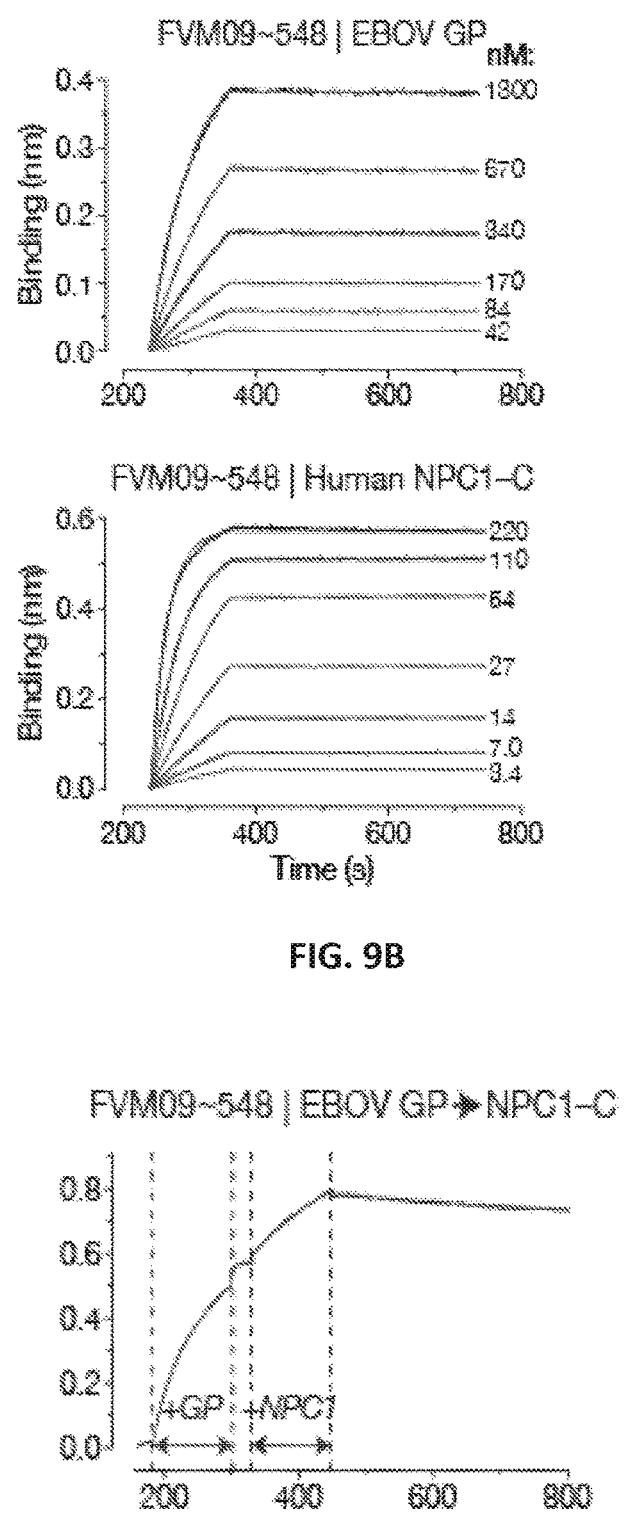

FIG. 9A-9D. A illustrates a bispecific antibody strategy for delivery of an NPC1-binding antibody to NPC1-positive endosomal/lysosomal compartments. In this strategy, the heavy and light chains of an NPC1-binding antibody like 548 are genetically fused to the variable VH and VL domains of a delivery antibody like FVM09, to generate a dual-variable domain Ig (DVD-Ig™). FVM09 broadly recognizes ebolavirus GP in extracellular viral particles or on the cell surface. However, the delivery antibody could also target a cell-surface marker, instead of viral GP. In B, the binding of the FVM09~548 DVD-Ig to each of its antigens (ebolavirus GP, human NPC1-C) is measured by BLI. In C, two-phase BLI binding curves show that FVM09~548 can simultaneously bind to both of its antigens. D shows BLI-derived kinetic binding constants for the interaction of the FVM09~548 DVD-Ig with each of its antigens, and compares these constants to those obtained with the respective parent IgGs.

Figure 11C:
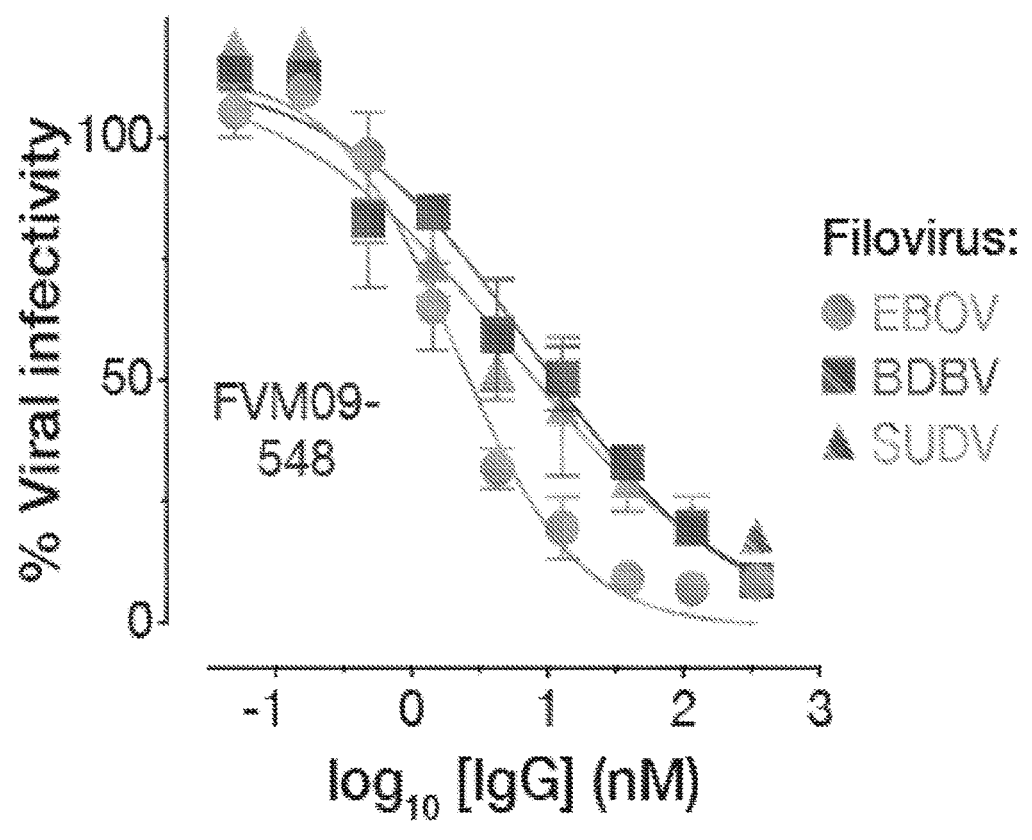

FIG. 11A-11C measures the capacity of the FVM09~548 bispecific antibody to neutralize ebolavirus GP-dependent entry and infection in human cells. In A, vesicular stomatitis viruses bearing EBOV GP (VSV-EBOV GP) were incubated with increasing concentrations of FVM09~548, its parent IgGs FVM09, 548, or an equimolar mixture of the parent IgGs (FVM09+548), and then exposed to cells. Only FVM09~548 showed potent, dose-dependent neutralization of VSV-EBOV GP infection. B shows that FVM09~548 can broadly neutralize infection mediated by multiple ebolavirus GPs. C shows that authentic EBOV, BDBV, and SUM can be potently neutralized by FVM09~548.

Figures 12A, 12B:
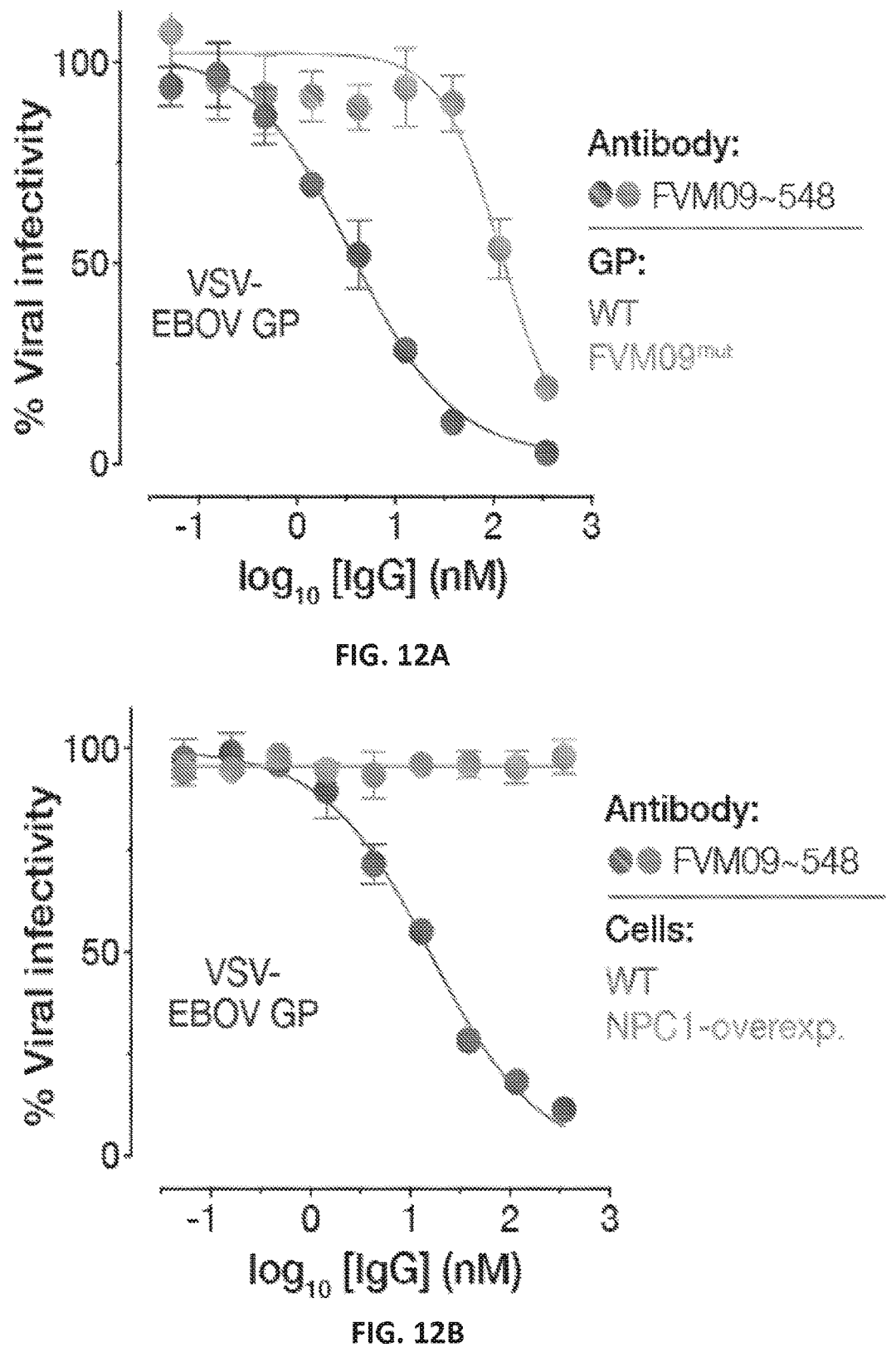

FIG. 12A-12C examines the mechanism of action of the FVM09~548 bispecific antibody. In A, wild-type (WT) VSV-EBOV GP particles, or mutant particles containing two point mutations (E288D/W292R) in the FVM09 epitope ((FVM09mut) were incubated with increasing concentrations of the FVM09~549 antibody, and then exposed to cells. Loss of FVM09-GP binding is associated with a 99% reduction in the potency of antiviral neutralization, providing evidence that engagement of GP in extracellular virus particles by FVM09~548 is necessary for its neutralizing activity. In B, VSV-EBOV GP particles were incubated with FVM09~548 and then exposed to isogenic cell lines expressing physiological levels of human NPC1 (WT), or expressing high levels of human NPC1 (NPC1-overexp). The neutralization potency of FVM09~548 was abolished by NPC1 over-expression, likely because of the titration of available antibody by excess NPC1. This experiment provides evidence that engagement of NPC1 domain C by 548 in endosomes is required for the neutralizing activity of FVM09~548. In C, the delivery of FVM09~548 to NPC1-containing endosomes was directly examined. VSV-EBOV OP particles labeled with the fluorescent protein mNeongreen (UNG) were incubated with antibodies labeled with the fluorophore pHrodo-Red™, which only fluoresces at acid pH (left panel). The virus-antibody mixture was exposed to cells at 37° C. for 30 min, after which time, cells were examined for both virus- and antibody-associated fluorescence by two-color flow cytometry. The flow cytometric analysis is shown in the right panel. Cells were gated into virus-negative and virus-positive populations based on mNeongreen fluorescence, and each subpopulation was father examined for pHrodo-Red™ fluorescence. Strong pHrodo-Red™ fluorescence was seen with FVM09 in the virus-positive sample only, indicating that binding of this antibody to GP on extracellular virus particles affords its delivery to acidic endosomes. Little or no pHrodo-Red™ fluorescence was observed with 548 in the absence or presence of virus, indicating that this antibody cannot access endosomal compartments on its. By contrast FVM09~548 gave a strong pHrodo-Red™ signal in virus-positive cells. Therefore, combining FVM09 and 548 into a single bispecific antibody promotes efficient delivery of 548 to endosomes through the action of FVM09, FIG. 13A-13C. The capacity of the human NPC1 domain C binding antibody 548 to bind to a non-human primate (*Colobus* guereza) NPC1 domain C protein and block EBOV GP-NPC1 binding is shown. In A, BLI is employed to detect and measure 548 binding to *C. guereza* NPC domain C at the acidic pH of late endosomes. B shows the capacity of 548 to block GP-*C. guereza* NPC1 domain C binding in an ELISA. A soluble, flag-tagged form of *C. guereza* NPC1 domain C was pre-incubated with the indicated concentrations of 548, and the protein-mAb mixtures were then added to plates coated with vesicular stomatitis virus (VSV) particles bearing EBOV GP. Bound domain C was detected with an anti-flag antibody. Because the sequences of *C. guereza* NPC1 that contact GP are identical to those of NPC1 proteins from rhesus macaques (*Macaca mulatto*) and cynomolgus macaques (*Macaca fascicularis*) (FIG. 13C), 548 can be evaluated for antiviral protection in these two established non-human primate (NHP) models of filovirus challenge. In C, sequences corresponding to NPC1 residues 485-514 (human NPC1 numbering) are shown. The 548 epitope is indicated—it is identical in humans and the three indicated NHP species. *Homo sapiens*—SEQ ID NO:24, *Macaca mulatto* SEQ ID NO:25, *Colobus guereza*—SEQ ID NO:26, *Macaca fascicularis*—SEQ ID NO:27.

DETAILED DESCRIPTION OF THE INVENTION

Figure 1A:
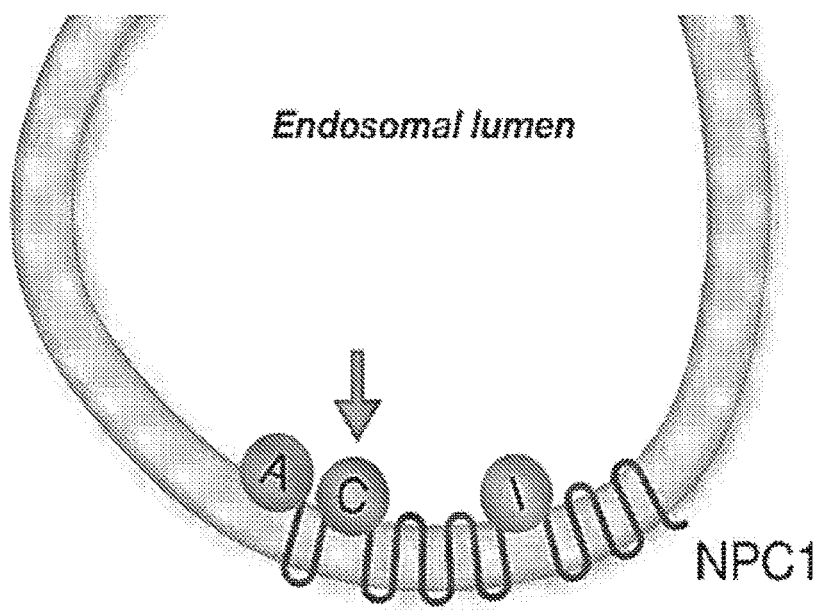
FIG. 1A. NPC1 is required for Ebola virus infection. Niemann-Pick C1 (NPC1), a ubiquitous multi-pass membrane protein localized to late endosomes is required for cytoplasmic entry and infection by all filoviruses. The filovirus spike glycoprotein, GP, must engage NPC1's second luminal domain (domain C; arrow) to drive viral membrane fusion and cytoplasmic escape.

The present invention provides a method for treating or preventing or reducing or inhibiting or reducing the risk or incidence of a filovirus infection in a subject comprising administering to the subject a bispecific antibody or a bispecific fusion construct that binds to Niemann-Pick C1 (NPC1) receptor in an amount effective to treat or prevent or reduce or inhibit or reduce the risk or incidence of a filovirus infection in a subject.

The invention also provides a bispecific antibody or a bispecific fusion construct that hinds to Niemann-Pick C1 (NPC1) receptor for treating or preventing or reducing or inhibiting or reducing the risk or incidence of a filovirus infection in a subject.

The bispecific antibody or bispecific fusion construct can combine both antiviral and anti-NPC1 specificities in the same molecule. For example, the bispecific antibody or bispecific fusion construct can bind both to NPC1 and to filovirus glycoprotein (GP).

The bispecific antibody can be generated by fusing a NPC1-specific sequence to a single-chain variable fragment (scFv) sequence derived from EBOV GP-specific monoclonal antibody KZ52, where the fusion can be to a N- or C-terminus of an IgG heavy chain or light chain.

The bispecific antibody or bispecific fusion construct can combine an anti-NPC1 specificity with an endosomal targeting functionality. This can include an antibody specific for a cellular molecule that affords endosomal delivery (e.g., NPC2) or a peptide or protein that would do the same (not necessarily just an antibody). Thus, the bispecific antibody or bispecific fusion construct can bind both to NPC1 and to Niemann-Pick C2 (NPC2).

The bispecific antibody or bispecific fusion construct can be generated by fusing heavy and light chains of a NPC1-specific sequence to variable VH and VL domains of a delivery antibody to generate a dual-variable domain Ig. The dual variable domain-Ig (DVD-Ig) bispecific antibody format was developed by AbbVie (Wu et al., 2007). The delivery antibody can target, for example, a filovirus glycoprotein (GP) or a cell-surface marker. The delivery antibody can be, for example, FVM09 (Keck et al. 2015). FVM09 broadly recognizes ebolavirus GP in extracellular viral particles or on the cell surface.

The anti-NPC1 amino acid sequence of a variable region of a light chain of the bispecific antibody or bispecific fusion construct can comprise the amino acid sequence set forth in SEQ ID NO:3, SEQ ID NO:5 or SEQ ID NO:7. The anti-NPC1 amino acid sequence of a variable region of a heavy chain of the bispecific, antibody or bispecific fusion construct can comprise the amino acid sequence set forth in SEQ ID NO:4, SEQ ID NO:6 or SEQ ID NO:8. The anti-NPC1 amino acid sequence of a variable region of a light chain can comprise the amino acid sequence set forth in SEQ ID NO:3 and a variable region of a heavy chain can comprise the amino acid sequence set forth in SEQ ID NO:4. The anti-NPC1 amino acid sequence of a variable region of a light chain can comprise the amino acid sequence set forth in SEQ ID NO:5 and a variable region of a heavy chain can comprise the amino acid sequence set forth in SEQ ID NO:6. The anti-NPC1 amino acid sequence of a variable region of a light chain can comprise the amino acid sequence set forth in SEQ ID NO:7 and a variable region of a heavy chain can comprise the amino acid sequence set forth in SEQ ID NO:8.

The bispecific antibody can comprise the amino acid sequence set forth in any one of SEQ ID NOs:9-20. The bispecific fusion construct can comprise the amino acid sequence set forth in SEQ ID NO:21 or SEQ ID NO:22.

In different uses, the subject can be infected with a filovirus. Alternatively, the subject can be at risk for infection with a filovirus. Subjects who are at risk for infection with filoviruses include subjects who have been exposed to filovirus or are at risk of exposure to filovirus. In addition to the natural occurrence of filoviruses, there is the potential for exposure to these pathogens if they are used as agents of bioterrorism or biological warfare. For example, the subject can be a family member or healthcare worker in an area of an outbreak of a filovirus infection. The subject can be a medical personnel, first responder or military personnel potentially exposed or exposed to a filovirus as the result of bioterrorism or biological warfare. The subject can be a biosafety level 3/4 laboratory personnel or animal worker potentially exposed or exposed to a filovirus.

The family Filoviridae is a family of viruses including genera Ebolavirus and Marburgvirus. The Ebola virus species can be *Zaire ebolavirus* or *Sudan ebolavirus*. Additional examples of filovirus include a Bundibugyo virus, a Sudan virus, a Ravn virus and a Lloviu virus.

The subject can be a mammal, such as, for example, livestock, a bat, a primate or a human.

To treat a subject with a filovirus infection means to reduce or stop the spread of filovirus in the subject, or to eliminate the filovirus from the subject, or to reduce or eliminate a sign or symptom of filovirus infection in the subject. Filovirus infection is characterized by hemorrhagic fever, including abnormalities in blood coagulation. As used herein, "preventing" a filovirus infection means reducing the development of, or reducing the extent of, one or more symptoms of the condition, as compared to the development or extent the condition takes in the absence of preventative treatment. In an embodiment, "preventing" as used herein does not mean an absolute prevention, but a lessened extent of the condition brought about prophylactically, or to reduce the risk or incidence of a filovirus infection.

Human NPC1 receptor protein has the amino acid sequence (SEQ ID NO:1) (NCBI Reference Sequence: NM_000271.4):

```
MTARGLALGL LLLLLCPAQV FSQSCVWYGE CGIAYGDKRY NCEYSGPPKP KPKDGYDLVQ      60
ELCPGFFFGN VSLCCDVRQL QTLKDNLQLP LQFLSRCPSC FYNLLNLFCE LTCSPRQSQF     120
LNVTATEDYV DPVTNQTKTN VKELQYYVGQ SFANAMYNAC RDVEAPSSND VDEVTAPCSC     180
ADACNATNWI EYMFNKDNGQ APFTITPVFS DFPVHGMEPM NNATKGCDES VDEVTAPCSC     240
QDCSIVCGPK PQPPPPPAPW TILGLDAMYV IMWITYMAFL LVFFGAFFAV WCYRKRYFVS     300
EYTPIDSNIA FSVNASDKGE ASCCDPVSAA FEGCLRRLFT RWGSFCVRNP GCVIFFSLVF     360
ITACSSGLVF VRVTTNPVDL WSAPSSQARL EKEYFDQHFG PFFRTEQLII RAPLTDKHIY     420
QPYPSGADVP FGPPLDIQIL HQVLDLQIAI ENITASYDNE TVTLQDICLA PLSPYNTNCT     480
ILSVLNYFQN SHSVLDHKKG DDFFVYADYH THFLYCVRAP ASLNDTSLLH DPCLGTFGGP     540
VFPWLVLGGY DDQNYNNATA LVITFPVNNY YNDTEKLQRA QAWEKEFINE VKNYKNPNLT     600
ISFTAERSIE DELNRESDSD VFTVVISYAI MFLYISLALG HMKSCRRLLV DSKVSLGIAG     660
ILIVLSSVAC SLGVFSYIGL PLTLIVIEVI PFLVLAVGVD NIFILVQAYQ RDERLQGETL     720
DQQLGRVLGE VAPSMFLSSF SETVAFFLGA LSVMPAVHTF SLFAGLAVFI DFLLQITCFV     780
SLLGLDIKRQ EKNRLDIFCC VRGAEDGTSV QASESCLFRF FKNSYSPLLL KDWMRPIVIA     840
IFVGVLSFSI AVLNKVDIGL SQSLSMPDDS YMVDYFKSIS QYLHAGPPVY FVLEEGHDYT     900
SSKGQNMVCG GMGCNNDSLV QQIFNAAQLD NYTRIGFAPS SWIDDYFDWV KPQSSCCRVD     960
NITDQFCNAS VVDPACVRCR PLTPEGKQRP QGGDFMRFLP MFLSDNPNPK CGKGGHAAYS    1020
SAVNILLGHG TRVGATYFMT YHTVLQTSAD FIDALKKARL IASNVTETMG INGSAYRVFP    1080
YSVFYVFYEQ YLTIIDDTIF NLGVSLGAIF LVTMVLLGCE LWSAVIMCAT IAMVLVNMFG    1140
NMWLWGISLN AVSLVNLVMS CGISVEFCSH ITRAFTVSMN GSRVERAEEA LAHMGSSVFS    1200
GITLTKFGGI VVLAFAKSQI FQIFYFRMYL AMVLLGATHG LIFLPVLLSY IGPSVNKAKS    1260
CATEERYKGT ERERLLNG                                                  1278
```

Nucleic acid (mRNA) encoding human NPC1 receptor protein has the nucleotide sequence (SEQ ID NO:2) (NCBI Reference Sequence: NM_000271.4):

```
  1 gaagggcaac acggggacct tgaagcgggg tcgcggcggc gccccagccc gggccaggga
 61 gtcccggcag cggcacctcc cagaaagggc ggagccgacg acgccttctt ccttcctgac
121 cggcgcgcgc agcctgctgc cgcggtcagc gcctgctcct gctcctccgc tcctcctgcg
181 cggggtgctg aaacagcccg gggaagtaga gccgcctccg gggagcccaa ccagccgaac
241 gccgccggcg tcagcagcct tgcgcggcca cagcatgacc gctcgcggcc tggcccttgg
301 cctcctcctg ctgctactgt gtccagcgca ggtgttttca cagtcctgtg tttggtatgg
361 agagtgtgga attgcatatg gggacaagag gtacaattgc gaatattctg gcccaccaaa
421 accattgcca aaggatggat atgacttagt gcaggaactc tgtccaggat tcttctttgg
481 caatgtcagt ctctgttgtg atgttcggca gcttcagaca ctaaaagaca acctgcagct
541 gcctctacag tttctgtcca gatgtccatc ctgtttttat aacctactga acctgttttg
601 tgagctgaca tgtagccctc gacagagtca gttttttgaat gttacagcta ctgaagatta
661 tgttgatcct gttacaaacc agacgaaaac aaatgtgaaa gagttacaat actacgtcgg
721 acagagttt gccaatgcaa tgtacaatgc tgccgggat gtggaggccc cctcaagtaa
781 tgacaaggcc ctgggactcc tgtgtgggaa ggacgctgac gcctgtaatg ccaccaactg
841 gattgaatac atgttcaata aggacaatgg acaggcacct tttaccatca ctcctgtgtt
```

-continued

```
 901 ttcagatttt ccagtccatg ggatggagcc catgaacaat gccaccaaag gctgtgacga
 961 gtctgtggat gaggtcacag caccatgtag ctgccaagac tgctctattg tctgtggccc
1021 caagccccag cccccacctc ctcctgctcc ctggacgatc cttggcttgg acgccatgta
1081 tgtcatcatg tggatcacct acatggcgtt tttgcttgtg ttttttggag cattttttgc
1141 agtgtggtgc tacagaaaac ggtattttgt ctccgagtac actcccatcg atagcaatat
1201 agcttttct gttaatgcaa gtgacaaagg agaggcgtcc tgctgtgacc ctgtcagcgc
1261 agcatttgag ggctgcttga ggcggctgtt cacacgctgg ggtctttct gcgtccgaaa
1321 ccctggctgt gtcattttct tctcgctggt cttcattact gcgtgttcgt caggcctggt
1381 gtttgtccgg gtcacaacca atccagttga cctctggtca gcccccagca gccaggctcg
1441 cctggaaaaa gagtactttg accagcactt tgggcctttc ttccggacgg agcagctcat
1501 catccgggcc cctctcactg acaaacacat ttaccagcca tacccttcgg gagctgatgt
1561 acccttggga cctccgcttg acatacagat actgcaccag gttcttgact acaaatagc
1621 catcgaaaac attactgcct cttatgacaa tgagactgtg acacttcaag acatctgctt
1681 ggcccctctt tcaccgtata acacgaactg caccattttg agtgtgttaa attacttcca
1741 gaacagccat tccgtgctgg accacaagaa aggggacgac ttctttgtgt atgccgatta
1801 ccacacgcac tttctgtact gcgtacgggc tcctgcctct ctgaatgata caagtttgct
1861 ccatgaccct tgtctgggta cgtttggtgg accagtgttc ccgtggcttg tgttgggagg
1921 ctatgatgat caaaactaca ataacgccac tgcccttgtg attaccttcc ctgtcaataa
1981 ttactataat gatacagaga agctccagag ggcccaggcc tgggaaaaag agtttattaa
2041 ttttgtgaaa aactacaaga atcccaatct gaccatttcc ttcactgctg aacgaagtat
2101 tgaagatgaa ctaaatcgtg aaagtgacag tgatgtcttc accgttgtaa ttagctatgc
2161 catcatgttt ctatatattt ccctagcctt ggggcacatg aaaagctgtc gcaggcttct
2221 ggtggattcg aaggtctcac taggcatcgc gggcatcttg atcgtgctga gctcggtggc
2281 ttgctccttg ggtgtcttca gctacattgg gttgcccttg accctcattg tgattgaagt
2341 catcccgttc ctggtgctgg ctgttggagt ggacaacatc ttcattctgg tgcaggccta
2401 ccagagagat gaacgtcttc aaggggaaac cctggatcag cagctgggca gggtcctagg
2461 agaagtggct cccagtatgt tcctgtcatc ctttctgag actgtagcat ttttcttagg
2521 agcattgtcc gtgatgccag ccgtgcacac cttctctctc tttgcgggat tggcagtctt
2581 cattgacttt cttctgcaga ttacctgttt cgtgagtctc ttgggttag acattaaacg
2641 tcaagagaaa aatcggctag acatcttttg ctgtgtcaga ggtgctgaag atggaacaag
2701 cgtccaggcc tcagagagct gtttgtttcg cttcttcaaa aactcctatt ctccacttct
2761 gctaaaggac tggatgagac caattgtgat agcaatattt gtgggtgttc tgtcattcag
2821 catcgcagtc ctgaacaaag tagatattgg attggatcag tctctttcga tgccagatga
2881 ctcctacatg gtggattatt tcaaatccat cagtcagtac ctgcatgcgg tccgcctgt
2941 gtactttgtc ctggaggaag ggcacgacta cacttcttcc aaggggcaga acatggtgtg
3001 cggcggcatg ggctgcaaca atgattccct ggtgcagcag atatttaacg cggcgcagct
3061 ggacaactat acccgaatag gcttcgcccc ctcgtcctgg atcgacgatt atttcgactg
3121 ggtgaagcca cagtcgtctt gctgtcgagt ggacaatatc actgaccagt tctgcaatgc
```

```
3181 ttcagtggtt gaccctgcct gcgttcgctg caggcctctg actccggaag gcaaacagag
3241 gcctcagggg ggagacttca tgagattcct gcccatgttc ctttcggata accctaaccc
3301 caagtgtggc aaaggggac atgctgccta tagttctgca gttaacatcc tccttggcca
3361 tggcaccagg gtcggagcca cgtacttcat gacctaccac accgtgctgc agacctctgc
3421 tgactttatt gacgctctga agaaagcccg acttatagcc agtaatgtca ccgaaaccat
3481 gggcattaac ggcagtgcct accgagtatt tccttacagt gtgttttatg tcttctacga
3541 acagtacctg accatcattg acgacactat cttcaacctc ggtgtgtccc tgggcgcgat
3601 atttctggtg accatggtcc tcctgggctg tgagctctgg tctgcagtca tcatgtgtgc
3661 caccatcgcc atggtcttgg tcaacatgtt tggagttatg tggctctggg catcagtct
3721 gaacgctgta tccttggtca acctggtgat gagctgtggc atctccgtgg agttctgcag
3781 ccacataacc agagcgttca cggtgagcat gaaaggcagc cgcgtggagc gcgcggaaga
3841 ggcacttgcc cacatgggca gctccgtgtt cagtggaatc acacttacaa aatttggagg
3901 gattgtggtg ttggcttttg ccaaatctca aattttccag atattctact tcaggatgta
3961 tttggccatg gtcttactgg gagccactca cggattaata tttctccctg tcttactcag
4021 ttacataggg ccatcagtaa ataaagccaa aagttgtgcc actgaagagc gatacaaagg
4081 aacagagcgc gaacggcttc taaatttcta gccctctcgc agggcatcct gactgaactg
4141 tgtctaaggg tcggtcggtt taccactgga cgggtgctgc atcggcaagg ccaagttgaa
4201 caccggatgg tgccaaccat cggttgtttg gcagcagctt tgaacgtagc gcctgtgaac
4261 tcaggaatgc acagttgact tgggaagcag tattactaga tctggaggca accacaggac
4321 actaaacttc tcccagcctc ttcaggaaag aaacctcatt ctttggcaag caggaggtga
4381 cactagatgg ctgtgaatgt gatccgctca ctgacactct gtaaaggcca atcaatgcac
4441 tgtctgtctc tccttttagg agtaagccat cccacaagtt ctataccata tttttagtga
4501 cagttgaggt tgtagataca ctttataaca ttttatagtt taaagagctt tattaatgca
4561 ataaattaac tttgtacaca tttttatata aaaaaacagc aagtgatttc agaatgttgt
4621 aggcctcatt agagcttggt ctccaaaaat ctgtttgaaa aaagcaacat gttcttcaca
4681 gtgttcccct agaaaggaag agatttaatt gccagttaga tgtggcatga aatgagggac
4741 aaagaaagca tctcgtaggt gtgtctactg ggttttaact tattttcttt taataaaata
4801 cattgttttc ctaaaaaaaa aaaaaaa
```

The invention also provides monoclonal antibodies to NPC1.

Examples of anti-NPC1 antibody amino acid sequences of variable regions for light and heavy chains include:

401-variable light chain (mouse)
(SEQ ID NO: 3)
DIQMTQSPASLSASVGETVTITCRASENIYSYLAWYQQKQGKSPQLLVYN

AKTLVEAVPSRFSGSGSGTQFSLKINSLQPEDFGTYYCQHHYGSPWTFGG

GTKLEIK, 401-variable heavy chain (mouse)
(SEQ ID NO: 4)
EVQLQQSGAELVKPGASVKLSCTASGFNIKDTYMHWVKQRPEQGLEWIGR

IDPANGNTEYDTKFQGKATITADTSSNTAYLQLSSLTSEDTAVYYCSRGY

YWGRGTTLVTVSS, 548-variable light chain (mouse)
(SEQ ID NO: 5)
DIQMTQSPASLSASVGETVTITCRASENIYSYLAWYQQKQGKSPQLLVYN

AKTLAEGVPSRFSGSGSGTQFSLKINSLQPEDFGIYYCQHHYGSPWAFGG

GTKLEIK, 548-variable heavy chain (mouse)
(SEQ ID NO: 6)
EVQLQQSGAELVKPGASVKLSCTASGFNIKDTYMHWVKQRPEEGLEWIGR

IDPADGNTEYVPKFQGKATITADTFSNTVYLQLSGLTSEDTAVYYCSRGY

YWGQGTTLVTVSS, 952-variable light chain (mouse)
(SEQ ID NO: 7)
DIVMTQSHKFMSTSVGDRVSITCKASQDVNTAVVWYQQKPGQSPKLLIYW

ASTRHTGVPDRFTGSGSGTDFTLTISSVQAEDLALYYCQQHYTSPWTFGG

GTKLEIK,
and 952-variable heavy chain (mouse)
(SEQ ID NO: 8)
DVQLQESGPDLVKPXQSLSLTCTVTGYSITSGYSWHWIRQFPGNRLEWMD

YIHYSGSINYNPSLKSRISITRDTSKNQFFLQLNSVTTEDTATYYCARWG

ATGFDYWGQGTTLVTVSS.

Examples of bispecific Ab design include the following. The underlined region designates glycine-rich linker polypeptide. The bold region designates fusion linker polypeptide. The italicized region corresponds to the constant sequences of the pMAZ-encoded heavy or light constant region sequences for human IgG1 (heavy) and kappa constant domain (light).

401-scFv-KZ52-HCN (heavy chain N-terminal fusion) (in all of the following scFv-KZ52 bispecifics: scFv is human, IgG HC and LC constant domains are human IgG1, IgG VH and VL domains are mouse)
(SEQ ID NO: 9)
EVQLLESGGGLVKPGGSLRLSCAASGFTLINYRMNWVRQAPGKGLEWVSSISSSSSYIHYADSVKGRFTISRDNAE NSLYLQMNSLRAEDTAVYYCVREGPRATGYSMADVFDIWGQGTMVTVSS<u>GGGGSGGGGSGGGGS</u>ELVMTQSPDSLA

VSLGERATINCKSSQSVLYSSNNKSYLAWYQQKPGQPPKLLIYWASTRESGVPDRFSGSGSGTDFTLTISSLQAED

VAVYYCQQYYSAPLTFGGGTKVEIKGGSAGSAGSAGSGGSEVQLQQSGAELVKPGASVKLSCTASGFNIKDTYMHW

*VKQRPEQGLEWIGRIDPANGNTEYDTKFQGKATITADTSSNTAYLQLSSLTSEDTAVYYCSRGYYWGRGTTLVTVS*

*SASTKGPSVFPLAPSSKSTSGGTAALGCLVKDYFPEPVTVSWNSGALTSGVHTFPAVLQSSLGYSLSSVVTVPSSS*

*LGTQTYICNVNHKPSNTKVDKKVEPKSCDKTHTCPPCPAPELLGRPSVFLFPPKPKDTLMISRTPEVTCVVVDVSH*

*EDPEVKFNWYVDGVEVHNAKTKPREEQYNSTYRVVSVLTVLHQDWLNGKEYKCKVSNKALPAPIEKTISKAKGQPR*

*EPQVYTLPPSREEMTKNQVSLTCLVKGFYPSDIAVEWESNGQPENNYKTTPPVLDSDGSFFLYSKLTVDKSRWQQG*

*NVFSCSVMHEALHNHYTQKSLSLSPGK*, 401-scFv-KZ52-LCN (light chain N-terminal fusion)
(SEQ ID NO: 10)
EVQLLESGGGLVKPGGSLRLSCAASGFTLINYRMNWVRQAPGLGLEWVSSISSSSSYIHYADSVKGRFTISRDNAE NSLYLQMNSLRAEDTAVYYCVREGPRATGYSMADVFDIWGQGTMVTVSS<u>GGGGSGGGGSGGGGS</u>ELVMTQSPDSLA

VSLGERATINCKSSQSVLYSSNNKSYLAWYQQKPGQPPKLLIYWASTRESGVPDRFSGSGSGTDFTLTISSLQAED

VAVYYCQQYYSAPLTFGGGTKVEIKGGSAGSAGSAGSGGSDIQMTQSPASLSASVGETVTITCRASENIYSYLAWY

QQKQGKSPQLLVYNAKTLVEAVPSRFSGSGSGTQFSLKINSLQPEDFGTYYCQHHYGSPWTFGGGTKLEIKRT*VAA*

*PSVFIFPPSDEQLKSGTASVVCLLNNFYPREAKVQWKVDNALQSGNSQESVTEQDSKDSTYSLSSTLTLSKADYEK*

*HKVYACEVTHQGLSSPVTKSFNRGEC*, 401-scFv-KZ52-HCC (heavy chain C-terminal fusion)
(SEQ ID NO: 11)
EVQLQQSGAELVKPGASVKLSCTASGFNIKDTYMHWVKQRPEQGLEWIGRIDPANGNTEYDTKFQGKATITADTSS

NTAYLQLSSLTSEDTAVYYCSRGYYWGRGTTLVTVSS*ASTKGPSVFPLAPSSKSTSGGTAALGCLVKDYFPEPVTVS*

*WNSGALTSGVHTFPAVLQSSLGYSLSSVVTVPSSSLGTQTYICNVNHKPSNTKVDKKVEPKSCDKTHTCPPCPAPE*

*LLGRPSVFLFPPKPKDTLMISRTPEVTCVVVDVSHEDPEVKFNWYVDGVEVHNAKTKPREEQYNSTYRVVSVLTVL*

*HQDWLNGKEYKCKVSNKALPAPIEKTISKAKGQPREPQVYTLPPSREEMTKNQVSLTCLVKGFYPSDIAVEWESNG*

*QPENNYKTTPPVLDSDGSFFLYSKLTVDKSRWQQGNVFSCSVMHEALHNHYTQKSLSLSPGK*GGSAGSAGSAGSGG

SEVQLLESGGGLVKPGGSLRLSCAASGFTLINYRMNWVRQAPGKGLEWVSSISSSSSYIHYADSVKGRFTISRDNA

ENSLYLQMNSLRAEDTAVYYCVREGPRATGYSMADVFDIWGQGTMVTVSS<u>GGGGSGGGGSGGGGS</u>ELVMTQSPDSL

AVSLGERATINCKSSQSVLYSSNNKSYLAWYQQKPGQPPKLLIYWASTRESGVPDRFSGSGSGTDFTLTISSLQAE

DVAVYYCQQYYSAPLTFGGGTKVEIK,

-continued 401-scFv-KZ52-LCC (light chain C-terminal fusion)
(SEQ ID NO: 12)
DIQMTQSPASLSASVGETVTITCRASENIYSYLAWYQQKGKSPQLLVYNAKTLVEAVPSRFSGSGSGTQFSLKIN
SLQPEDFGTYYCQHHYGSPWTFGGGTKLEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC**GGSAGSAGSAGSGG
S**EVQLLESGGGLVKPGGSLRLSCAASGFTLINYRMNWVRQAPGKGLEWVSSISSSSSYIHYADSVKGRFTISRDNA
ENSLYLQMNSLRAEDTAVYYCVREGPRATGYSMADVFDIWGQGTMVTVSSGGGGSGGGGSGGGGSELVMTQSPDSL
AVSLGERATINCKSSQSVLYSSNNKSYLAWYQQKPGQPPKLLIYWASTRESGVPDRFSGSGSGTDFTLTISSLQAE
DVAVYYCQQYYSAPLTFGGGTKVEIK, 548-scFv-KZ52-HCN (heavy chain N-terminal fusion)
(SEQ ID NO: 13)
EVQLLESGGGLVKPGGSLRLSCAASGFTLINYRMNWVRQAPGKGLEWVSSISSSSSYIHYADSVKGRFTISRDNAE
NSLYLQMNSLRAEDTAVYYCVREGPRATGYSMADVFDIWGQGTMVTVSSGGGGSGGGGSGGGGSELVMTQSPDSLA
VSLGERATINCKSSQSVLYSSNNKSYLAWYQQKPGQPPKLLIYWASTRESGVPDRFSGSGSGTDFTLTISSLQAED
VAVYYCQQYYSAPLTFGGGTKVEIKGGSAGSAGSAGSGGSEVQLQQSGAELVKPGASVKLSCTASGFNIKDTYMHW
VKQRPEEGLEWIGRIDPADGNTYEVPKFQGKATITADTFSNTVYLQLSGLTSEDTAVYYCSRGYYWGQGTTLTVSS
ASTKGPSVFPLAPSSKSTSGGTAALGCLVKDYFPEPVTVSWNSGALTSGVHTFPAVLQSSLGYSLSSVVTVPSSSL
GTQTYICNVNHKPSNTKVDKKVEPKSCDKTHTCPPCPAPELLGRPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSFFLYSKLTVDKSRWQQGN
VFSCSVMHEALHNHYTQKSLSLSPGK, 548-scFv-KZ52-LCN (light chain N-terminal fusion)
(SEQ ID NO: 14)
EVQLLESGGGLVKPGGSLRLSCAASGFTLINYRMNWVRQAPGKGLEWVSSISSSSSYIHYADSVKGRFTISRDNAE
NSLYLQMNSLRAEDTAVYYCVREGPRATGYSMADVFDIWGQGTMVTVSSGGGGSGGGGSGGGGSELVMTQSPDSLA
VSLGERATINCKSSQSVLYSSNNKSYLAWYQQKPGQPPKLLIYWASTRESGVPDRFSGSGSGTDFTLTISSLQAED
VAVYYCQQYYSAPLTFGGGTKVEIKGGSAGSAGSAGSGGSDIQMTQSPASLSASVGETVTITCRASENIYSYLAWY
QQKGKSPQLLVYNAKTLAEGVPSRFSGSGSGTQFSLKINSLQPEDFGIYYCQHHYGSPWAFGGGTKLEIKRTVAA
PSVFIFPPSDEQLKSGTASVVCLLNNFYPREAKVQWKVDNALWSGNSQESVTEQDSKSDTYSLSSTLTLSKADYEK
HKVYACEVTHQGLSSPVTKSFNRGEC, 548-scFv-KZ52-HCC (heavy chain C-terminal fusion)
(SEQ ID NO: 15)
EVQLQQSAGELVKPGASVKLSCTASGFNIKDTYMHWVKQRPEEGLEWIGRIDPADGNTEYVPKFQGKATITADTFS
NTVYLQLSGLTSEDTAVYYCSRGYYWGQGTTLTVSSASTKGPSVFPLAPSSKSTSGGTAALGCLVKDYFPEPVTVS
WNSGALTSGVHTFPAVLQSSLGYSLSSVVTVPSSSLGTQTYICNVNHKPSNTKVDKKVEPKSCDKTHTCPPCPAPE
LLGRPSVFLFPPKPKDTLMISRTPEVTCVVVDVSHEDPEVKFDNWYVDGVEVHNAKTKPREEQYNSTYRVVSVLTVL
HQDWLNGKEYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK**GGSAGSAGSAGSGG
S**EVQLLESGGGLVKPGGSLRLSCAASGFTLINYRMNWVRQAPGKGLEWVSSISSSSSYIHYADSVKGRFTISRDNA
ENSLYLQMNSLRAEDTAVYYCVREGPRATGYSMADVFDIWGQGTMVTVSSGGGGSGGGGSGGGGSELVMTQSPDSL
AVSLGERATINCKSSQSVLYSSNNKSYLAWYQQKPGQPPKLLIYWASTRESGVPDRFSGSGSGTDFTLTISSLQAE
DVAVYYCQQYYSAPLTFGGGTKVEIK, 548-scFv-KZ52-LCC (light chain C-terminal fusion)
(SEQ ID NO: 16)
DIQMTQSPASLSASVGETVTITCRASENIYSYLAWYQQKQGKSPQLLVYNAKTLAEGVPSRFSGSGSGTQFSLKIN
SLQPEDFGIYYCQHHYGSPWAFGGGTKLEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC**GGSAGSAGSAGSGG
S**EVQLLESGGGLVKPGGSLRLSCAASGFTLINYRMNWVRQAPGKGLEWVSSISSSSSYIHYADSVKGRFTISRDNA
ENSLYLQMNSLRAEDTAVYYCVREGPRATGYSMADVFDIWGQGTMVTVSS<u>GGGGSGGGGSGGGGS</u>ELVMTQSPDSL
AVSLGERATINCKSSQSVLYSSNNKSYLAWYQQKPGQPPKLLIYWASTRESGVPDRFSGSGSGTDFTLTISSLQAE
DVAVYYCQQYYSAPLTFGGGTKVEIK, 952-scFv-KZ52-HCN (heavy chain N-terminal fusion)
(SEQ ID NO: 17)
EVQLLESGGGLVKPGGSLRLSCAASGFTLINYRMNWVRQAPGKGLEWVSSISSSSSYIHYADSVKGRFTISRDNAE
NSLYLQMNSLRAEDTAVYYCVREGPRATGYSMADVFDIWGQGTMVTVSS<u>GGGGSGGGGSGGGGS</u>ELVMTQSPDSLA
VSLGERATINCKSSQSVLYSSNNKSYLAWYQQKPGQPPKLLIYWASTRESGVPDRFSGSGSGTDFTLTISSLQAED
VAVYYCQQYYSAPLTFGGGTKVEIKGGSAGSAGSAGSGGSDVQLQESGPDLVKPXQSLSLTCTVTGYSITSGYSWH
WIRQFPGNRLEWMDYIHYSGSINYNPSLKSRISITRDTSKNQFFLQLNSVTTEDTATYYCARWGATGFDYWGQGTT
LTVSSASTKGPSVFPLAPSSKSTSGGTAALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPELLGRPSVFLFPPKPKDTLMISRTPEVTCVVV
DVSHEDPEVKFNWYVDGVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLDSDGSFFLYSKLTVDKSR
WQQGNVFSCSVMHEALHNHYTQKSLSLSPGK, 952-scFv-KZ52-LCN (light chain N-terminal fusion)
(SEQ ID NO: 18)
EVQLLESGGGLVKPGGSLRLSCAASGFTLINYRMNWVRQAPGKGLEWVSSISSSSSYIHYADSVKGRFTISRDNAE
NSLYLQMNSLRAEDTAVYYCVREGPARTGYSMADVFDIWGQGTMVTVSS<u>GGGGSGGGGSGGGGS</u>ELVMTQSPDSLA
VSLGERATINCKSSQSVLYSSNNKSYLAWYQQKPGQPPKLLIYWASTRESGVPDRFSGSGSGTDFTLTISSLQAED
VAVYYCQQYYSAPLTFGGGTKVEIKGGSAGSAGSAGSGGSDIVMTQSHKFMSTSVGDRVSITCKASQDVNTAVVWY
QQKPGQSPKLLIYWASTRHTGVPDRFTGSGSGTDFTLTISSVQAEDLALYYCQQHYTSPWTFGGGTKLEIKRTVAA
PSVFIFPPSDEQLKSGTASVVCLLNNFYPREAKVQWKVDNALQSGNSQESVTQEDSKDSTYSLSSTLTLSKADYEK
HKVYACEVTHQGLSSPVTKSFNRGEC, 952-scFv-KZ52-HCC (heavy chain C-terminal fusion)
(SEQ ID NO: 19)
DVQLQESGPDLVKPXQSLSLTCTVTGYSITSGYSWHWIRQFPGNRLEWMDYIHYSGSINYNPSLKSRISITRDTSK
NQFFLQLNSVTTEDTATYYCARWGATGDFYWGQGTTLTVSSASTKGPSVFPLAPSSKSTSGGTAALGCLVKDYFPE
PVTVSWNSGALTSGVHTFPAVLQSSLGYSLSSVVTVPSSSLGTQTYICNVNHKPSNTKVDKKVEPKSCDKTHTCPP
HTCPPCPAPELLGRPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMHEALHNHYTQKSLSLSPGK**GGSA
GSAGSAGSGGS**EVQLLESGGGLVKPGGSLRLSCAASGFTLINYRMNWVRQAPGKGLEWVSSISSSSSYIHYADSVK
GRFTISRDNAENSLYLQMNSLRAEDTAVYYCVREGPRATGYSMADVFDIWGQGTMVTVSS<u>GGGGSGGGGSGGGGS</u>E
LVMTQSPDSLAVSLGERATINCKSSQSVLYSSNNKSYLAWYQQKPGQPPKLLIYWASTRESGVPDRFSGSGSGTDF
TLTISSLQAEDVAVYYCQQYYSAPLTFGGGTKVEIK,
and -continued
952-scFv-KZ52-LCC (light chain C-terminal fusion)
(SEQ ID NO: 20)
DIVMTQSHKFMSTSVGDRVSITCKASQDVNTAVVWYQQKPGQSPKLLIYWASTRHTGVPDRFTGSGSGTDFTLTIS

SVQAEDLALYYCQQHYTSPWTFGGGTKLEIK*RTVAAPSVFIFPPSDEQLKSGTASVVCLLNNFYPREAKVQWKVDN*

*ALQSGNSQESVTEQDSKDSTYSLSSTLTLSKADYEKHKVYACEVTHQGLSSPVTKSFNRGEC*GGSAGSAGSAGSGG

SEVQLLESGGGLVKPGGSLRLSCAASGFTLINYRMNWVRQAPGKGLEWVSSISSSSSYIHYADSVKGRFTISRDNA

ENSLYLQMNSLRAEDTAVYYCVREGPRATGYSMADVFDIWGQGTMVTVSS<u>GGGGSGGGGSGGGGS</u>ELVMTQSPDSL

AVSLGERATINCKSSQSVLYSSNNKSYLAWYQQKPGQPPKLLIYWASTRESGVPDRFSGSGSGTDFTLTISSLQAE

DVAVYYCQQYYSAPLTFGGGTKVEIK.

Additional examples include the following. The italicized region corresponds to the constant sequences of the pMAZ-encoded heavy or light constant region sequences for human IgG1. The underlined region designates fusion linker polypeptide. The bold region designates the sequence of human NPC2.

401-NPC2-HCC (NPC2 C-terminal fusion to heavy chain
of 401 IgG1) (in all of the following bispecifics:
NPC2 is human, IgG HC and LC constant domains are
human IgG1, IgG VH and VL domains are mouse)
(SEQ ID NO: 21)
EVQLQQSGAELVKPGASVKLSCTASGFNIKDTYMHWVKQRPEQGLEWIGRI

DPANGNTEYDTKFQGKATITADTSSNTAYLQLSSLTSEDTAVYYCSRGYYW

GRGTTLTVSS*ASTKGPSVFPLAPSSKSTSGGTAALGCLVKDYFPEPVTVSW*

*NSGALTSGVHTFPAVLQSSGLYSLSSVVTVPSSSLGTQTYICNVNHKPSNT*

*KVDKKVEPKSCDKTHTCPPCPAPELLGRPSVFLLFPPKPKDTLMISRTPEV*

*TCVVVDVSHEDPEVKFNWYVDGVEVHNAKTKPREFQYNSTYRVVSVLTVLH*

*QDWLNGKEYKCKVSNKALPAPIEKTISKAKGQPREPQVYTLPPSREEMTKN*

*QVSLTCLVKGFYPSDIAVEWESNGQPENNYKTTPPVLDSDGSFFLYSKLTV*

*DKSRWQQGNVFSCSVMHEALHNHYTQKSLSLSPGK*<u>GGSAGSAGSAGSGGSE</u>

PVQFKDCGSVDGVIKEVNVSPCPTQPCQLSKGQSYSVNVTFTSNIQSKSSK

AVVHGILMGVPVPFPIPEPDGCKSGINCPIQKDKTYSYLNKLPVKSEYPSI

KLVVEWQLQDDHNQSLFCWEIPVQIVSHL,
and

548-NPC2-HCC (NPC2 C-terminal fusion to heavy chain
of 548 IgG1)
(SEQ ID NO: 22)
EVQLQQSGAELVKPGASVKLSCTASGFNIKDTYMHWVKQRPEEGLEWIGRI

DPADGNTEYVPKFQGKATITADTFSNTVYLQLSGLTSEDTAVYYCSRGYYW

GQGTTLTVSS*ASTKGPSVFPLAPSSKSTSGGTAALGCLVKDYFPEPVTVSW*

*NSGALTSGVHTFPAVLQSSGLYSLSSVVTVPSSSLGTQTYICNVNHKPSNT*

*KVDKKVEPKSCDKTHTCPPCPAPELLGRPSVFLFPPKPKDTLMISRTPEVT*

*CVVVDVSHEDPEVKFNWYVDGVEVHNAKTKPREEQYNSTYRVVSVLTVLHQ*

*DWLNGKEYKCKVSNKALPAPIEKTISKAKGQPREPQVYTLPPSREEMTKNQ*

*VSLTCLVKGFYPSDIAVEWESNGQPENNYKTTPPVLDSDGSFFLYSKLTVD*

*KSRWQQGNVFSCSVMHEALHNHYTQKSLSLSPGK*<u>GGSAGSAGSAGSGGS</u>EP

VQFKDCGSVDGVIKEVNVSPCPTQPCQLSKGQSYSVNVTFTSNIQSKSSKA

VVHGILMGVPVPFPIPEPDGCKSGINCPIQKDKTYSYLNKLPVKSEYPSIK

LVVEWQLQDDKNQSLFCWEIPVQIVSHL.

Preferably, 548 has the following epitope, DFFVYADYHT (SEQ ID NO: 23), which corresponds to residues 502-511 of human NPC1.

Preferably, the monoclonal antibody or bispecific antibody is a human antibody or humanized antibody. "Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region (HVR) of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin variable domain are replaced by corresponding non-human residues. These modifications may be made to further refine antibody performance. Furthermore, in a specific embodiment, humanized antibodies may comprise residues that are not found in the recipient antibody or in the donor antibody. In an embodiment, the humanized antibodies do not comprise residues that are not found in the recipient antibody or in the donor antibody. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See, e.g., Jones et al., Nature 321:522-525 (1986); Riechmann et al., Nature 332:323-329 (1988); Presta, Curr. Op. Struct. Biol. 2:593-596 (1992); Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409, the contents of each of which references and patents are hereby incorporated by reference in their entirety. In one embodiment where the humanized antibodies do comprise residues that are not found in the recipient antibody or in the donor antibody, the Fc regions of the antibodies are modified as described in WO 99/58572, the content of which is hereby incorporated by reference in its entirety.

Techniques to humanize a monoclonal antibody are described in U.S. Pat. Nos. 4,816,567; 5,807,715; 5,866.692; 6,331,415; 5,530,101; 5,693,761; 5,693,762; 5,585,089; and 6,180,370, the content of each of which is hereby incorporated by reference in its entirety.

A number of "humanized" antibody molecules comprising an antigen-binding site derived from a non-human immunoglobulin have been described, including antibodies having rodent or modified rodent V regions and their associated complementarity determining regions (CDRs) fused to human constant domains. See, for example, Winter et al. Nature 349: 293-299 (1991), Lobuglio et al. Proc. Nat. Acad. Sci. USA 86: 4220-4224 (1989), Shaw et al. J. Immunol. 138: 4534-4538 (1987), and Brown et al. Cancer Res. 47: 3577-3583 (1987), the content of each of which is hereby incorporated by reference in its entirety. Other references describe rodent hypervariable regions or CDRs grafted into a human supporting framework region (FR) prior to fusion with an appropriate human antibody constant domain. See, for example, Riechmann et al. Nature 332: 323-327 (1988), Verhoeyen et al. Science 239: 1534-1536 (1988), and Jones et al. Nature 321: 522-525 (1986), the content of each of which is hereby incorporated by reference in its entirety. Another reference describes rodent CDRs supported by recombinantly veneered rodent framework regions—European Patent Publication No. 0519596 (incorporated by reference in its entirety). These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert (e.g., does not trigger complement lysis). See, e.g. PCT Publication No. WO99/58572, UK Patent Application No. 9809951.8. Other methods of humanizing antibodies that may also be utilized are disclosed by Daugherty et al., Nucl. Acids Res. 19: 2471-2476 (1991) and in U.S. Pat. Nos. 6,180,377; 6,054,297; 5,997,867; 5,866,692; 6,210,671; and 6,350,861; and in PCT Publication No. WO 01/27160 (each incorporated by reference in their entirety).

Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

The invention also provies pharmaceutical compositions for treating or preventing or reducing or inhibiting a Filovirus infection in a subject comprising any of the bispecific antibodies or bispecific fusion constructs disclosed herein and a pharmaceutically acceptable carrier. Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution. The bispecific antibody or bispecific fusion construct can be administered to the subject in a pharmaceutical composition comprising a pharmaceutically acceptable carrier. The pharmaceutically acceptable carrier used can depend on the route of administration. The pharmaceutical composition can be formulated for administration by any method known in the art, including but not limited to, oral administration, parenteral administration, intravenous administration and administration through an osmotic mini-pump.

The invention further provides an isolated nucleic acid encoding any of the bispecific antibodies or bispecific fusion constructs disclosed herein. The isolated nucleic acid can be, or comprise, a cDNA.

This invention will be better understood from the Experimental Details, which follow. However, one skilled in the an will readily appreciate that the specific methods and results discussed are merely illustrative of the invention as described more fully in the claims that follow thereafter.

Experimental Details

Introduction and Overview: Ebola virus (EBOV) and related filoviruses are associated with sporadic outbreaks of highly lethal hemorrhagic fever in Middle and West Africa. The ongoing regional EBOV epidemic in West Africa has underscored the urgent need for antiviral treatments and demonstrated the potential of passive immunotherapy to reverse advanced filovirus disease. However, existing monoclonal antibody (mAb) cocktails such as ZMapp are limited by a narrow spectrum of antiviral action, which stems from viral strain-specific neutralization of the highly variable entry glycoprotein, GP, by most mAbs. Accordingly, set forth herein is an immunotherapeutic strategy targeting the broadly required and highly conserved filovirus entry receptor Niemann-Pick C1 (NPC1) instead of GP. Unfortunately, anti-NPC1 mAbs that efficiently blocked GP-NPC1 interaction in vitro failed to neutralize viral infection in cells, presumably because of an unusual feature of filovirus receptor recognition—the GP-NPC1 interaction can occur only in cellular endosomes where both virus and receptor are likely protected from extracellular antibodies. To overcome this limitation, bispecific Abs (bsAbs) were generated that combine both antiviral and anti-receptor specificities in the same molecule. These bsAbs potently neutralized EBOV infection in a manner that required their engagement of both GP and NPC1, indicating a two-step mechanism of action in which they exploit extracellular virus particles to gain access to NPC1-containing endosomes. bsAbs that combine broadly-reactive (hut non-neutralizing) anti-GP Abs with anti-NPC1 Abs are expected to afford broad-spectrum protection against filovirus infection in vivo.

Figure 1B:
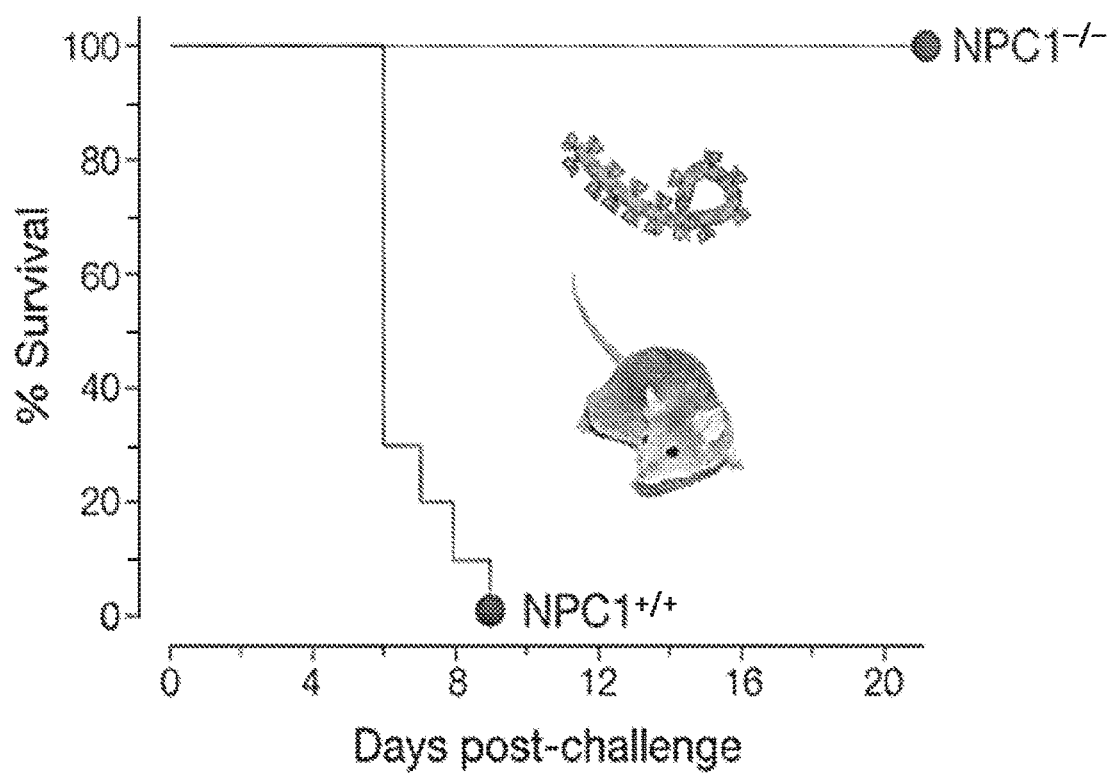
FIG. 1B. NPC1 is required for Ebola in vivo pathogenesis. NPC1-knockout mice (NPC1$^{-/-}$), but not their WT littermates (NPC1$^{+/+}$), are completely resistant to infection and killing by EBOV and MARV.
Figure 2A:
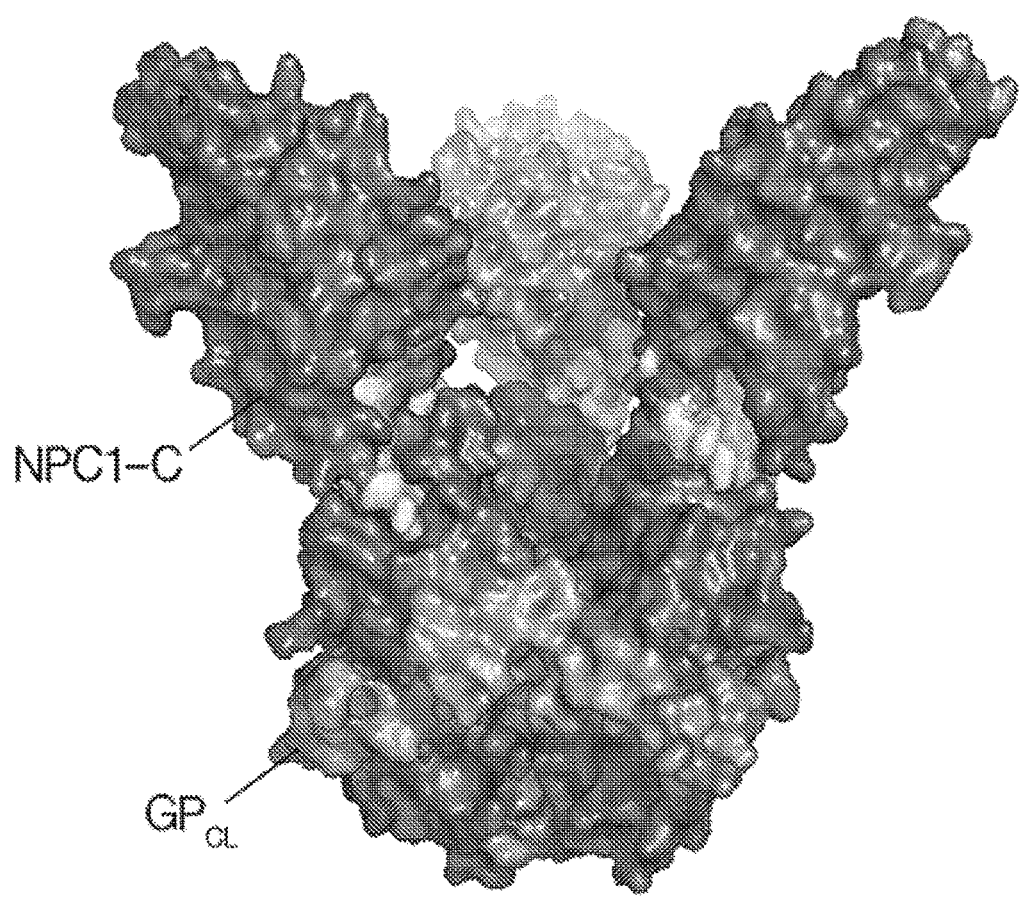
Figure 2B:
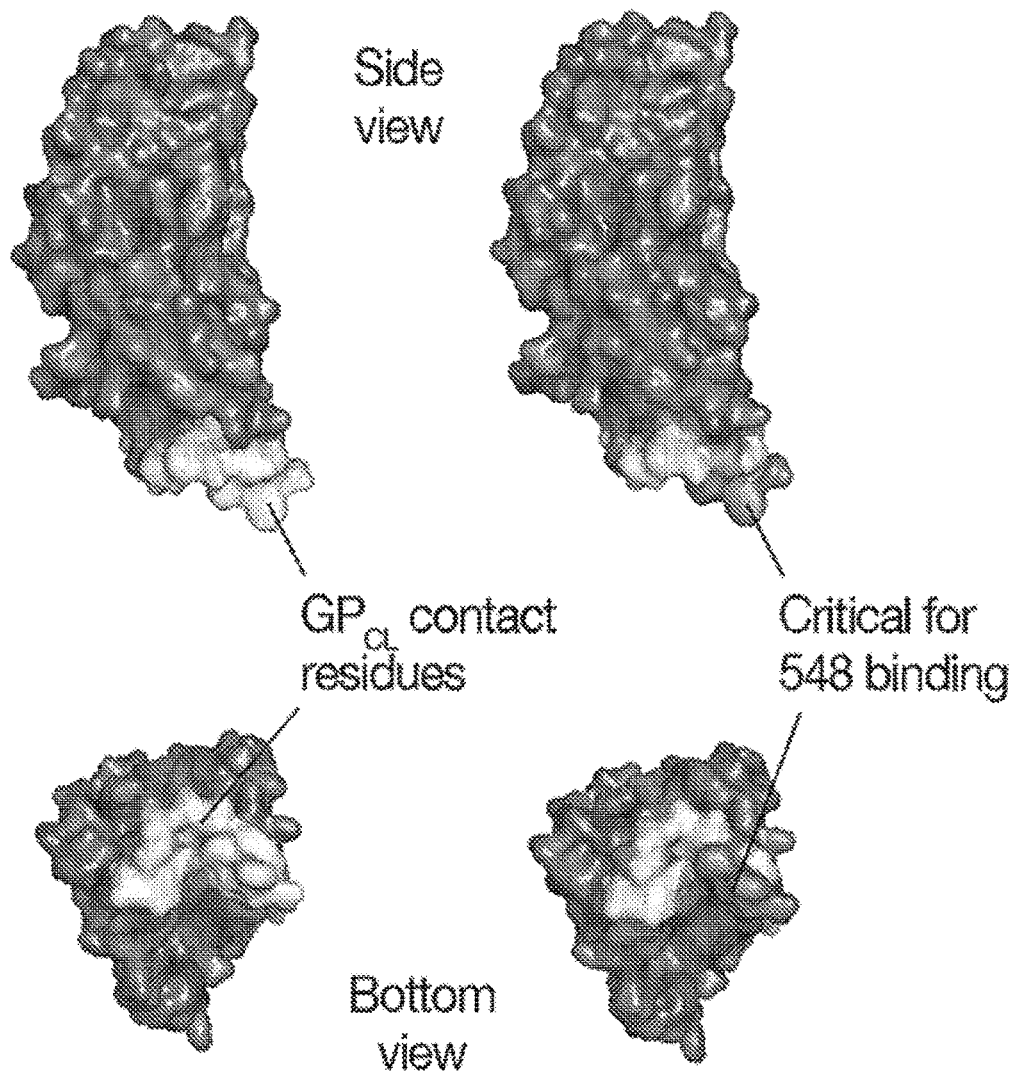
Figure 2C:
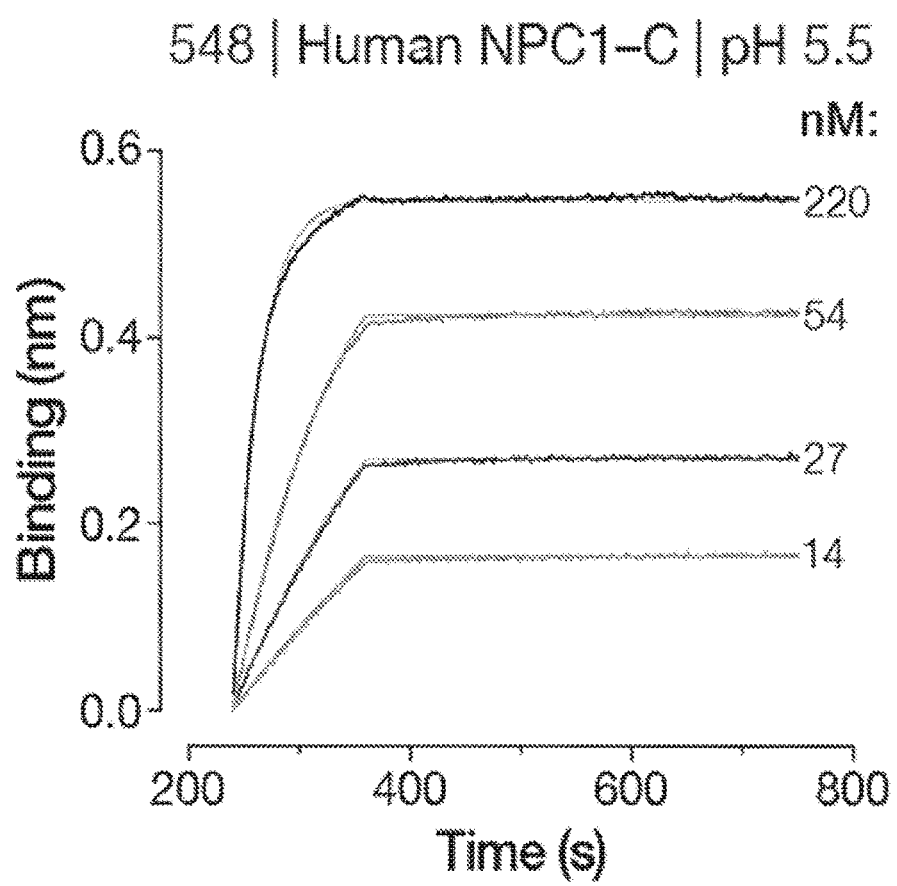

NPC1 is required for Ebola virus infection and in vivo pathogenesis. Niemann-Pick C1 (NPC1), a ubiquitous multi-pass membrane protein localized to late endosomes is required for cytoplasmic entry and infection by all filoviruses. The filovirus spike glycoprotein, GP, must engage NPC1's second luminal domain (FIG. 1A, domain C) to drive viral membrane fusion and cytoplasmic escape (Miller. EMBO J, 2012). As shown in FIG. 1B, NPC1-knockout mice (NPC1$^{-/-}$), but not their WT littermates (NPC1$^{+/+}$), are completely resistant to infection and killing by EBOV and MARV (Carette, Nature 2011; Herbert, submitted).

Figure 3:
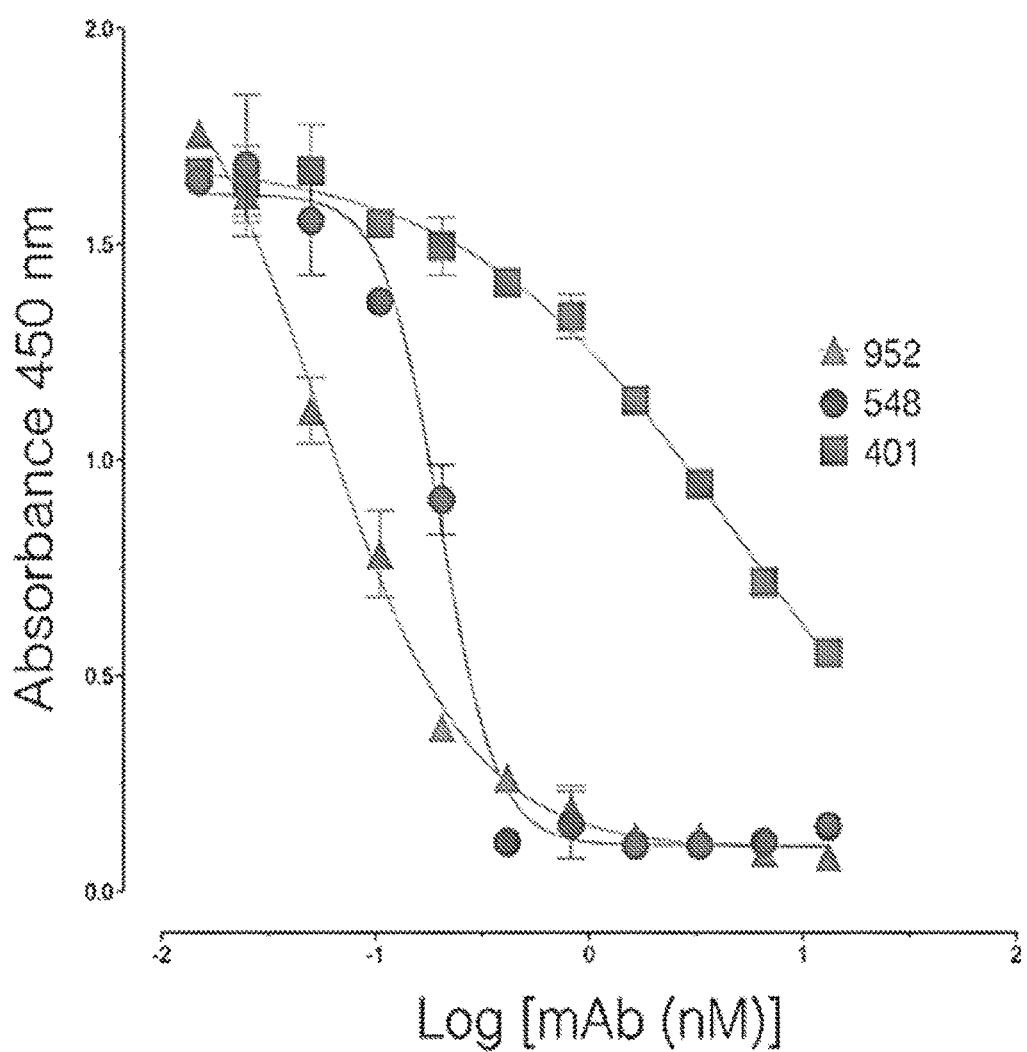
FIG. 3. mAbs specific to human NPC1 domain C block GP-NPC1 binding in vitro. Capacity of three anti-NPC1 mAbs to block GP-NPC1 binding in an ELISA. A soluble, flag-tagged form of NPC1 domain C was pre-incubated with the indicated concentrations of each mAb, and the protein-mAb mixtures were then added to plates coated with vesicular stomatitis virus (VSV) particles bearing EBOV GP. Bound domain C was detected with an anti-flag antibody. Irrelevant isotype-matched antibodies had no effect on GP-NPC1 domain C binding (not shown).

Mouse hybridomas were raised that express mAbs specific for human NPC1 domain C (data not shown). Screens identified two mAbs (548 and 952) that hound with high affinity to NPC1 and potently blocked its interaction with the EBOV glycoprotein GP in vitro. A third mAb (401) had much more modest receptor-blocking activity, FIG. 3 shows the capacity of three anti-NPC1 mAbs to block GP-NPC1 binding in an ELISA. A soluble, flag-tagged form of NPC1 domain C was pre-incubated with the indicated concentrations of each mAb, and the protein-mAb mixtures were then added to plates coated with vesicular stomatitis virus (VSV) particles bearing EBOV GP. Bound domain C was detected with an anti-flag antibody. Irrelevant isotype-matched antibodies had no effect on GP-NPC1 domain C binding (not shown).

Figure 4:
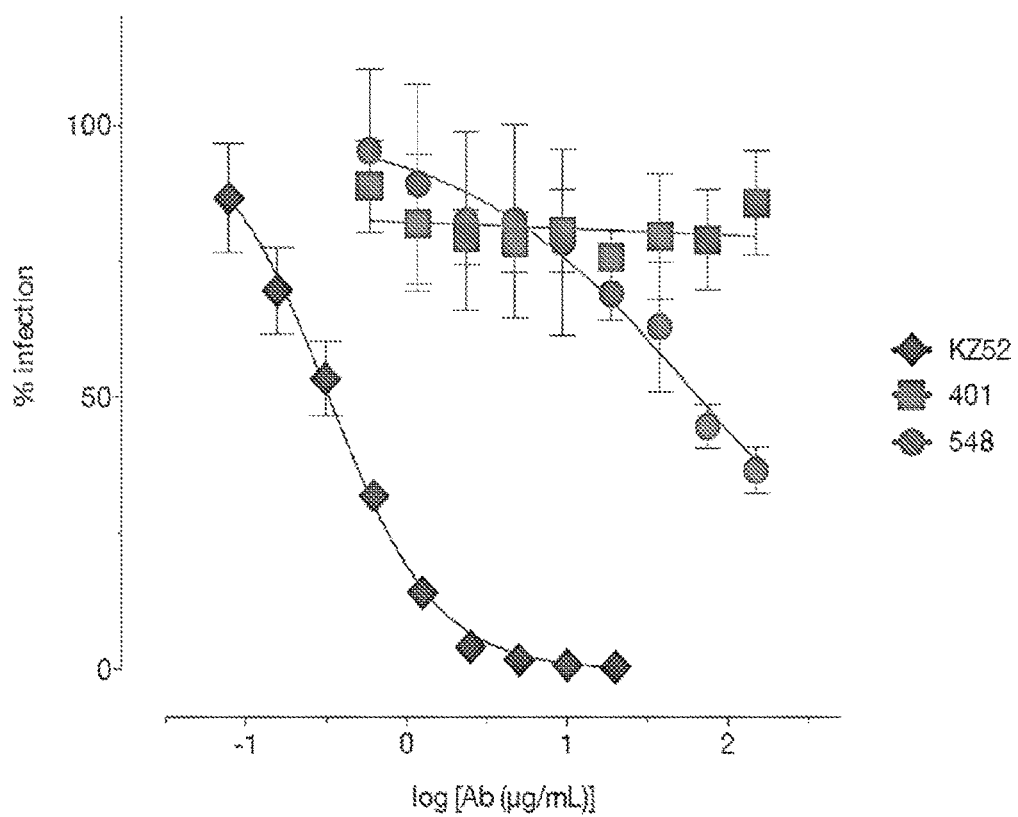
FIG. 4. Anti-NPC1 domain C mAbs neutralize VSV-EBOV GP infection weakly or not at all. VSV-GP particles were exposed to U2OS human osteosarcoma cells in the presence of increasing concentrations of NPC1-specific mAbs or a control GP-specific neutralizing mAb (KZ52). The number of infected cells was determined at 16 h post-infection, and normalized to that obtained in the absence of antibody (set to 100%).

As exemplified in FIG. 4, anti-NPC1 domain C mAbs neutralize VSV-EBOV GP infection weakly or not at all. VSV-GP particles were exposed to U2OS human osteosarcoma cells in the presence of increasing concentrations of NPC1-specific mAbs or a control GP-specific neutralizing mAb (KZ52). The number of infected cells was determined at 16 h post-infection, and normalized to that obtained in the absence of antibody (set to 100%). The NPC1-specific mAbs 548 and 401 neutralized VSV-EBOV OP infection weakly or not at all, respectively. By contrast, the previously described GP-specific neutralizing mAb KZ52 was highly effective at neutralization.

Figure 5A:
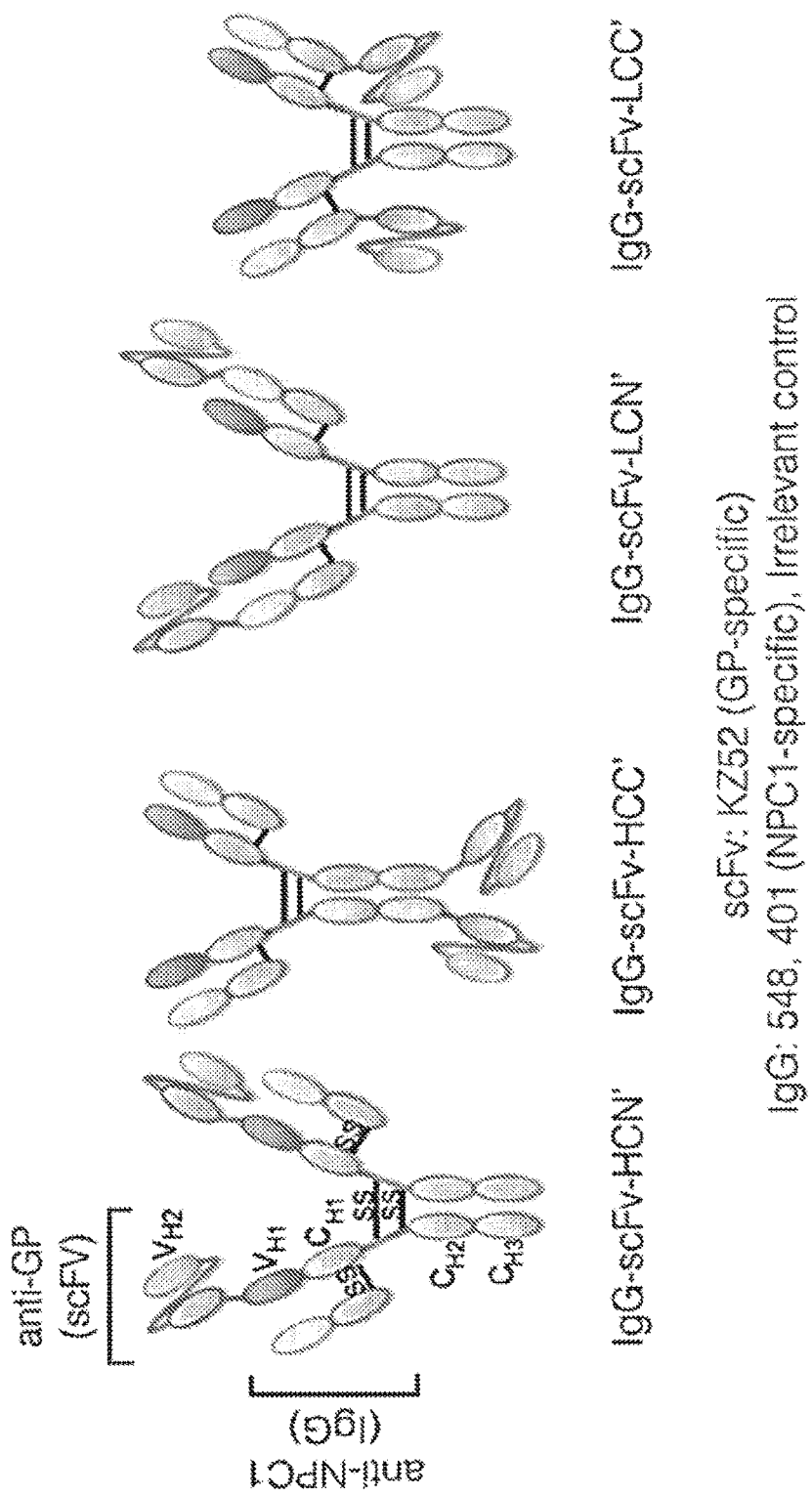
FIG. 5A. Engineering antibodies with dual binding specificities for GP and NPC1. Constructs encoding bsAbs were generated by fusing NPC1-specific or control IgG sequences to a single-chain variable fragment (scFv) sequence derived from the EBOV GP-specific mAb KZ52. Fusions were done in four configurations: to the N- or C-terminus of the IgG heavy chain [HC] or light chain [LC].
Figure 5B:
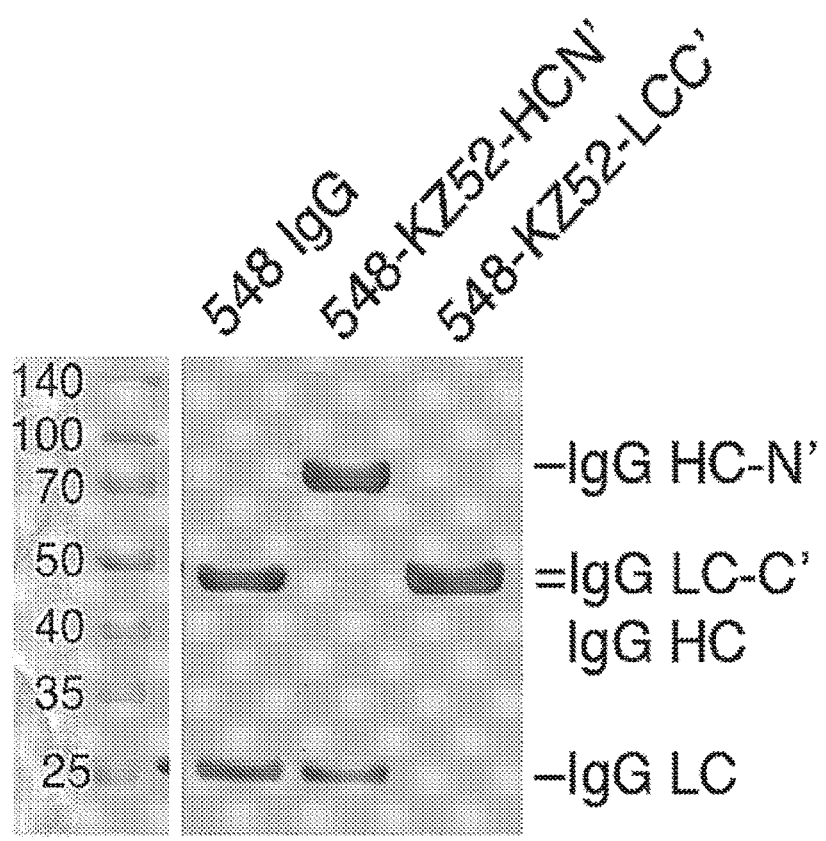
FIG. 5B. Engineering antibodies with dual binding specificities for GP and NPC1. bsAbs and IgGs were expressed in 293-Freestyle cells by co-transfection of HC and LC expression vectors, and purified by protein A affinity chromatography.
Figure 5C:
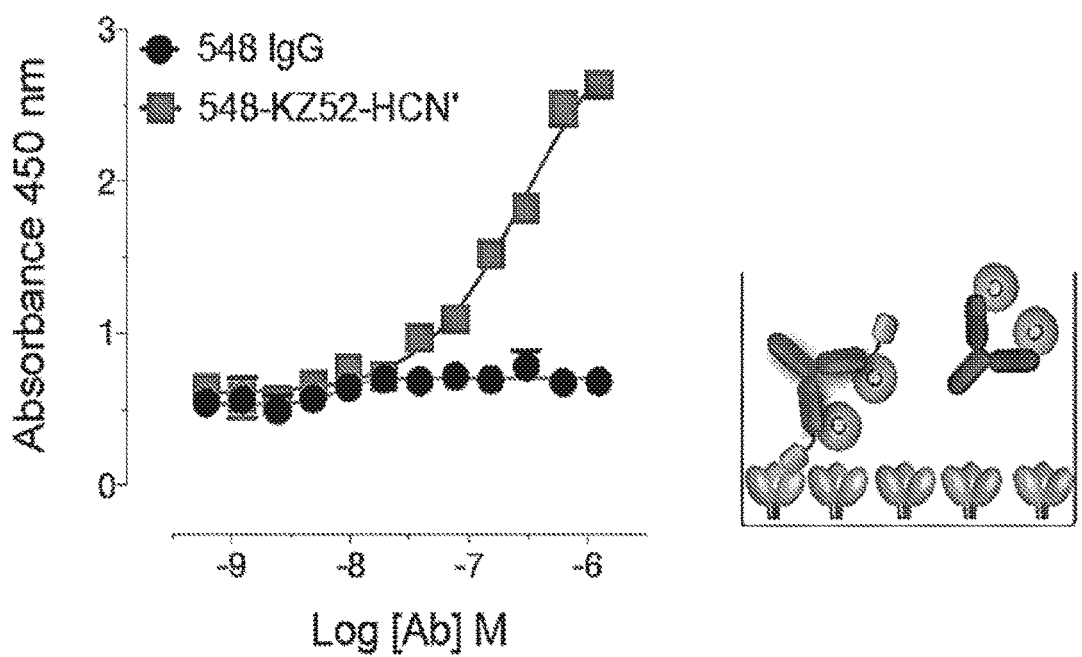
FIG. 5C. bsAbs, but not NPC1-specific IgGs, can simultaneously bind to GP and NPC1 domain C. bsAbs and IgGs were captured onto GP-coated ELISA plates and then incubated with NPC1 domain C-flag. Bound NPC1 domain C was detected with an anti-flag antibody.

FIG. 5 illustrates engineering antibodies with dual binding specificities for GP and NPC1. In FIG. 5A, constructs encoding bsAbs were generated by fusing NPC1-specific or control IgG sequences to a single-chain variable fragment (scFv) sequence derived from the EBOV GP-specific mAb KZ52. Fusions were done in four configurations: to the N- or C-terminus of the IgG heavy chain [HC] or light chain [LC] in FIG. 5B, bsAbs and IgGs were expressed in 293-Freestyle cells by co-transfection of HC and LC expression vectors, and purified by protein A affinity chromatography. In FIG. 5C, it is shown that bsAbs, but not NPC1-specific IgGs, can simultaneously bind to GP and NPC1 domain C. bsAbs and IgGs were captured onto GP-coated ELISA plates and then incubated with NPC1 domain C-flag. Bound NPC1 domain C was detected with an anti-flag antibody.

It was postulated that the NPC1-specific mAbs do not neutralize EBOV entry because they cannot efficiently access NPC1-containing late endosomes. To overcome this obstacle, an exploratory panel of bispecific antibodies (bsAbs) containing both NPC1-binding (401 or 548) and GP-binding (KZ52) specificities was generated. It was reasoned that one or more of these bsAbs might be able to 'ride' virus particles into late endosomes and then bind to NPC1, thereby inhibiting viral entry by both GP-blocking and receptor-blocking mechanisms. It was found that all four purified bsAbs could bind simultaneously to EBOV GP and NPC1 (e.g., see FIG. 5C), setting the stage for infection neutralization studies.

Figure 6:
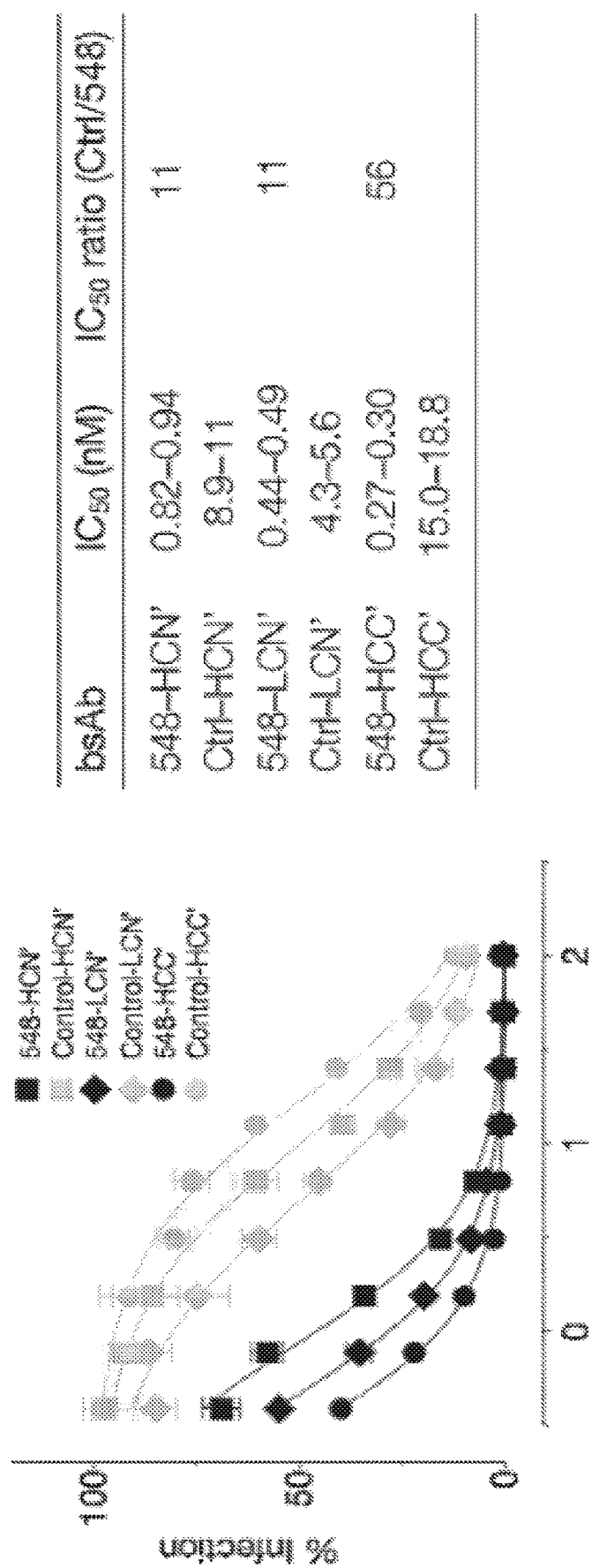
FIG. 6. GP-NPC1 bsAbs neutralize VSV-EBOV GP infection with enhanced potency. Left panel, GP-NPC1 bsAbs show enhanced potency at viral neutralization relative to control GP-only bsAbs. VSV-EBOV GP particles were pre-incubated with the indicated concentrations of each bsAb for 1 h at room temp and then allowed to infect U2OS cells. Infected cells were quantified at 16 h post-infection and normalized to a no-antibody control (100%). Right panel, the neutralization curves were fit to a logistic equation to extract the concentration of half-maximal neutralization ($IC_{50}\pm95\%$ confidence intervals).

As shown in FIG. 6, GP-NPC1 bsAbs neutralize VSV-EBOV GP infection with enhanced potency. In the left panel, GP-NPC1 bsAbs show enhanced potency at viral neutralization relative to control GP-only hsAbs. VSV-EBOV GP particles were pre-incubated with the indicated concentrations of each bsAb for 1 hour at room temperature and then allowed to infect U2OS cells. Infected cells were quantified at 16 hours post-infection and normalized to a no-antibody control (100%). In the right panel, the neutralization curves were fit to a logistic equation to extract the concentration of half-maximal neutralization ($IC_{50} \pm 95\%$ confidence intervals). The GP-NPC1 bsAbs were 10-60 fold more potent at neutralizing EBOV entry than control bsAbs in which an irrelevant (non-NPC1 binding) IgG was fused to the same scFv, derived from the OP-specific mAb, KZ52. These results indicate that the bsAbs possess an enhanced capacity to block GP-NPC1 binding within endosomes, relative to the NPC1-specific IgGs.

As shown in FIG. 6, the enhanced neutralization potency of GP-NPC1 bsAbs can be attributed to their receptor blocking activity. In the left panel, VSV-EBOV GP particles were pre-incubated with the indicated concentrations of each bsAb for 1 hour at room temperature and then allowed to infect matched U2OS cell lines expressing endogenous levels of NPC1 or over-expressing NPC1 ($NPC1^{hi}$). Infected cells were quantified at 16 hours post-infection and normalized to a no-antibody control (100%). In the right panel, the neutralization curves were fit to a logistic equation to extract the concentration of half-maximal neutralization ($IC_{50} \pm 95\%$ confidence intervals). The ratio of $IC_{50}$s for each bsAb in $NPC1^{hi}$ vs. WT U2OS cells is shown. It was reasoned that the neutralization potency of GP-NPC1 bsAbs should be reduced in cells engineered to overexpress NPC1, because the excess NPC1 should titrate the avail e NPC1-binding sites in the bsAbs and thereby increase the probability of productive GP-NPC1 binding. This is precisely what was observed. The bsAb 548-HCN' suffered a 24-fold loss in potency in U2OS—$NPC1^{hi}$ cells, relative to WT U2OS cells. By contrast, the potency of the Ctrl-HCN' bsAb, which cannot bind to NPC1, was reduced much more modestly (~2-fold). These findings provide strong evidence that the bsAbs neutralize viral infection by deploying both GP- and NPC1-binding specificities within cells.

Figure 7:
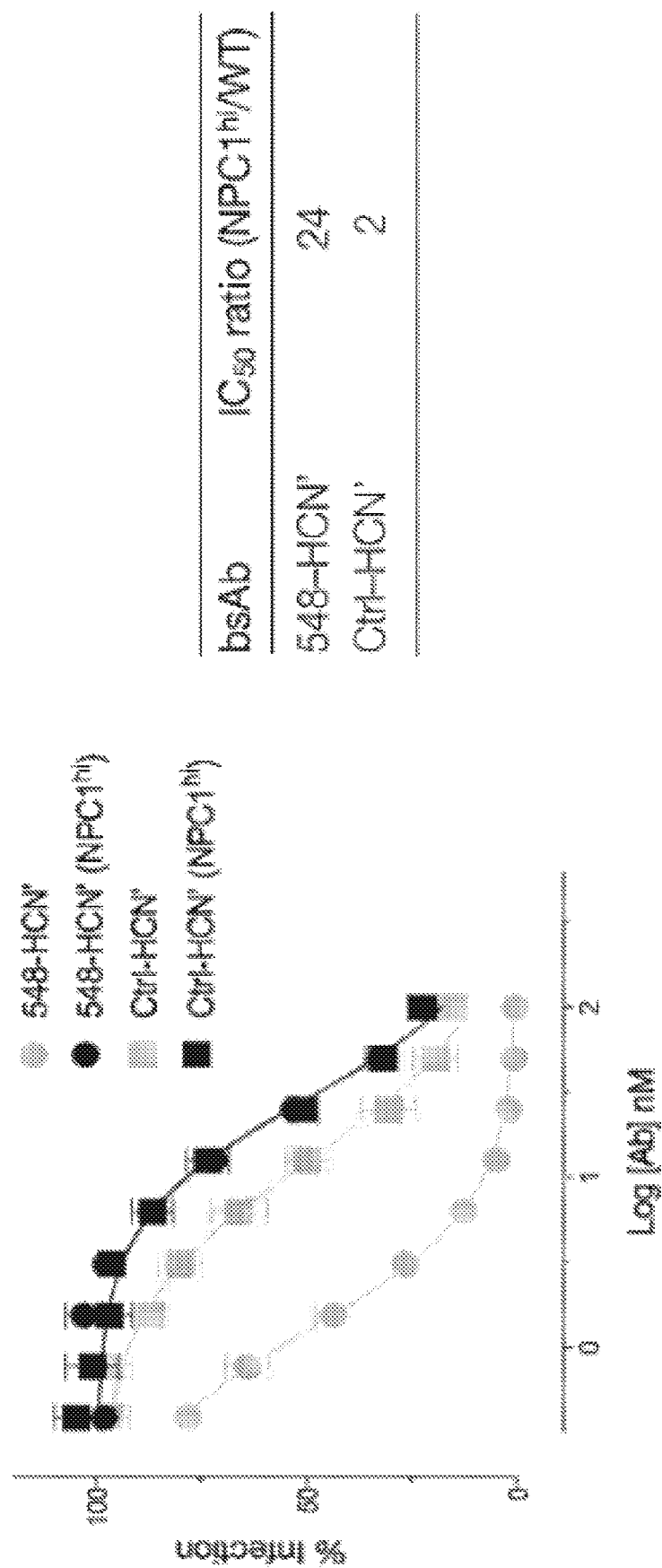
FIG. 7. The enhanced neutralization potency of GP-NPC1 bsAbs can be attributed to their receptor blocking activity. Left panel, VSV-EBOV GP particles were pre-incubated with the indicated concentrations of each bsAb for 1 h at room temp and then allowed to infect matched U2OS cell lines expressing endogenous levels of NPC1 or over-expressing NPC1 ($NPC1^{hi}$). Infected cells were quantified at 16 h post-infection and normalized to a no-antibody control (100%). Right panel, the neutralization curves were fit to a logistic equation to extract the concentration of half-maximal neutralization ($IC_{50}\pm95\%$ confidence intervals). The ratio of $IC_{50}$s for each bsAb in $NPC1^{hi}$ vs. WT U2OS cells is shown.
Figure 8:
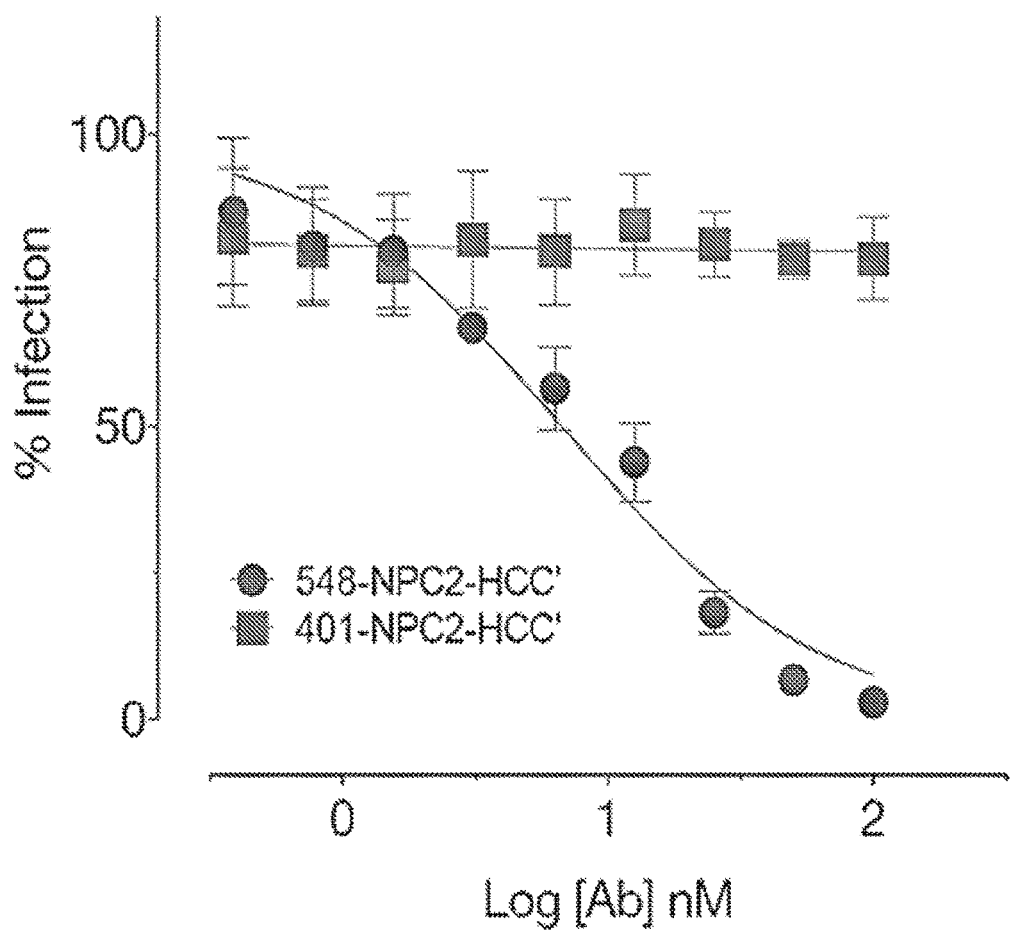
FIG. 8. Fusion of a receptor-blocking IgG to a late endosome-localizing protein facilitates viral neutralization. bsAbs comprising an NPC1-specific IgG (401 or 548) fused to NPC2, a soluble late endosomal/lysosomal protein, were expressed and purified, and examined for their capacity to neutralize VSV-EBOV OP infection, as described in FIGS. 6-7.
Figure 9A:
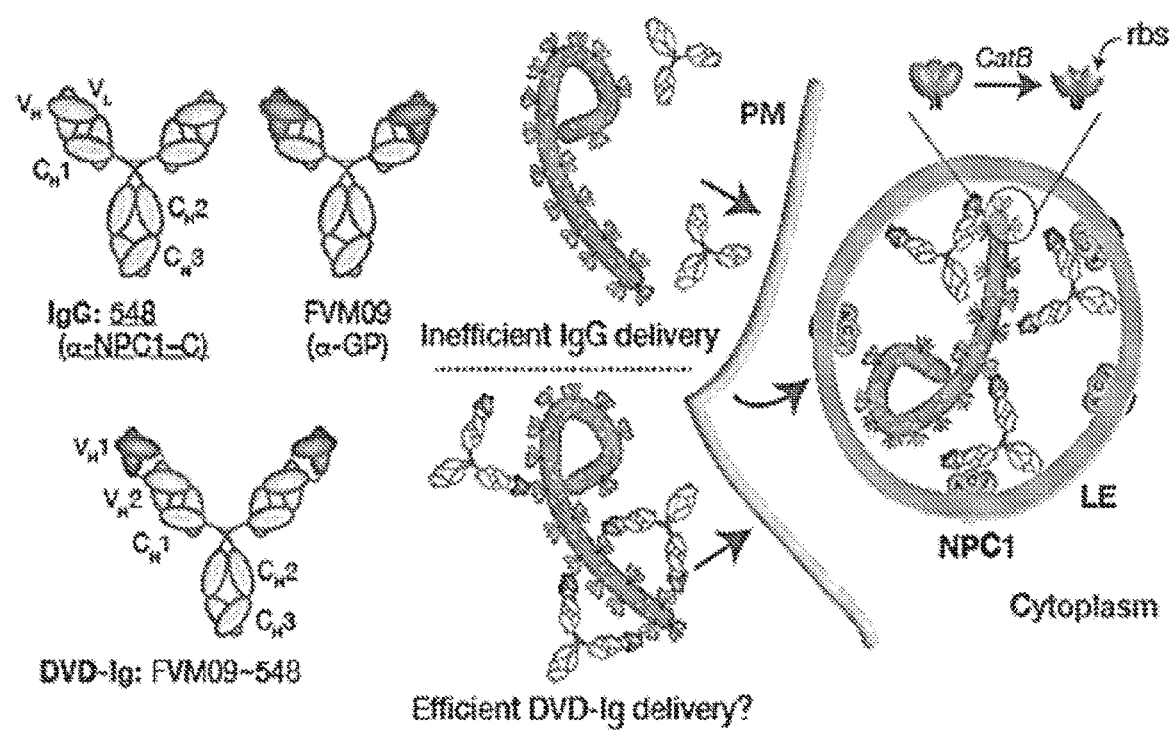
Figure 10A:
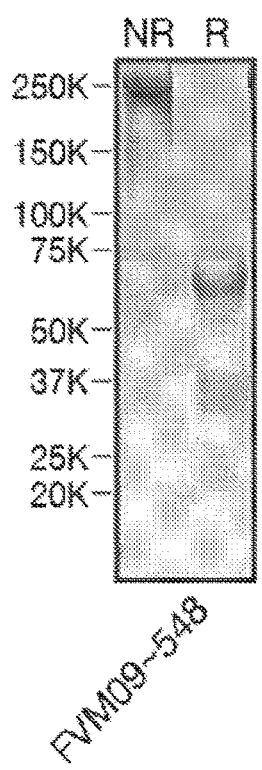
FIG. 10A-10B. A shows an SDS-polyacrylamide gel of purified FVM09~548 resolved under non-reducing (NR) and reducing (R) conditions and stained with Commassie Brilliant Blue. In B, FVM09~548 was subjected to size-exclusion chromatography coupled to multi-angle light scattering (SEC-MALS). The SEC-MALS trace indicates that the majority species of FVM09~548 (main peak; retention time=5.10 min) is an IgG-like monomer with an apparent molecular weight of ~175 kDa. A small (typical) amount of soluble aggregates (retention team=4.46 min) is also present.
Figure 10B:
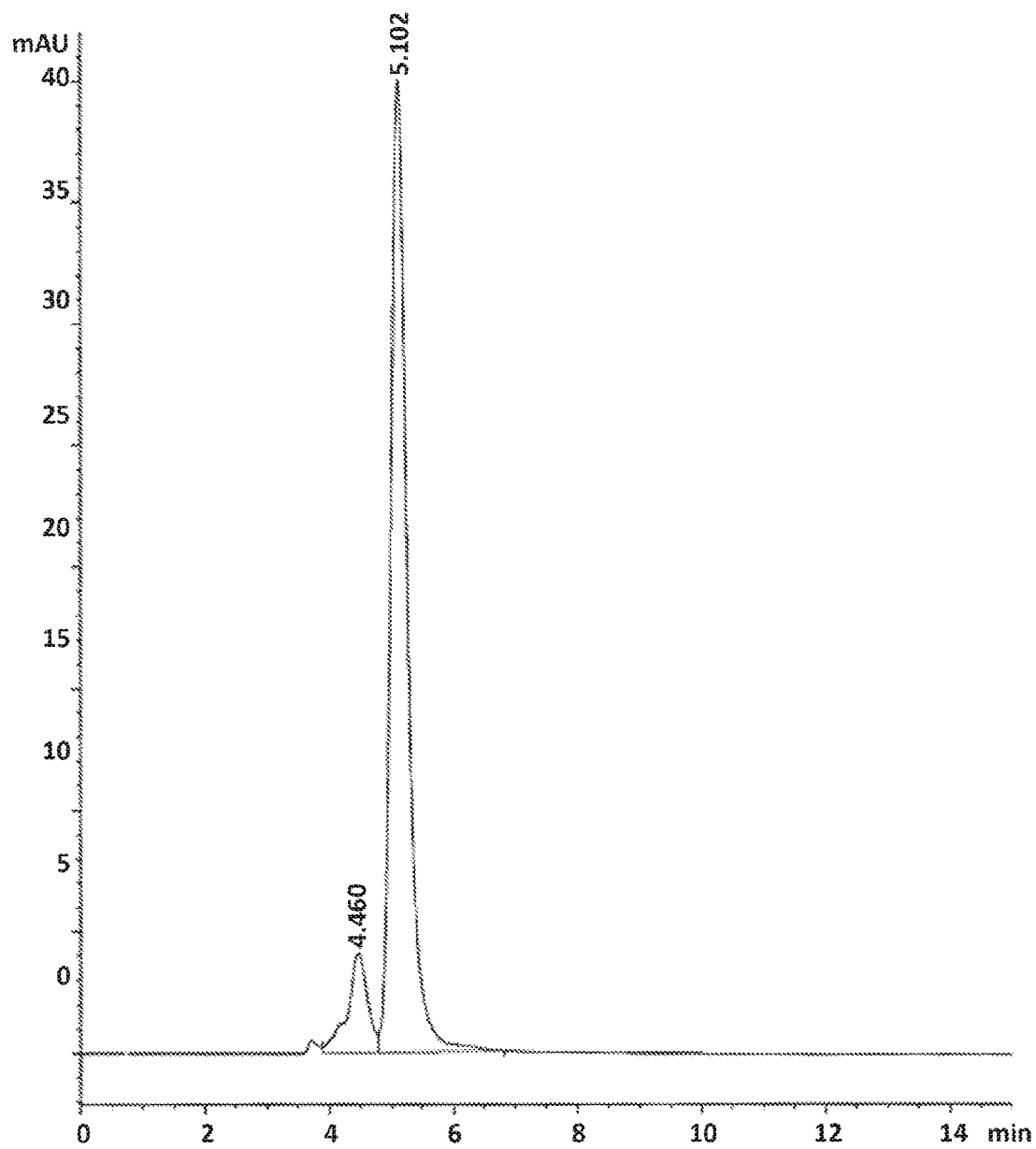
Figure 11A:
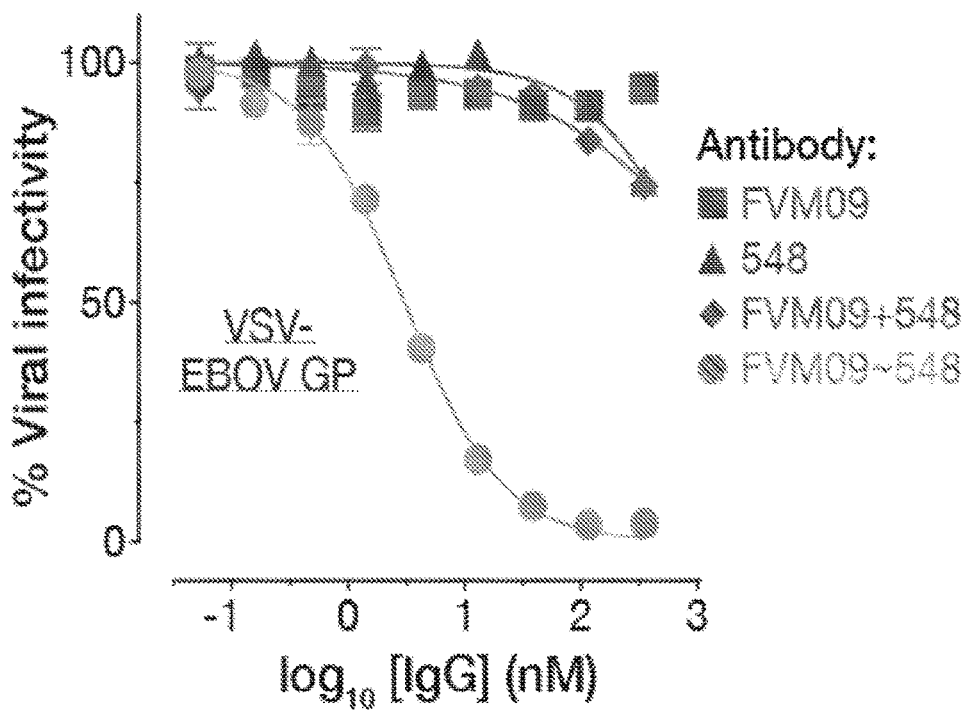
Figure 11B:
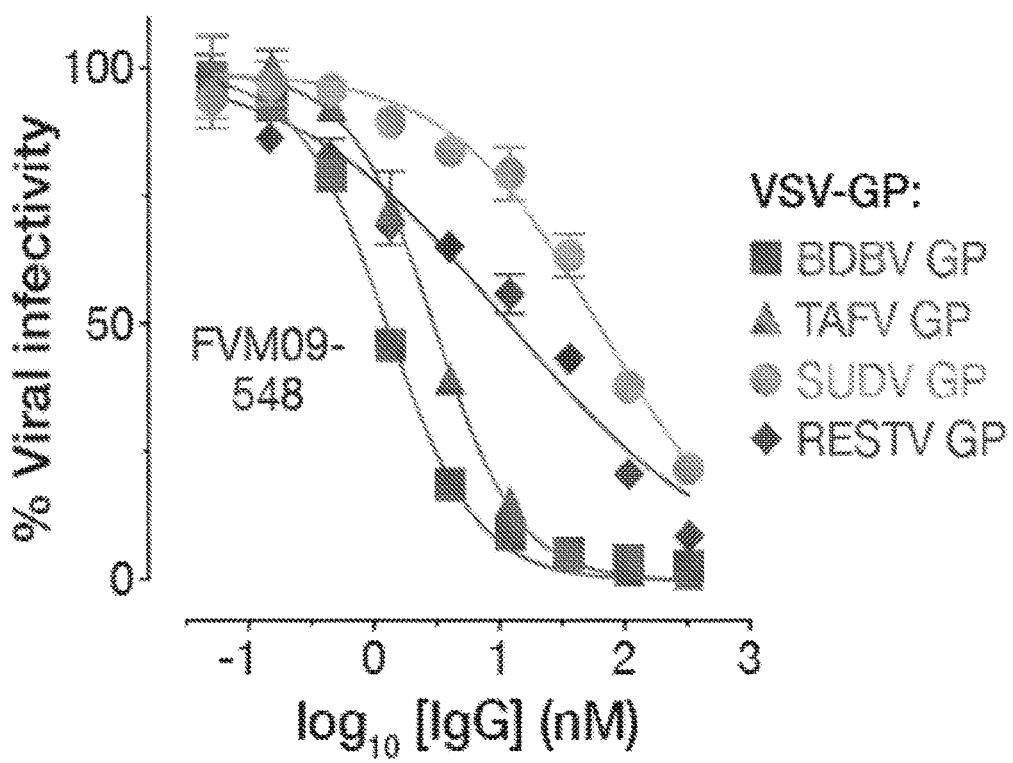
Figure 12C:
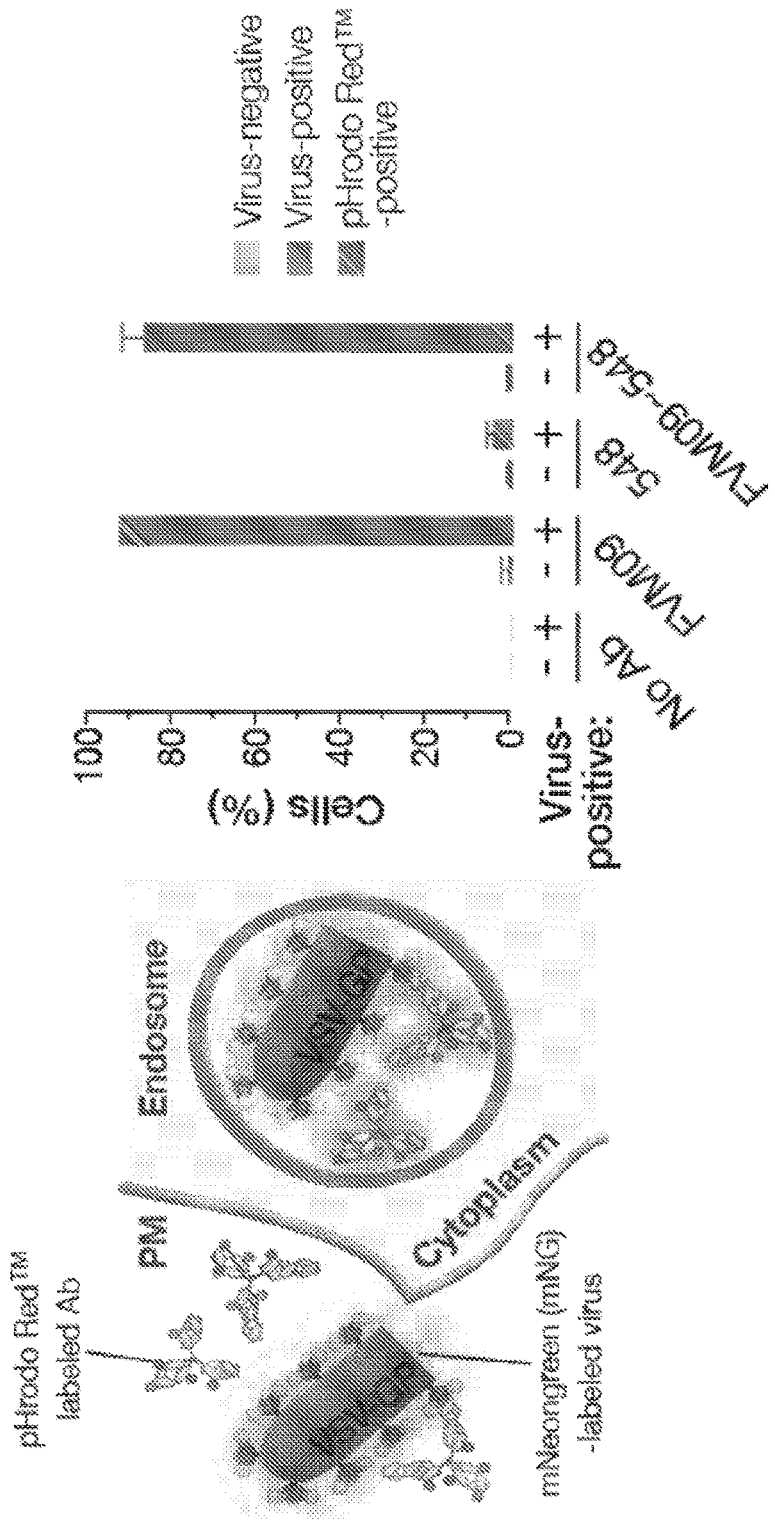
Figure 13A:
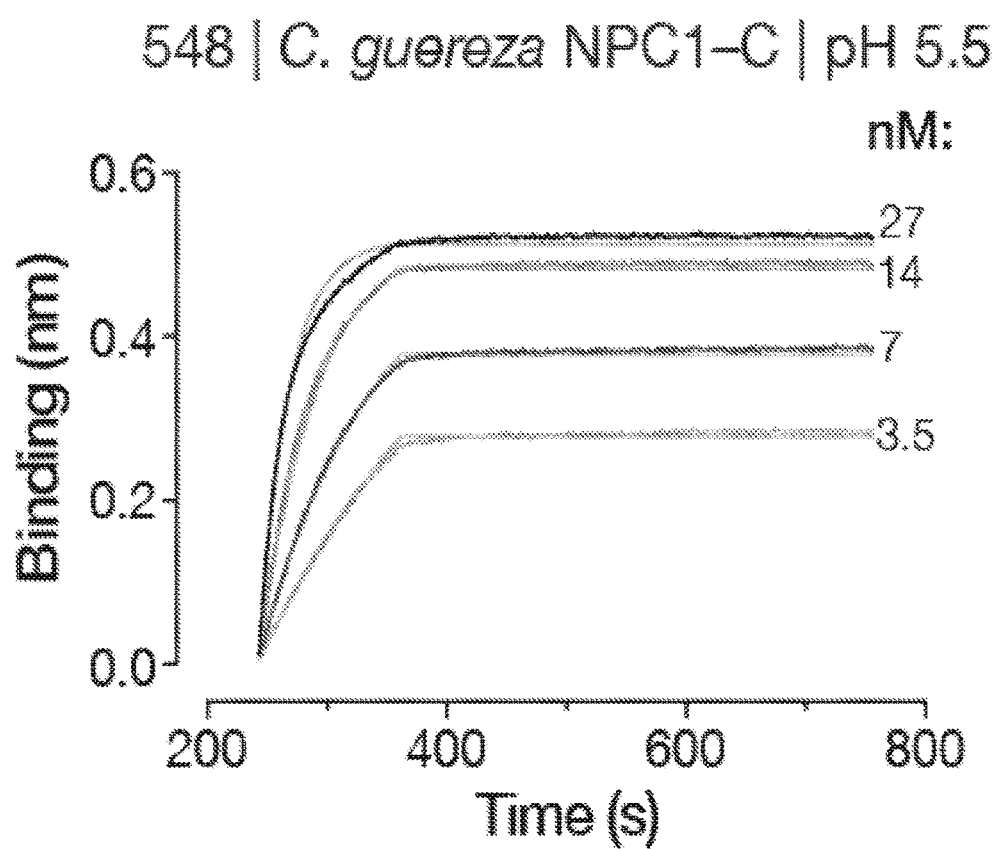

An additional strategy to deliver NPC1-specific IgGs to NPC1-positive late endosomes was also developed. The IgGs were fused to NPC2, a late endosomalilysosomal host protein that interacts with NPC1 and that can autonomously traffic to late endosomes when added to cells (Naureckiene, Science 2000). As shown in FIG. 8, fusion of a receptor-blocking IgG to a late endosome-localizing protein facilitates viral neutralization. bsAbs comprising an NPC1-specific IgG (401 or 548) fused to NPC2, a soluble late endosomalllysosomal protein, were expressed and purified, and examined for their capacity to neutralize VSV-EBOV GP infection, as described in FIGS. 6-7. Fusion of the potent receptor-blocking IgG 548 to NPC2 afforded neutralization of infection, whereas fusion of the weak receptor-blocking IgG 401 to NPC2 did not. Therefore, direct, cellular protein-mediated delivery of NPC1-specific IgGs to NPC1+ endosomes is also a feasible strategy for targeting NPC1 and preventing NPC1-mediated filovirus entry into cells.

The NPC1-targeting bispecific antibody approaches described herein provide an unprecedented opportunity for anti-filovirus therapeutics with increased antiviral breadth.

REFERENCES

Brummelkamp T R, Chandran K. Ebola virus entry requires the host-programmed recognition of an intracellular receptor. EMBO J 31:1947-1960, 2012.

Carette, J. E., Raaben, M., Wong, A. C., Herbert, A. S., Obemosterer, G., Mulherkar, N., Kuehne, A. I., Kranzusch, P. J., Griffin, A. M., Ruthel, G., et al. Ebola virus entry requires the cholesterol transporter Niemann-Pick C1. Nature 477: 340-343, 2011.

Davies J P, Ioannou Y A. Topological analysis of Niemann-Pick C1 protein reveals that the membrane orientation of the putative sterol-sensing domain is identical to those of 3-hydroxy-3-methylglutaryl-CoA reductase and sterol regulatory element binding protein cleavage-activating protein. J Biol Chem. 275(32):24367-74, 2000.

Keck Z Y, et al. Macaque Monoclonal Antibodies Targeting Novel Conserved Epitopes within Filovirus Glycoprotein. J Virol 90:279-91, 2015.

Miller E H, Obemosterer G, Raaben M, Herbert A S, Deffieu M, Krishnan A, Ndungo E, Sandesara R G, Carette J E, Kuehne A I, Ruthel G, Pfeffer S R, Dye J M, Whelan S P, Naureckiene S, Sleat D E, Lackland H, Fensom A, Vanier M T, Wattiaux R, Jadot M, Lobel P. Identification of HE1 as the second gene of Niemann-Pick C disease. Science. 290:2298-2301, 2000.

Negredo A, Palacios G, Vazquez-Morón S, González F, Dopazo H, Molero F, Juste J, Quetglas J, Savji N, de la Cruz Martinez M, Herrera J E, Pizarro M, Hutchison S K, Echevarria J E, Lipkin W I, Tenorio A. Discovery of an ebolavirus-like filovirus in europe. PLoS Pathos. 7:e1002304, 2011.

Ng M, Ndungo E, Jangra R K, Cai Y, Postnikova E, Radoshitzky S R, Dye J M, Ramirez de Arellano E, Negredo A, Palacios G, Kuhn J H, Chandran K. 2014. Cell entry by a novel European filovirus requires host endosomal cysteine proteases and Niemann-Pick C1. Virology. 468-470:637-646, 2014.

Qiu X, Wong G, Audet J, Bello A, Fernando L, Alimonti J B, Fausther-Bovendo H, Wei H, Aviles J, Hiatt E, Johnson A, Morton J, Swope K, Bohorov O, Bohorova N, Goodman C, Kim D, Pauly M H, Velasco J, Pettitt J, Olinger G G, Whaley K, Xu B, Strong J E, Zeitlin L, Kobinger G P. 2014. Reversion of advanced Ebola virus disease in nonhuman primates with ZMapp. Nature. 514:47-53, 2014.

Wu C, Ying H, Grinnell C, Bryant S, Miller R. Clabbers A et al. Simultaneous targeting of multiple disease mediators by a dual variable-domain immunoglobulin. Nat Biotechnol 25:1290-1297, 2007.

---

What is claimed is:

1. A method of treating or preventing or reducing or inhibiting a filovirus infection in a subject comprising administering to the subject a monoclonal antibody or fragment thereof that binds to Niemann-Pick C1 (NPC1) receptor in an amount effective to treat or prevent or reduce or inhibit a filovirus infection in a subject, wherein the antibody or fragment thereof comprises:

a variable region of a light chain that comprises the amino acid sequence set forth in SEQ ID NO:3 and a variable region of a heavy chain that comprises the amino acid sequence set forth in SEQ ID NO:4; or a variable region of a light chain that comprises the amino acid sequence set forth in SEQ ID NO:5 and a variable region of a heavy chain that comprises the amino acid sequence set forth in SEQ ID NO:6; or a variable region of a light chain that comprises the amino acid sequence set forth in SEQ ID NO:7 and a variable region of a heavy chain that comprises the amino acid sequence set forth in SEQ ID NO:8.

2. The method of claim 1, wherein the monoclonal antibody is provided in a bispecific antibody or bispecific fusion construct comprising (i) the antibody or fragment of claim 1 and (ii) an antibody or fragment that binds to an Ebola virus, wherein the antibody or fragment that binds to the Ebola virus is monoclonal antibody KZ52 or a single-chain variable fragment (scFv) sequence derived from monoclonal antibody KZ52.

3. The method of claim 2, wherein a NPC1-specific sequence is fused to a single-chain variable fragment (scFv) sequence derived from EBOV GP-specific monoclonal antibody KZ52.

4. The method of claim 3, wherein fusion is to a N- or C-terminus of an IgG heavy chain or light chain.

5. The method of claim 1, wherein the monoclonal antibody is provided in a fusion construct comprising the antibody or fragment of claim 1 fused to Niemann-Pick C2 (NPC2).

6. The method of claim 2, wherein the bispecific antibody comprises heavy and light chains of a NPC1-specific sequence fused to variable VH and VL domains of KZ52 to generate a dual-variable domain Ig.

7. The method of claim 2, wherein the bispecific antibody comprises the amino acid sequence set forth in any one of SEQ ID NOs:9-20.

8. The method of claim 5, wherein the bispecific fusion construct comprises the amino acid sequence set forth in SEQ ID NO:21 or SEQ ID NO:22.

9. The method of claim 1, wherein the subject is infected with a filovirus.

10. The method of claim 1, wherein the subject is at risk for infection with a filovirus.

11. The method of claim 10, wherein the subject is a family member or healthcare worker in an area of an outbreak of a filovirus infection.

12. The method of claim 10, wherein the subject is a medical personnel, first responder or military personnel potentially exposed or exposed to a filovirus as the result of bioterrorism or biological warfare.

13. The method of claim 10, wherein the subject is a biosafety level 3/4 laboratory personnel or animal worker potentially exposed or exposed to a filovirus.

14. The method of claim 1, wherein the filovirus is an Ebola virus.

15. The method of claim 14, wherein the Ebola virus species is *Zaire ebolavirus* or *Sudan ebolavirus*.

16. The method of claim 1, wherein the filovirus is a Marburg virus, a Bundibugyo virus, a Sudan virus, a Ravn virus or a Lloviu virus.

17. The method of claim 1, wherein the subject is a mammal.

18. The method of claim 1, wherein the subject is a human.

\* \* \* \* \*

SEQUENCE LISTING

<160> NUMBER OF SEQ ID NOS: 27

<210> SEQ ID NO 1
<211> LENGTH: 1278
<212> TYPE: PRT
<213> ORGANISM: Homo sapiens

<400> SEQUENCE: 1

```
Met Thr Ala Arg Gly Leu Ala Leu Gly Leu Leu Leu Leu Leu Leu Cys
1               5                   10                  15

Pro Ala Gln Val Phe Ser Gln Ser Cys Val Trp Tyr Gly Glu Cys Gly
            20                  25                  30

Ile Ala Tyr Gly Asp Lys Arg Tyr Asn Cys Glu Tyr Ser Gly Pro Pro
        35                  40                  45

Lys Pro Leu Pro Lys Asp Gly Tyr Asp Leu Val Gln Glu Leu Cys Pro
    50                  55                  60

Gly Phe Phe Phe Gly Asn Val Ser Leu Cys Cys Asp Val Arg Gln Leu
65                  70                  75                  80

Gln Thr Leu Lys Asp Asn Leu Gln Leu Pro Leu Gln Phe Leu Ser Arg
                85                  90                  95

Cys Pro Ser Cys Phe Tyr Asn Leu Leu Asn Leu Phe Cys Glu Leu Thr
            100                 105                 110

Cys Ser Pro Arg Gln Ser Gln Phe Leu Asn Val Thr Ala Thr Glu Asp
        115                 120                 125

Tyr Val Asp Pro Val Thr Asn Gln Thr Lys Thr Asn Val Lys Glu Leu
    130                 135                 140

Gln Tyr Tyr Val Gly Gln Ser Phe Ala Asn Ala Met Tyr Asn Ala Cys
145                 150                 155                 160

Arg Asp Val Glu Ala Pro Ser Ser Asn Asp Lys Ala Leu Gly Leu Leu
                165                 170                 175

Cys Gly Lys Asp Ala Asp Ala Cys Asn Ala Thr Asn Trp Ile Glu Tyr
            180                 185                 190

Met Phe Asn Lys Asp Asn Gly Gln Ala Pro Phe Thr Ile Thr Pro Val
        195                 200                 205

Phe Ser Asp Phe Pro Val His Gly Met Glu Pro Met Asn Asn Ala Thr
    210                 215                 220

Lys Gly Cys Asp Glu Ser Val Asp Glu Val Thr Ala Pro Cys Ser Cys
225                 230                 235                 240

Gln Asp Cys Ser Ile Val Cys Gly Pro Lys Pro Gln Pro Pro Pro Pro
                245                 250                 255

Pro Ala Pro Trp Thr Ile Leu Gly Leu Asp Ala Met Tyr Val Ile Met
            260                 265                 270

Trp Ile Thr Tyr Met Ala Phe Leu Leu Val Phe Phe Gly Ala Phe Phe
        275                 280                 285
```

```
Ala Val Trp Cys Tyr Arg Lys Arg Tyr Phe Val Ser Glu Tyr Thr Pro
290                 295                 300
Ile Asp Ser Asn Ile Ala Phe Ser Val Asn Ala Ser Asp Lys Gly Glu
305                 310                 315                 320
Ala Ser Cys Cys Asp Pro Val Ser Ala Ala Phe Glu Gly Cys Leu Arg
                325                 330                 335
Arg Leu Phe Thr Arg Trp Gly Ser Phe Cys Val Arg Asn Pro Gly Cys
            340                 345                 350
Val Ile Phe Phe Ser Leu Val Phe Ile Thr Ala Cys Ser Ser Gly Leu
        355                 360                 365
Val Phe Val Arg Val Thr Thr Asn Pro Val Asp Leu Trp Ser Ala Pro
370                 375                 380
Ser Ser Gln Ala Arg Leu Glu Lys Glu Tyr Phe Asp Gln His Phe Gly
385                 390                 395                 400
Pro Phe Phe Arg Thr Glu Gln Leu Ile Ile Arg Ala Pro Leu Thr Asp
                405                 410                 415
Lys His Ile Tyr Gln Pro Tyr Pro Ser Gly Ala Asp Val Pro Phe Gly
            420                 425                 430
Pro Pro Leu Asp Ile Gln Ile Leu His Gln Val Leu Asp Leu Gln Ile
        435                 440                 445
Ala Ile Glu Asn Ile Thr Ala Ser Tyr Asp Asn Glu Thr Val Thr Leu
450                 455                 460
Gln Asp Ile Cys Leu Ala Pro Leu Ser Pro Tyr Asn Thr Asn Cys Thr
465                 470                 475                 480
Ile Leu Ser Val Leu Asn Tyr Phe Gln Asn Ser His Ser Val Leu Asp
                485                 490                 495
His Lys Lys Gly Asp Asp Phe Phe Val Tyr Ala Asp Tyr His Thr His
            500                 505                 510
Phe Leu Tyr Cys Val Arg Ala Pro Ala Ser Leu Asn Asp Thr Ser Leu
        515                 520                 525
Leu His Asp Pro Cys Leu Gly Thr Phe Gly Gly Pro Val Phe Pro Trp
530                 535                 540
Leu Val Leu Gly Gly Tyr Asp Asp Gln Asn Tyr Asn Asn Ala Thr Ala
545                 550                 555                 560
Leu Val Ile Thr Phe Pro Val Asn Asn Tyr Tyr Asn Asp Thr Glu Lys
                565                 570                 575
Leu Gln Arg Ala Gln Ala Trp Glu Lys Glu Phe Ile Asn Phe Val Lys
            580                 585                 590
Asn Tyr Lys Asn Pro Asn Leu Thr Ile Ser Phe Thr Ala Glu Arg Ser
        595                 600                 605
Ile Glu Asp Glu Leu Asn Arg Glu Ser Asp Ser Asp Val Phe Thr Val
610                 615                 620
Val Ile Ser Tyr Ala Ile Met Phe Leu Tyr Ile Ser Leu Ala Leu Gly
625                 630                 635                 640
His Met Lys Ser Cys Arg Arg Leu Leu Val Asp Ser Lys Val Ser Leu
                645                 650                 655
Gly Ile Ala Gly Ile Leu Ile Val Leu Ser Ser Val Ala Cys Ser Leu
            660                 665                 670
Gly Val Phe Ser Tyr Ile Gly Leu Pro Leu Thr Leu Ile Val Ile Glu
        675                 680                 685
Val Ile Pro Phe Leu Val Leu Ala Val Gly Val Asp Asn Ile Phe Ile
690                 695                 700
```

-continued

Leu Val Gln Ala Tyr Gln Arg Asp Glu Arg Leu Gln Gly Glu Thr Leu
705                 710                 715                 720

Asp Gln Gln Leu Gly Arg Val Leu Gly Glu Val Ala Pro Ser Met Phe
            725                 730                 735

Leu Ser Ser Phe Ser Glu Thr Val Ala Phe Phe Leu Gly Ala Leu Ser
            740                 745                 750

Val Met Pro Ala Val His Thr Phe Ser Leu Phe Ala Gly Leu Ala Val
        755                 760                 765

Phe Ile Asp Phe Leu Leu Gln Ile Thr Cys Phe Val Ser Leu Leu Gly
    770                 775                 780

Leu Asp Ile Lys Arg Gln Glu Lys Asn Arg Leu Asp Ile Phe Cys Cys
785                 790                 795                 800

Val Arg Gly Ala Glu Asp Gly Thr Ser Val Gln Ala Ser Glu Ser Cys
            805                 810                 815

Leu Phe Arg Phe Phe Lys Asn Ser Tyr Ser Pro Leu Leu Leu Lys Asp
            820                 825                 830

Trp Met Arg Pro Ile Val Ile Ala Ile Phe Val Gly Val Leu Ser Phe
        835                 840                 845

Ser Ile Ala Val Leu Asn Lys Val Asp Ile Gly Leu Asp Gln Ser Leu
850                 855                 860

Ser Met Pro Asp Asp Ser Tyr Met Val Asp Tyr Phe Lys Ser Ile Ser
865                 870                 875                 880

Gln Tyr Leu His Ala Gly Pro Pro Val Tyr Phe Val Leu Glu Glu Gly
            885                 890                 895

His Asp Tyr Thr Ser Ser Lys Gly Gln Asn Met Val Cys Gly Gly Met
        900                 905                 910

Gly Cys Asn Asn Asp Ser Leu Val Gln Gln Ile Phe Asn Ala Ala Gln
    915                 920                 925

Leu Asp Asn Tyr Thr Arg Ile Gly Phe Ala Pro Ser Ser Trp Ile Asp
930                 935                 940

Asp Tyr Phe Asp Trp Val Lys Pro Gln Ser Ser Cys Cys Arg Val Asp
945                 950                 955                 960

Asn Ile Thr Asp Gln Phe Cys Asn Ala Ser Val Val Asp Pro Ala Cys
            965                 970                 975

Val Arg Cys Arg Pro Leu Thr Pro Glu Gly Lys Gln Arg Pro Gln Gly
            980                 985                 990

Gly Asp Phe Met Arg Phe Leu Pro Met Phe Leu Ser Asp Asn Pro Asn
        995                 1000                1005

Pro Lys Cys Gly Lys Gly Gly His Ala Ala Tyr Ser Ser Ala Val
    1010                1015                1020

Asn Ile Leu Leu Gly His Gly Thr Arg Val Gly Ala Thr Tyr Phe
    1025                1030                1035

Met Thr Tyr His Thr Val Leu Gln Thr Ser Ala Asp Phe Ile Asp
    1040                1045                1050

Ala Leu Lys Lys Ala Arg Leu Ile Ala Ser Asn Val Thr Glu Thr
    1055                1060                1065

Met Gly Ile Asn Gly Ser Ala Tyr Arg Val Phe Pro Tyr Ser Val
    1070                1075                1080

Phe Tyr Val Phe Tyr Glu Gln Tyr Leu Thr Ile Ile Asp Asp Thr
    1085                1090                1095

Ile Phe Asn Leu Gly Val Ser Leu Gly Ala Ile Phe Leu Val Thr
    1100                1105                1110

Met Val Leu Leu Gly Cys Glu Leu Trp Ser Ala Val Ile Met Cys

| | | | | | | | | | | |
|---|---|---|---|---|---|---|---|---|---|---|
| | | | | 1115 | | | | 1120 | | 1125 |
| Ala | Thr | Ile | Ala | Met | Val | Leu | Val | Asn | Met | Phe | Gly | Val | Met | Trp |
| | | 1130 | | | | | 1135 | | | | | 1140 | | |

Ala Thr Ile Ala Met Val Leu Val Asn Met Phe Gly Val Met Trp
        1130                1135                1140

Leu Trp Gly Ile Ser Leu Asn Ala Val Ser Leu Val Asn Leu Val
    1145                1150                1155

Met Ser Cys Gly Ile Ser Val Glu Phe Cys Ser His Ile Thr Arg
        1160                1165                1170

Ala Phe Thr Val Ser Met Lys Gly Ser Arg Val Glu Arg Ala Glu
    1175                1180                1185

Glu Ala Leu Ala His Met Gly Ser Ser Val Phe Ser Gly Ile Thr
    1190                1195                1200

Leu Thr Lys Phe Gly Gly Ile Val Val Leu Ala Phe Ala Lys Ser
    1205                1210                1215

Gln Ile Phe Gln Ile Phe Tyr Phe Arg Met Tyr Leu Ala Met Val
    1220                1225                1230

Leu Leu Gly Ala Thr His Gly Leu Ile Phe Leu Pro Val Leu Leu
    1235                1240                1245

Ser Tyr Ile Gly Pro Ser Val Asn Lys Ala Lys Ser Cys Ala Thr
    1250                1255                1260

Glu Glu Arg Tyr Lys Gly Thr Glu Arg Glu Arg Leu Leu Asn Phe
    1265                1270                1275

<210> SEQ ID NO 2
<211> LENGTH: 4827
<212> TYPE: DNA
<213> ORGANISM: Homo sapiens

<400> SEQUENCE: 2

```
gaagggcaac acgggaccct tgaagcgggg tcgcggcggc gccccagccc gggccaggga      60
gtcccggcag cggcacctcc cagaaagggc ggagccgacg acgccttctt ccttcctgac     120
cggcgcgcgc agcctgctgc cgcggtcagc gcctgctcct gctcctccgc tcctcctgcg     180
cggggtgctg aaacagcccg ggaagtagac gccgcctccg gggagcccaa ccagccgaac     240
gccgccggcg tcagcagcct tgcgcggcca cagcatgacc gctcgcggcc tggcccttgg     300
cctcctcctg ctgctactgt gtccagcgca ggtgttttca cagtcctgtg tttggtatgg     360
agagtgtgga attgcatatg gggacaagag gtacaattgc gaatattctg cccaccaaa     420
accattgcca aggatggat atgacttagt gcaggaactc tgtccaggat tcttctttgg     480
caatgtcagt ctctgttgtg atgttcggca gcttcagaca ctaaaagaca acctgcagct     540
gcctctacag tttctgtcca gatgtccatc ctgtttttat aacctactga acctgttttg     600
tgagctgaca tgtagccctc acagagtca gttttgaat gttacagcta ctgaagatta     660
tgttgatcct gttacaaacc agacgaaaac aaatgtgaaa gagttacaat actacgtcgg     720
acagagttt gccaatgcaa tgtacaatgc ctgccgggat gtggaggccc cctcaagtaa     780
tgacaaggcc ctgggactcc tgtgtgggaa ggacgctgac gcctgtaatg ccaccaactg     840
gattgaatac atgttcaata aggacaatgg acaggcacct tttaccatca ctcctgtgtt     900
ttcagatttt ccagtccatg ggatggagcc catgaacaat gccaccaaag ctgtgacga     960
gtctgtggat gaggtcacag caccatgtag ctgccaagac tgctcatttg tctgtggccc    1020
caagccccag cccccacctc ctcctgctcc ctggacgatc cttggcttgg acgccatgta    1080
tgtcatcatg tggatcacct acatggccgtt tttgcttgtg tttttttggag cattttttgc    1140
agtgtggtgc tacagaaaac ggtattttgt ctccgagtac actcccatcg atagcaatat    1200
```

```
agcttttcct gttaatgcaa gtgacaaagg agaggcgtcc tgctgtgacc ctgtcagcgc   1260
agcatttgag ggctgcttga ggcggctgtt cacacgctgg gggtcttct gcgtccgaaa    1320 ccctggctgt gtcattttct tctcgctggt cttcattact gcgtgttcgt caggcctggt   1380
gtttgtccgg gtcacaacca atccagttga cctctggtca gcccccagca gccaggctcg   1440
cctggaaaaa gagtactttg accagcactt tgggcctttc ttccggacgg agcagctcat   1500
catccgggcc cctctcactg acaaacacat ttaccagcca tacccttcgg gagctgatgt   1560 acccttgga cctccgcttg acatacagat actgcaccag gttcttgact tacaaatagc    1620
catcgaaaac attactgcct cttatgacaa tgagactgtg acacttcaag acatctgctt   1680
ggcccctctt tcaccgtata acacgaactg caccattttg agtgtgttaa attacttcca   1740
gaacagccat tccgtgctgg accacaagaa aggggacgac ttctttgtgt atgccgatta   1800
ccacacgcac tttctgtact gcgtacgggc tcctgcctct ctgaatgata caagtttgct   1860
ccatgaccct tgtctgggta cgtttggtgg accagtgttc ccgtggcttg tgttgggagg   1920
ctatgatgat caaaactaca ataacgccac tgcccttgtg attaccttcc ctgtcaataa   1980
ttactataat gatacagaga agctccagag ggcccaggcc tgggaaaaag agtttattaa   2040
ttttgtgaaa aactacaaga atcccaatct gaccatttcc ttcactgctg aacgaagtat   2100
tgaagatgaa ctaaatcgtg aaagtgacag tgatgtcttc accgttgtaa ttagctatgc   2160
catcatgttt ctatatattt ccctagcctt ggggcacatg aaaagctgtc gcaggcttct   2220
ggtggattcg aaggtctcac taggcatcgc gggcatcttg atcgtgctga gctcggtggc   2280
ttgctccttg ggtgtcttca gctacattgg gttgcccttg accctcattg tgattgaagt   2340
catcccgttc ctggtgctgg ctgttggagt ggacaacatc ttcattctgg tgcaggccta   2400
ccagagagat gaacgtcttc aaggggaaac cctggatcag cagctgggca gggtcctagg   2460
agaagtggct cccagtatgt tcctgtcatc cttttctgag actgtagcat ttttcttagg   2520
agcattgtcc gtgatgccag ccgtgcacac cttctctctc tttgcgggat tggcagtctt   2580
cattgacttt cttctgcaga ttacctgttt cgtgagtctc ttggggttag acattaaacg   2640
tcaagagaaa aatcggctag acatcttttg ctgtgtcaga ggtgctgaag atggaacaag   2700
cgtccaggcc tcagagagct gtttgtttcg cttcttcaaa aactcctatt ctccacttct   2760
gctaaaggac tggatgagac caattgtgat agcaatattt gtgggtgttc tgtcattcag   2820
catcgcagtc ctgaacaaag tagatattgg attggatcag tctctttcga tgccagatga   2880
ctcctacatg gtggattatt tcaaatccat cagtcagtac ctgcatgcgg gtccgcctgt   2940
gtactttgtc ctggaggaag ggcacgacta cacttcttcc aaggggcaga acatggtgtg   3000
cggcggcatg ggctgcaaca atgattccct ggtgcagcag atatttaacg cggcgcagct   3060
ggacaactat acccgaatag gcttcgcccc ctcgtcctgg atcgacgatt atttcgactg   3120
ggtgaagcca cagtcgtctt gctgtcgagt ggacaatatc actgaccagt tctgcaatgc   3180
ttcagtggtt gaccctgcct gcgttcgctg caggcctctg actccggaag gcaaacagag   3240
gcctcagggg ggagacttca tgagattcct gcccatgttc ctttcggata acccctaaccc   3300 caagtgtggc aaaggggac atgctgccta tagttctgca gttaacatcc tccttggcca    3360
tggcaccagg gtcggagcca cgtacttcat gacctaccac accgtgctgc agacctctgc   3420
tgactttatt gacgctctga agaaagcccg acttatagcc agtaatgtca ccgaaaccat   3480
gggcattaac ggcagtgcct accgagtatt tccttacagt gtgttttatg tcttctacga   3540
```

```
acagtacctg accatcattg acgacactat cttcaacctc ggtgtgtccc tgggcgcgat    3600
atttctggtg accatggtcc tcctgggctg tgagctctgg tctgcagtca tcatgtgtgc    3660
caccatcgcc atggtcttgg tcaacatgtt tggagttatg tggctctggg gcatcagtct    3720
gaacgctgta tccttggtca acctggtgat gagctgtggc atctccgtgg agttctgcag    3780
ccacataacc agagcgttca cggtgagcat gaaaggcagc cgcgtggagc gcgcggaaga    3840
ggcacttgcc cacatgggca gctccgtgtt cagtggaatc acacttacaa aatttggagg    3900
gattgtggtg ttggcttttg ccaaatctca aattttccag atattctact tcaggatgta    3960
tttggccatg gtcttactgg gagccactca cggattaata tttctccctg tcttactcag    4020
ttacataggg ccatcagtaa ataaagccaa aagttgtgcc actgaagagc gatacaaagg    4080
aacagagcgc gaacggcttc taaatttcta gccctctcgc agggcatcct gactgaactg    4140
tgtctaaggg tcggtcggtt taccactgga cgggtgctgc atcggcaagg ccaagttgaa    4200
caccggatgg tgccaaccat cggttgtttg gcagcagctt tgaacgtagc gcctgtgaac    4260
tcaggaatgc acagttgact tgggaagcag tattactaga tctggaggca accacaggac    4320
actaaacttc tcccagcctc ttcaggaaag aaacctcatt ctttggcaag caggaggtga    4380
cactagatgg ctgtgaatgt gatccgctca ctgacactct gtaaaggcca atcaatgcac    4440
tgtctgtctc tccttttagg agtaagccat cccacaagtt ctataccata ttttagtga    4500 cagttgaggt tgtagataca ctttataaca ttttatagtt aaagagctt tattaatgca    4560 ataaattaac tttgtacaca ttttatata aaaaacagc aagtgatttc agaatgttgt    4620
aggcctcatt agagcttggt ctccaaaaat ctgtttgaaa aaagcaacat gttcttcaca    4680
gtgttcccct agaaaggaag agatttaatt gccagttaga tgtggcatga aatgagggac    4740
aaagaaagca tctcgtaggt gtgtctactg ggttttaact tattttctt taataaaata    4800 cattgttttc ctaaaaaaaa aaaaaaa                                       4827
```

<210> SEQ ID NO 3
<211> LENGTH: 107
<212> TYPE: PRT
<213> ORGANISM: Mus musculus

<400> SEQUENCE: 3

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Val Glu Ala Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Thr Tyr Tyr Cys Gln His His Tyr Gly Ser Pro Trp
                85                  90                  95

Thr Phe Gly Gly Gly Thr Lys Leu Glu Ile Lys
            100                 105
```

<210> SEQ ID NO 4
<211> LENGTH: 112
<212> TYPE: PRT
<213> ORGANISM: Mus musculus

```
<400> SEQUENCE: 4

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Glu Tyr Asp Thr Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ser Arg Gly Tyr Tyr Trp Gly Arg Gly Thr Thr Leu Thr Val Ser Ser
            100                 105                 110

<210> SEQ ID NO 5
<211> LENGTH: 107
<212> TYPE: PRT
<213> ORGANISM: Mus musculus

<400> SEQUENCE: 5

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ile Tyr Tyr Cys Gln His His Tyr Gly Ser Pro Trp
                85                  90                  95

Ala Phe Gly Gly Gly Thr Lys Leu Glu Ile Lys
            100                 105

<210> SEQ ID NO 6
<211> LENGTH: 112
<212> TYPE: PRT
<213> ORGANISM: Mus musculus

<400> SEQUENCE: 6

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asp Gly Asn Thr Glu Tyr Val Pro Lys Phe
    50                  55                  60

Gln Gly Lys Ala Thr Ile Thr Ala Asp Thr Phe Ser Asn Thr Val Tyr
65                  70                  75                  80

Leu Gln Leu Ser Gly Leu Thr Ser Glu Asp Thr Ala Val Tyr Tyr Cys
                85                  90                  95

Ser Arg Gly Tyr Tyr Trp Gly Gln Gly Thr Thr Leu Thr Val Ser Ser
```

<210> SEQ ID NO 7
<211> LENGTH: 107
<212> TYPE: PRT
<213> ORGANISM: Mus musculus

<400> SEQUENCE: 7

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Val Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Ser Val Gln Ala
65                  70                  75                  80

Glu Asp Leu Ala Leu Tyr Tyr Cys Gln Gln His Tyr Thr Ser Pro Trp
                85                  90                  95

Thr Phe Gly Gly Gly Thr Lys Leu Glu Ile Lys
            100                 105

<210> SEQ ID NO 8
<211> LENGTH: 117
<212> TYPE: PRT
<213> ORGANISM: Mus musculus
<220> FEATURE:
<221> NAME/KEY: misc_feature
<222> LOCATION: (15)..(15)
<223> OTHER INFORMATION: Xaa can be any naturally occurring amino acid

<400> SEQUENCE: 8

Asp Val Gln Leu Gln Glu Ser Gly Pro Asp Leu Val Lys Pro Xaa Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Arg Leu Glu Trp
        35                  40                  45

Met Asp Tyr Ile His Tyr Ser Gly Ser Ile Asn Tyr Asn Pro Ser Leu
50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Trp Gly Ala Thr Gly Phe Asp Tyr Trp Gly Gln Gly Thr Thr
            100                 105                 110

Leu Thr Val Ser Ser
        115

<210> SEQ ID NO 9
<211> LENGTH: 710
<212> TYPE: PRT
<213> ORGANISM: Artificial Sequence
<220> FEATURE:
<223> OTHER INFORMATION: 401-scFv-KZ52-HCN (heavy chain N-terminal
      fusion) (human-mouse hybrid sequence)

<400> SEQUENCE: 9

Glu Val Gln Leu Leu Glu Ser Gly Gly Gly Leu Val Lys Pro Gly Gly

```
  1               5                   10                  15
Ser Leu Arg Leu Ser Cys Ala Ala Ser Gly Phe Thr Leu Ile Asn Tyr
                20                  25                  30

Arg Met Asn Trp Val Arg Gln Ala Pro Gly Lys Gly Leu Glu Trp Val
                35                  40                  45

Ser Ser Ile Ser Ser Ser Ser Tyr Ile His Tyr Ala Asp Ser Val
 50                  55                  60

Lys Gly Arg Phe Thr Ile Ser Arg Asp Asn Ala Glu Asn Ser Leu Tyr
 65                  70                  75                  80

Leu Gln Met Asn Ser Leu Arg Ala Glu Asp Thr Ala Val Tyr Tyr Cys
                85                  90                  95

Val Arg Glu Gly Pro Arg Ala Thr Gly Tyr Ser Met Ala Asp Val Phe
                100                 105                 110

Asp Ile Trp Gly Gln Gly Thr Met Val Thr Val Ser Ser Gly Gly Gly
                115                 120                 125

Gly Ser Gly Gly Gly Gly Ser Gly Gly Gly Gly Ser Glu Leu Val Met
 130                 135                 140

Thr Gln Ser Pro Asp Ser Leu Ala Val Ser Leu Gly Glu Arg Ala Thr
 145                 150                 155                 160

Ile Asn Cys Lys Ser Ser Gln Ser Val Leu Tyr Ser Ser Asn Asn Lys
                165                 170                 175

Ser Tyr Leu Ala Trp Tyr Gln Gln Lys Pro Gly Gln Pro Pro Lys Leu
                180                 185                 190

Leu Ile Tyr Trp Ala Ser Thr Arg Glu Ser Gly Val Pro Asp Arg Phe
                195                 200                 205

Ser Gly Ser Gly Ser Gly Thr Asp Phe Thr Leu Thr Ile Ser Ser Leu
 210                 215                 220

Gln Ala Glu Asp Val Ala Val Tyr Tyr Cys Gln Gln Tyr Tyr Ser Ala
 225                 230                 235                 240

Pro Leu Thr Phe Gly Gly Gly Thr Lys Val Glu Ile Lys Gly Gly Ser
                245                 250                 255

Ala Gly Ser Ala Gly Ser Ala Gly Ser Gly Gly Ser Glu Val Gln Leu
                260                 265                 270

Gln Gln Ser Gly Ala Glu Leu Val Lys Pro Gly Ala Ser Val Lys Leu
 275                 280                 285

Ser Cys Thr Ala Ser Gly Phe Asn Ile Lys Asp Thr Tyr Met His Trp
 290                 295                 300

Val Lys Gln Arg Pro Glu Gln Gly Leu Glu Trp Ile Gly Arg Ile Asp
 305                 310                 315                 320

Pro Ala Asn Gly Asn Thr Glu Tyr Asp Thr Lys Phe Gln Gly Lys Ala
                325                 330                 335

Thr Ile Thr Ala Asp Thr Ser Ser Asn Thr Ala Tyr Leu Gln Leu Ser
                340                 345                 350

Ser Leu Thr Ser Glu Asp Thr Ala Val Tyr Tyr Cys Ser Arg Gly Tyr
                355                 360                 365

Tyr Trp Gly Arg Gly Thr Thr Leu Thr Val Ser Ser Ala Ser Thr Lys
 370                 375                 380

Gly Pro Ser Val Phe Pro Leu Ala Pro Ser Ser Lys Ser Thr Ser Gly
 385                 390                 395                 400

Gly Thr Ala Ala Leu Gly Cys Leu Val Lys Asp Tyr Phe Pro Glu Pro
                405                 410                 415

Val Thr Val Ser Trp Asn Ser Gly Ala Leu Thr Ser Gly Val His Thr
                420                 425                 430
```

```
Phe Pro Ala Val Leu Gln Ser Ser Gly Leu Tyr Ser Leu Ser Ser Val
            435                 440                 445

Val Thr Val Pro Ser Ser Ser Leu Gly Thr Gln Thr Tyr Ile Cys Asn
        450                 455                 460

Val Asn His Lys Pro Ser Asn Thr Lys Val Asp Lys Lys Val Glu Pro
465                 470                 475                 480

Lys Ser Cys Asp Lys Thr His Thr Cys Pro Pro Cys Pro Ala Pro Glu
                485                 490                 495

Leu Leu Gly Arg Pro Ser Val Phe Leu Phe Pro Pro Lys Pro Lys Asp
            500                 505                 510

Thr Leu Met Ile Ser Arg Thr Pro Glu Val Thr Cys Val Val Val Asp
        515                 520                 525

Val Ser His Glu Asp Pro Glu Val Lys Phe Asn Trp Tyr Val Asp Gly
    530                 535                 540

Val Glu Val His Asn Ala Lys Thr Lys Pro Arg Glu Glu Gln Tyr Asn
545                 550                 555                 560

Ser Thr Tyr Arg Val Val Ser Val Leu Thr Val Leu His Gln Asp Trp
                565                 570                 575

Leu Asn Gly Lys Glu Tyr Lys Cys Lys Val Ser Asn Lys Ala Leu Pro
            580                 585                 590

Ala Pro Ile Glu Lys Thr Ile Ser Lys Ala Lys Gly Gln Pro Arg Glu
        595                 600                 605

Pro Gln Val Tyr Thr Leu Pro Pro Ser Arg Glu Glu Met Thr Lys Asn
    610                 615                 620

Gln Val Ser Leu Thr Cys Leu Val Lys Gly Phe Tyr Pro Ser Asp Ile
625                 630                 635                 640

Ala Val Glu Trp Glu Ser Asn Gly Gln Pro Glu Asn Asn Tyr Lys Thr
                645                 650                 655

Thr Pro Pro Val Leu Asp Ser Asp Gly Ser Phe Phe Leu Tyr Ser Lys
            660                 665                 670

Leu Thr Val Asp Lys Ser Arg Trp Gln Gln Gly Asn Val Phe Ser Cys
        675                 680                 685

Ser Val Met His Glu Ala Leu His Asn His Tyr Thr Gln Lys Ser Leu
    690                 695                 700

Ser Leu Ser Pro Gly Lys
705                 710

<210> SEQ ID NO 10
<211> LENGTH: 482
<212> TYPE: PRT
<213> ORGANISM: Artificial Sequence
<220> FEATURE:
<223> OTHER INFORMATION: 401-scFv-KZ52-LCN (light chain N-terminal
      fusion) (human-mouse hybrid sequence)

<400> SEQUENCE: 10

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ile Asn Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Ser Tyr Ile His Tyr Ala Asp Ser Val
    50                  55                  60

Lys Gly Arg Phe Thr Ile Ser Arg Asp Asn Ala Glu Asn Ser Leu Tyr
```

```
               65                  70                  75                  80
        Leu Gln Met Asn Ser Leu Arg Ala Glu Asp Thr Ala Val Tyr Tyr Cys
                            85                  90                  95

Val Arg Glu Gly Pro Arg Ala Thr Gly Tyr Ser Met Ala Asp Val Phe
                           100                 105                 110

Asp Ile Trp Gly Gln Gly Thr Met Val Thr Val Ser Ser Gly Gly Gly
                       115                 120                 125

Gly Ser Gly Gly Gly Gly Ser Gly Gly Gly Gly Ser Glu Leu Val Met
                   130                 135                 140

Thr Gln Ser Pro Asp Ser Leu Ala Val Ser Leu Gly Glu Arg Ala Thr
        145                 150                 155                 160

Ile Asn Cys Lys Ser Ser Gln Ser Val Leu Tyr Ser Ser Asn Asn Lys
                           165                 170                 175

Ser Tyr Leu Ala Trp Tyr Gln Gln Lys Pro Gly Gln Pro Pro Lys Leu
                       180                 185                 190

Leu Ile Tyr Trp Ala Ser Thr Arg Glu Ser Gly Val Pro Asp Arg Phe
                   195                 200                 205

Ser Gly Ser Gly Ser Gly Thr Asp Phe Thr Leu Thr Ile Ser Ser Leu
                       210                 215                 220

Gln Ala Glu Asp Val Ala Val Tyr Tyr Cys Gln Gln Tyr Tyr Ser Ala
        225                 230                 235                 240

Pro Leu Thr Phe Gly Gly Gly Thr Lys Val Glu Ile Lys Gly Gly Ser
                           245                 250                 255

Ala Gly Ser Ala Gly Ser Ala Gly Ser Gly Gly Ser Asp Ile Gln Met
                       260                 265                 270

Thr Gln Ser Pro Ala Ser Leu Ser Ala Ser Val Gly Glu Thr Val Thr
                   275                 280                 285

Ile Thr Cys Arg Ala Ser Glu Asn Ile Tyr Ser Tyr Leu Ala Trp Tyr
                   290                 295                 300

Gln Gln Lys Gln Gly Lys Ser Pro Gln Leu Leu Val Tyr Asn Ala Lys
        305                 310                 315                 320

Thr Leu Val Glu Ala Val Pro Ser Arg Phe Ser Gly Ser Gly Ser Gly
                           325                 330                 335

Thr Gln Phe Ser Leu Lys Ile Asn Ser Leu Gln Pro Glu Asp Phe Gly
                       340                 345                 350

Thr Tyr Tyr Cys Gln His His Tyr Gly Ser Pro Trp Thr Phe Gly Gly
                   355                 360                 365

Gly Thr Lys Leu Glu Ile Lys Arg Thr Val Ala Ala Pro Ser Val Phe
                   370                 375                 380

Ile Phe Pro Pro Ser Asp Glu Gln Leu Lys Ser Gly Thr Ala Ser Val
        385                 390                 395                 400

Val Cys Leu Leu Asn Asn Phe Tyr Pro Arg Glu Ala Lys Val Gln Trp
                           405                 410                 415

Lys Val Asp Asn Ala Leu Gln Ser Gly Asn Ser Gln Glu Ser Val Thr
                       420                 425                 430

Glu Gln Asp Ser Lys Asp Ser Thr Tyr Ser Leu Ser Ser Thr Leu Thr
                   435                 440                 445

Leu Ser Lys Ala Asp Tyr Glu Lys His Lys Val Tyr Ala Cys Glu Val
                   450                 455                 460

Thr His Gln Gly Leu Ser Ser Pro Val Thr Lys Ser Phe Asn Arg Gly
        465                 470                 475                 480

Glu Cys
```

<210> SEQ ID NO 11
<211> LENGTH: 710
<212> TYPE: PRT
<213> ORGANISM: Artificial Sequence
<220> FEATURE:
<223> OTHER INFORMATION: 401-scFv-KZ52-HCC (heavy chain C-terminal fusion) (human-mouse hybrid sequence)

<400> SEQUENCE: 11

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Glu Tyr Asp Thr Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ser Arg Gly Tyr Tyr Trp Gly Arg Gly Thr Thr Leu Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Arg Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365
```

Pro Ser Asp Ile Ala Val Glu Trp Glu Ser Asn Gly Gln Pro Glu Asn
        370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys Gly Gly Ser Ala Gly Ser
        435                 440                 445

Ala Gly Ser Ala Gly Ser Gly Gly Ser Glu Val Gln Leu Leu Glu Ser
    450                 455                 460

Gly Gly Gly Leu Val Lys Pro Gly Gly Ser Leu Arg Leu Ser Cys Ala
465                 470                 475                 480

Ala Ser Gly Phe Thr Leu Ile Asn Tyr Arg Met Asn Trp Val Arg Gln
                485                 490                 495

Ala Pro Gly Lys Gly Leu Glu Trp Val Ser Ser Ile Ser Ser Ser Ser
            500                 505                 510

Ser Tyr Ile His Tyr Ala Asp Ser Val Lys Gly Arg Phe Thr Ile Ser
        515                 520                 525

Arg Asp Asn Ala Glu Asn Ser Leu Tyr Leu Gln Met Asn Ser Leu Arg
    530                 535                 540

Ala Glu Asp Thr Ala Val Tyr Tyr Cys Val Arg Glu Gly Pro Arg Ala
545                 550                 555                 560

Thr Gly Tyr Ser Met Ala Asp Val Phe Asp Ile Trp Gly Gln Gly Thr
                565                 570                 575

Met Val Thr Val Ser Ser Gly Gly Gly Ser Gly Gly Gly Gly Gly Ser
            580                 585                 590

Gly Gly Gly Gly Ser Glu Leu Val Met Thr Gln Ser Pro Asp Ser Leu
        595                 600                 605

Ala Val Ser Leu Gly Glu Arg Ala Thr Ile Asn Cys Lys Ser Ser Gln
    610                 615                 620

Ser Val Leu Tyr Ser Ser Asn Asn Lys Ser Tyr Leu Ala Trp Tyr Gln
625                 630                 635                 640

Gln Lys Pro Gly Gln Pro Pro Lys Leu Leu Ile Tyr Trp Ala Ser Thr
                645                 650                 655

Arg Glu Ser Gly Val Pro Asp Arg Phe Ser Gly Ser Gly Ser Gly Thr
            660                 665                 670

Asp Phe Thr Leu Thr Ile Ser Ser Leu Gln Ala Glu Asp Val Ala Val
        675                 680                 685

Tyr Tyr Cys Gln Gln Tyr Tyr Ser Ala Pro Leu Thr Phe Gly Gly Gly
    690                 695                 700

Thr Lys Val Glu Ile Lys
705                 710

<210> SEQ ID NO 12
<211> LENGTH: 482
<212> TYPE: PRT
<213> ORGANISM: Artificial Sequence
<220> FEATURE:
<223> OTHER INFORMATION: 401-scFv-KZ52-LCC (light chain C-terminal
      fusion) (human-mouse hybrid sequence)

<400> SEQUENCE: 12

Asp Ile Gln Met Thr Gln Ser Pro Ala Ser Leu Ser Ala Ser Val Gly

-continued

```
1               5                   10                  15
Glu Thr Val Thr Ile Thr Cys Arg Ala Ser Glu Asn Ile Tyr Ser Tyr
                20                  25                  30
Leu Ala Trp Tyr Gln Gln Lys Gln Gly Lys Ser Pro Gln Leu Leu Val
            35                  40                  45
Tyr Asn Ala Lys Thr Leu Val Glu Ala Val Pro Ser Arg Phe Ser Gly
        50                  55                  60
Ser Gly Ser Gly Thr Gln Phe Ser Leu Lys Ile Asn Ser Leu Gln Pro
65                  70                  75                  80
Glu Asp Phe Gly Thr Tyr Tyr Cys Gln His His Tyr Gly Ser Pro Trp
                85                  90                  95
Thr Phe Gly Gly Gly Thr Lys Leu Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
            195                 200                 205
Phe Asn Arg Gly Glu Cys Gly Gly Ser Ala Gly Ser Ala Gly Ser Ala
        210                 215                 220
Gly Ser Gly Gly Ser Glu Val Gln Leu Leu Glu Ser Gly Gly Gly Leu
225                 230                 235                 240
Val Lys Pro Gly Gly Ser Leu Arg Leu Ser Cys Ala Ala Ser Gly Phe
                245                 250                 255
Thr Leu Ile Asn Tyr Arg Met Asn Trp Val Arg Gln Ala Pro Gly Lys
                260                 265                 270
Gly Leu Glu Trp Val Ser Ser Ile Ser Ser Ser Ser Tyr Ile His
            275                 280                 285
Tyr Ala Asp Ser Val Lys Gly Arg Phe Thr Ile Ser Arg Asp Asn Ala
        290                 295                 300
Glu Asn Ser Leu Tyr Leu Gln Met Asn Ser Leu Arg Ala Glu Asp Thr
305                 310                 315                 320
Ala Val Tyr Tyr Cys Val Arg Glu Gly Pro Arg Ala Thr Gly Tyr Ser
                325                 330                 335
Met Ala Asp Val Phe Asp Ile Trp Gly Gln Gly Thr Met Val Thr Val
                340                 345                 350
Ser Ser Gly Gly Gly Gly Ser Gly Gly Gly Ser Gly Gly Gly Gly
            355                 360                 365
Ser Glu Leu Val Met Thr Gln Ser Pro Asp Ser Leu Ala Val Ser Leu
        370                 375                 380
Gly Glu Arg Ala Thr Ile Asn Cys Lys Ser Ser Gln Ser Val Leu Tyr
385                 390                 395                 400
Ser Ser Asn Asn Lys Ser Tyr Leu Ala Trp Tyr Gln Gln Lys Pro Gly
                405                 410                 415
Gln Pro Pro Lys Leu Leu Ile Tyr Trp Ala Ser Thr Arg Glu Ser Gly
                420                 425                 430
```

```
Val Pro Asp Arg Phe Ser Gly Ser Gly Ser Gly Thr Asp Phe Thr Leu
        435                 440                 445

Thr Ile Ser Ser Leu Gln Ala Glu Asp Val Ala Val Tyr Tyr Cys Gln
    450                 455                 460

Gln Tyr Tyr Ser Ala Pro Leu Thr Phe Gly Gly Gly Thr Lys Val Glu
465                 470                 475                 480

Ile Lys

<210> SEQ ID NO 13
<211> LENGTH: 710
<212> TYPE: PRT
<213> ORGANISM: Artificial Sequence
<220> FEATURE:
<223> OTHER INFORMATION: 548-scFv-KZ52-HCN (heavy chain N-terminal
      fusion) (human-mouse hybrid sequence)

<400> SEQUENCE: 13

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ile Asn Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Tyr Ile His Tyr Ala Asp Ser Val
50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Gly Pro Arg Ala Thr Gly Tyr Ser Met Ala Asp Val Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Glu Leu Val Met
    130                 135                 140

Thr Gln Ser Pro Asp Ser Leu Ala Val Ser Leu Gly Glu Arg Ala Thr
145                 150                 155                 160

Ile Asn Cys Lys Ser Ser Gln Ser Val Leu Tyr Ser Ser Asn Asn Lys
                165                 170                 175

Ser Tyr Leu Ala Trp Tyr Gln Gln Lys Pro Gly Gln Pro Pro Lys Leu
            180                 185                 190

Leu Ile Tyr Trp Ala Ser Thr Arg Glu Ser Gly Val Pro Asp Arg Phe
        195                 200                 205

Ser Gly Ser Gly Ser Gly Thr Asp Phe Thr Leu Thr Ile Ser Ser Leu
    210                 215                 220

Gln Ala Glu Asp Val Ala Val Tyr Tyr Cys Gln Gln Tyr Tyr Ser Ala
225                 230                 235                 240

Pro Leu Thr Phe Gly Gly Gly Thr Lys Val Glu Ile Lys Gly Gly Ser
                245                 250                 255

Ala Gly Ser Ala Gly Ser Ala Gly Ser Gly Ser Glu Val Gln Leu
            260                 265                 270

Gln Gln Ser Gly Ala Glu Leu Val Lys Pro Gly Ala Ser Val Lys Leu
        275                 280                 285

Ser Cys Thr Ala Ser Gly Phe Asn Ile Lys Asp Thr Tyr Met His Trp
    290                 295                 300
```

```
Val Lys Gln Arg Pro Glu Glu Gly Leu Glu Trp Ile Gly Arg Ile Asp
305                 310                 315                 320

Pro Ala Asp Gly Asn Thr Glu Tyr Val Pro Lys Phe Gln Gly Lys Ala
                325                 330                 335

Thr Ile Thr Ala Asp Thr Phe Ser Asn Thr Val Tyr Leu Gln Leu Ser
                340                 345                 350

Gly Leu Thr Ser Glu Asp Thr Ala Val Tyr Tyr Cys Ser Arg Gly Tyr
            355                 360                 365

Tyr Trp Gly Gln Gly Thr Thr Leu Thr Val Ser Ser Ala Ser Thr Lys
        370                 375                 380

Gly Pro Ser Val Phe Pro Leu Ala Pro Ser Ser Lys Ser Thr Ser Gly
385                 390                 395                 400

Gly Thr Ala Ala Leu Gly Cys Leu Val Lys Asp Tyr Phe Pro Glu Pro
                405                 410                 415

Val Thr Val Ser Trp Asn Ser Gly Ala Leu Thr Ser Gly Val His Thr
                420                 425                 430

Phe Pro Ala Val Leu Gln Ser Ser Gly Leu Tyr Ser Leu Ser Ser Val
            435                 440                 445

Val Thr Val Pro Ser Ser Leu Gly Thr Gln Thr Tyr Ile Cys Asn
        450                 455                 460

Val Asn His Lys Pro Ser Asn Thr Lys Val Asp Lys Lys Val Glu Pro
465                 470                 475                 480

Lys Ser Cys Asp Lys Thr His Thr Cys Pro Pro Cys Pro Ala Pro Glu
                485                 490                 495

Leu Leu Gly Arg Pro Ser Val Phe Leu Phe Pro Pro Lys Pro Lys Asp
            500                 505                 510

Thr Leu Met Ile Ser Arg Thr Pro Glu Val Thr Cys Val Val Val Asp
        515                 520                 525

Val Ser His Glu Asp Pro Glu Val Lys Phe Asn Trp Tyr Val Asp Gly
    530                 535                 540

Val Glu Val His Asn Ala Lys Thr Lys Pro Arg Glu Glu Gln Tyr Asn
545                 550                 555                 560

Ser Thr Tyr Arg Val Val Ser Val Leu Thr Val Leu His Gln Asp Trp
                565                 570                 575

Leu Asn Gly Lys Glu Tyr Lys Cys Lys Val Ser Asn Lys Ala Leu Pro
            580                 585                 590

Ala Pro Ile Glu Lys Thr Ile Ser Lys Ala Lys Gly Gln Pro Arg Glu
        595                 600                 605

Pro Gln Val Tyr Thr Leu Pro Pro Ser Arg Glu Glu Met Thr Lys Asn
    610                 615                 620

Gln Val Ser Leu Thr Cys Leu Val Lys Gly Phe Tyr Pro Ser Asp Ile
625                 630                 635                 640

Ala Val Glu Trp Glu Ser Asn Gly Gln Pro Glu Asn Asn Tyr Lys Thr
                645                 650                 655

Thr Pro Pro Val Leu Asp Ser Asp Gly Ser Phe Phe Leu Tyr Ser Lys
            660                 665                 670

Leu Thr Val Asp Lys Ser Arg Trp Gln Gln Gly Asn Val Phe Ser Cys
        675                 680                 685

Ser Val Met His Glu Ala Leu His Asn His Tyr Thr Gln Lys Ser Leu
    690                 695                 700

Ser Leu Ser Pro Gly Lys
705                 710
```

<210> SEQ ID NO 14
<211> LENGTH: 482
<212> TYPE: PRT
<213> ORGANISM: Artificial Sequence
<220> FEATURE:
<223> OTHER INFORMATION: 548-scFv-KZ52-LCN (light chain N-terminal fusion) (human-mouse hybrid sequence)

<400> SEQUENCE: 14

```
Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ile Asn Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Tyr Ile His Tyr Ala Asp Ser Val
    50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Gly Pro Arg Ala Thr Gly Tyr Ser Met Ala Asp Val Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Glu Leu Val Met
    130                 135                 140

Thr Gln Ser Pro Asp Ser Leu Ala Val Ser Leu Gly Glu Arg Ala Thr
145                 150                 155                 160

Ile Asn Cys Lys Ser Ser Gln Ser Val Leu Tyr Ser Ser Asn Asn Lys
                165                 170                 175

Ser Tyr Leu Ala Trp Tyr Gln Gln Lys Pro Gly Gln Pro Pro Lys Leu
            180                 185                 190

Leu Ile Tyr Trp Ala Ser Thr Arg Glu Ser Gly Val Pro Asp Arg Phe
        195                 200                 205

Ser Gly Ser Gly Ser Gly Thr Asp Phe Thr Leu Thr Ile Ser Ser Leu
    210                 215                 220

Gln Ala Glu Asp Val Ala Val Tyr Tyr Cys Gln Gln Tyr Tyr Ser Ala
225                 230                 235                 240

Pro Leu Thr Phe Gly Gly Gly Thr Lys Val Glu Ile Lys Gly Gly Ser
                245                 250                 255

Ala Gly Ser Ala Gly Ser Ala Gly Ser Gly Gly Ser Asp Ile Gln Met
            260                 265                 270

Thr Gln Ser Pro Ala Ser Leu Ser Ala Ser Val Gly Glu Thr Val Thr
        275                 280                 285

Ile Thr Cys Arg Ala Ser Glu Asn Ile Tyr Ser Tyr Leu Ala Trp Tyr
    290                 295                 300

Gln Gln Lys Gln Gly Lys Ser Pro Gln Leu Leu Val Tyr Asn Ala Lys
305                 310                 315                 320

Thr Leu Ala Glu Gly Val Pro Ser Arg Phe Ser Gly Ser Gly Ser Gly
                325                 330                 335

Thr Gln Phe Ser Leu Lys Ile Asn Ser Leu Gln Pro Glu Asp Phe Gly
            340                 345                 350

Ile Tyr Tyr Cys Gln His His Tyr Gly Ser Pro Trp Ala Phe Gly Gly
        355                 360                 365
```

-continued

Gly Thr Lys Leu Glu Ile Lys Arg Thr Val Ala Ala Pro Ser Val Phe
    370                 375                 380

Ile Phe Pro Pro Ser Asp Glu Gln Leu Lys Ser Gly Thr Ala Ser Val
385                 390                 395                 400

Val Cys Leu Leu Asn Asn Phe Tyr Pro Arg Glu Ala Lys Val Gln Trp
                405                 410                 415

Lys Val Asp Asn Ala Leu Gln Ser Gly Asn Ser Gln Glu Ser Val Thr
            420                 425                 430

Glu Gln Asp Ser Lys Asp Ser Thr Tyr Ser Leu Ser Ser Thr Leu Thr
        435                 440                 445

Leu Ser Lys Ala Asp Tyr Glu Lys His Lys Val Tyr Ala Cys Glu Val
    450                 455                 460

Thr His Gln Gly Leu Ser Ser Pro Val Thr Lys Ser Phe Asn Arg Gly
465                 470                 475                 480

Glu Cys

<210> SEQ ID NO 15
<211> LENGTH: 710
<212> TYPE: PRT
<213> ORGANISM: Artificial Sequence
<220> FEATURE:
<223> OTHER INFORMATION: 548-scFv-KZ52-HCC (heavy chain C-terminal
      fusion) (human-mouse hybrid sequence)

<400> SEQUENCE: 15

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asp Gly Asn Thr Glu Tyr Val Pro Lys Phe
    50                  55                  60

Gln Gly Lys Ala Thr Ile Thr Ala Asp Thr Phe Ser Asn Thr Val Tyr
65                  70                  75                  80

Leu Gln Leu Ser Gly Leu Thr Ser Glu Asp Thr Ala Val Tyr Tyr Cys
                85                  90                  95

Ser Arg Gly Tyr Tyr Trp Gly Gln Gly Thr Thr Leu Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Arg Pro Ser Val Phe Leu Phe Pro Pro
225                 230                 235                 240

```
Lys Pro Lys Asp Thr Leu Met Ile Ser Arg Thr Pro Glu Val Thr Cys
                245                 250                 255
Val Val Val Asp Val Ser His Glu Asp Pro Glu Val Lys Phe Asn Trp
            260                 265                 270
Tyr Val Asp Gly Val Glu Val His Asn Ala Lys Thr Lys Pro Arg Glu
        275                 280                 285
Glu Gln Tyr Asn Ser Thr Tyr Arg Val Val Ser Val Leu Thr Val Leu
    290                 295                 300
His Gln Asp Trp Leu Asn Gly Lys Glu Tyr Lys Cys Lys Val Ser Asn
305                 310                 315                 320
Lys Ala Leu Pro Ala Pro Ile Glu Lys Thr Ile Ser Lys Ala Lys Gly
                325                 330                 335
Gln Pro Arg Glu Pro Gln Val Tyr Thr Leu Pro Pro Ser Arg Glu Glu
            340                 345                 350
Met Thr Lys Asn Gln Val Ser Leu Thr Cys Leu Val Lys Gly Phe Tyr
        355                 360                 365
Pro Ser Asp Ile Ala Val Glu Trp Glu Ser Asn Gly Gln Pro Glu Asn
    370                 375                 380
Asn Tyr Lys Thr Thr Pro Pro Val Leu Asp Ser Asp Gly Ser Phe Phe
385                 390                 395                 400
Leu Tyr Ser Lys Leu Thr Val Asp Lys Ser Arg Trp Gln Gln Gly Asn
                405                 410                 415
Val Phe Ser Cys Ser Val Met His Glu Ala Leu His Asn His Tyr Thr
            420                 425                 430
Gln Lys Ser Leu Ser Leu Ser Pro Gly Lys Gly Gly Ser Ala Gly Ser
        435                 440                 445
Ala Gly Ser Ala Gly Ser Gly Gly Ser Glu Val Gln Leu Leu Glu Ser
    450                 455                 460
Gly Gly Gly Leu Val Lys Pro Gly Gly Ser Leu Arg Leu Ser Cys Ala
465                 470                 475                 480
Ala Ser Gly Phe Thr Leu Ile Asn Tyr Arg Met Asn Trp Val Arg Gln
                485                 490                 495
Ala Pro Gly Lys Gly Leu Glu Trp Val Ser Ser Ile Ser Ser Ser Ser
            500                 505                 510
Ser Tyr Ile His Tyr Ala Asp Ser Val Lys Gly Arg Phe Thr Ile Ser
        515                 520                 525
Arg Asp Asn Ala Glu Asn Ser Leu Tyr Leu Gln Met Asn Ser Leu Arg
    530                 535                 540
Ala Glu Asp Thr Ala Val Tyr Tyr Cys Val Arg Glu Gly Pro Arg Ala
545                 550                 555                 560
Thr Gly Tyr Ser Met Ala Asp Val Phe Asp Ile Trp Gly Gln Gly Thr
                565                 570                 575
Met Val Thr Val Ser Ser Gly Gly Gly Gly Ser Gly Gly Gly Gly Ser
            580                 585                 590
Gly Gly Gly Gly Ser Glu Leu Val Met Thr Gln Ser Pro Asp Ser Leu
        595                 600                 605
Ala Val Ser Leu Gly Glu Arg Ala Thr Ile Asn Cys Lys Ser Ser Gln
    610                 615                 620
Ser Val Leu Tyr Ser Ser Asn Asn Lys Ser Tyr Leu Ala Trp Tyr Gln
625                 630                 635                 640
Gln Lys Pro Gly Gln Pro Pro Lys Leu Leu Ile Tyr Trp Ala Ser Thr
                645                 650                 655
```

```
Arg Glu Ser Gly Val Pro Asp Arg Phe Ser Gly Ser Gly Ser Gly Thr
                660                 665                 670

Asp Phe Thr Leu Thr Ile Ser Ser Leu Gln Ala Glu Asp Val Ala Val
            675                 680                 685

Tyr Tyr Cys Gln Gln Tyr Tyr Ser Ala Pro Leu Thr Phe Gly Gly Gly
        690                 695                 700

Thr Lys Val Glu Ile Lys
705             710

<210> SEQ ID NO 16
<211> LENGTH: 482
<212> TYPE: PRT
<213> ORGANISM: Artificial Sequence
<220> FEATURE:
<223> OTHER INFORMATION: 548-scFv-KZ52-LCC (light chain C-terminal
      fusion) (human-mouse hybrid sequence)

<400> SEQUENCE: 16

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ile Tyr Tyr Cys Gln His His Tyr Gly Ser Pro Trp
                85                  90                  95

Ala Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ser Ala Gly Ser Ala Gly Ser Ala
    210                 215                 220

Gly Ser Gly Gly Ser Glu Val Gln Leu Leu Glu Ser Gly Gly Gly Leu
225                 230                 235                 240

Val Lys Pro Gly Gly Ser Leu Arg Leu Ser Cys Ala Ala Ser Gly Phe
                245                 250                 255

Thr Leu Ile Asn Tyr Arg Met Asn Trp Val Arg Gln Ala Pro Gly Lys
            260                 265                 270

Gly Leu Glu Trp Val Ser Ser Ile Ser Ser Ser Ser Tyr Ile His
        275                 280                 285

Tyr Ala Asp Ser Val Lys Gly Arg Phe Thr Ile Ser Arg Asp Asn Ala
    290                 295                 300
```

Glu Asn Ser Leu Tyr Leu Gln Met Asn Ser Leu Arg Ala Glu Asp Thr
305                 310                 315                 320

Ala Val Tyr Tyr Cys Val Arg Glu Gly Pro Arg Ala Thr Gly Tyr Ser
                325                 330                 335

Met Ala Asp Val Phe Asp Ile Trp Gly Gln Gly Thr Met Val Thr Val
            340                 345                 350

Ser Ser Gly Gly Gly Gly Ser Gly Gly Gly Gly Ser Gly Gly Gly Gly
        355                 360                 365

Ser Glu Leu Val Met Thr Gln Ser Pro Asp Ser Leu Ala Val Ser Leu
    370                 375                 380

Gly Glu Arg Ala Thr Ile Asn Cys Lys Ser Ser Gln Ser Val Leu Tyr
385                 390                 395                 400

Ser Ser Asn Asn Lys Ser Tyr Leu Ala Trp Tyr Gln Gln Lys Pro Gly
                405                 410                 415

Gln Pro Pro Lys Leu Leu Ile Tyr Trp Ala Ser Thr Arg Glu Ser Gly
            420                 425                 430

Val Pro Asp Arg Phe Ser Gly Ser Gly Ser Gly Thr Asp Phe Thr Leu
        435                 440                 445

Thr Ile Ser Ser Leu Gln Ala Glu Asp Val Ala Val Tyr Tyr Cys Gln
    450                 455                 460

Gln Tyr Tyr Ser Ala Pro Leu Thr Phe Gly Gly Gly Thr Lys Val Glu
465                 470                 475                 480

Ile Lys

<210> SEQ ID NO 17
<211> LENGTH: 715
<212> TYPE: PRT
<213> ORGANISM: Artificial Sequence
<220> FEATURE:
<223> OTHER INFORMATION: 952-scFv-KZ52-HCN (heavy chain N-terminal
      fusion) (human-mouse hybrid sequence)
<220> FEATURE:
<221> NAME/KEY: misc_feature
<222> LOCATION: (283)..(283)
<223> OTHER INFORMATION: Xaa can be any naturally occurring amino acid

<400> SEQUENCE: 17

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ile Asn Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Tyr Ile His Tyr Ala Asp Ser Val
    50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
            85                  90                  95

Val Arg Glu Gly Pro Arg Ala Thr Gly Tyr Ser Met Ala Asp Val Phe
                100                 105                 110

Asp Ile Trp Gly Gln Gly Thr Met Val Thr Val Ser Ser Gly Gly Gly
            115                 120                 125

Gly Ser Gly Gly Gly Gly Ser Gly Gly Gly Gly Ser Glu Leu Val Met
        130                 135                 140

Thr Gln Ser Pro Asp Ser Leu Ala Val Ser Leu Gly Glu Arg Ala Thr

```
            145                 150                 155                 160
       Ile Asn Cys Lys Ser Ser Gln Ser Val Leu Tyr Ser Ser Asn Asn Lys
                       165                 170                 175

Ser Tyr Leu Ala Trp Tyr Gln Gln Lys Pro Gly Gln Pro Pro Lys Leu
                       180                 185                 190

Leu Ile Tyr Trp Ala Ser Thr Arg Glu Ser Gly Val Pro Asp Arg Phe
                   195                 200                 205

Ser Gly Ser Gly Ser Gly Thr Asp Phe Thr Leu Thr Ile Ser Ser Leu
                   210                 215                 220

Gln Ala Glu Asp Val Ala Val Tyr Tyr Cys Gln Gln Tyr Tyr Ser Ala
       225                 230                 235                 240

Pro Leu Thr Phe Gly Gly Gly Thr Lys Val Glu Ile Lys Gly Gly Ser
                           245                 250                 255

Ala Gly Ser Ala Gly Ser Ala Gly Gly Ser Asp Val Gln Leu
                       260                 265                 270

Gln Glu Ser Gly Pro Asp Leu Val Lys Pro Xaa Gln Ser Leu Ser Leu
                   275                 280                 285

Thr Cys Thr Val Thr Gly Tyr Ser Ile Thr Ser Gly Tyr Ser Trp His
                   290                 295                 300

Trp Ile Arg Gln Phe Pro Gly Asn Arg Leu Glu Trp Met Asp Tyr Ile
       305                 310                 315                 320

His Tyr Ser Gly Ser Ile Asn Tyr Asn Pro Ser Leu Lys Ser Arg Ile
                       325                 330                 335

Ser Ile Thr Arg Asp Thr Ser Lys Asn Gln Phe Phe Leu Gln Leu Asn
                       340                 345                 350

Ser Val Thr Thr Glu Asp Thr Ala Thr Tyr Tyr Cys Ala Arg Trp Gly
                   355                 360                 365

Ala Thr Gly Phe Asp Tyr Trp Gly Gln Gly Thr Thr Leu Thr Val Ser
                   370                 375                 380

Ser Ala Ser Thr Lys Gly Pro Ser Val Phe Pro Leu Ala Pro Ser Ser
       385                 390                 395                 400

Lys Ser Thr Ser Gly Gly Thr Ala Ala Leu Gly Cys Leu Val Lys Asp
                           405                 410                 415

Tyr Phe Pro Glu Pro Val Thr Val Ser Trp Asn Ser Gly Ala Leu Thr
                       420                 425                 430

Ser Gly Val His Thr Phe Pro Ala Val Leu Gln Ser Ser Gly Leu Tyr
                       435                 440                 445

Ser Leu Ser Ser Val Val Thr Val Pro Ser Ser Ser Leu Gly Thr Gln
                   450                 455                 460

Thr Tyr Ile Cys Asn Val Asn His Lys Pro Ser Asn Thr Lys Val Asp
       465                 470                 475                 480

Lys Lys Val Glu Pro Lys Ser Cys Asp Lys Thr His Thr Cys Pro Pro
                           485                 490                 495

Cys Pro Ala Pro Glu Leu Leu Gly Arg Pro Ser Val Phe Leu Phe Pro
                       500                 505                 510

Pro Lys Pro Lys Asp Thr Leu Met Ile Ser Arg Thr Pro Glu Val Thr
                   515                 520                 525

Cys Val Val Val Asp Val Ser His Glu Asp Pro Glu Val Lys Phe Asn
                   530                 535                 540

Trp Tyr Val Asp Gly Val Glu Val His Asn Ala Lys Thr Lys Pro Arg
       545                 550                 555                 560

Glu Glu Gln Tyr Asn Ser Thr Tyr Arg Val Val Ser Val Leu Thr Val
                           565                 570                 575
```

```
Leu His Gln Asp Trp Leu Asn Gly Lys Glu Tyr Lys Cys Lys Val Ser
            580                 585                 590

Asn Lys Ala Leu Pro Ala Pro Ile Glu Lys Thr Ile Ser Lys Ala Lys
        595                 600                 605

Gly Gln Pro Arg Glu Pro Gln Val Tyr Thr Leu Pro Pro Ser Arg Glu
    610                 615                 620

Glu Met Thr Lys Asn Gln Val Ser Leu Thr Cys Leu Val Lys Gly Phe
625                 630                 635                 640

Tyr Pro Ser Asp Ile Ala Val Glu Trp Glu Ser Asn Gly Gln Pro Glu
                645                 650                 655

Asn Asn Tyr Lys Thr Thr Pro Pro Val Leu Asp Ser Asp Gly Ser Phe
            660                 665                 670

Phe Leu Tyr Ser Lys Leu Thr Val Asp Lys Ser Arg Trp Gln Gln Gly
        675                 680                 685

Asn Val Phe Ser Cys Ser Val Met His Glu Ala Leu His Asn His Tyr
    690                 695                 700

Thr Gln Lys Ser Leu Ser Leu Ser Pro Gly Lys
705                 710                 715

<210> SEQ ID NO 18
<211> LENGTH: 482
<212> TYPE: PRT
<213> ORGANISM: Artificial Sequence
<220> FEATURE:
<223> OTHER INFORMATION: 952-scFv-KZ52-LCN (light chain N-terminal
      fusion) (human-mouse hybrid sequence)

<400> SEQUENCE: 18

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ile Asn Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Tyr Ile His Tyr Ala Asp Ser Val
    50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Gly Pro Arg Ala Thr Gly Tyr Ser Met Ala Asp Val Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Glu Leu Val Met
    130                 135                 140

Thr Gln Ser Pro Asp Ser Leu Ala Val Ser Leu Gly Glu Arg Ala Thr
145                 150                 155                 160

Ile Asn Cys Lys Ser Ser Gln Ser Val Leu Tyr Ser Ser Asn Asn Lys
                165                 170                 175

Ser Tyr Leu Ala Trp Tyr Gln Gln Lys Pro Gly Gln Pro Pro Lys Leu
            180                 185                 190

Leu Ile Tyr Trp Ala Ser Thr Arg Glu Ser Gly Val Pro Asp Arg Phe
        195                 200                 205

Ser Gly Ser Gly Ser Gly Thr Asp Phe Thr Leu Thr Ile Ser Ser Leu
```

```
              210                 215                 220
    Gln Ala Glu Asp Val Ala Val Tyr Tyr Cys Gln Gln Tyr Tyr Ser Ala
    225                 230                 235                 240

Pro Leu Thr Phe Gly Gly Gly Thr Lys Val Glu Ile Lys Gly Gly Ser
                    245                 250                 255

Ala Gly Ser Ala Gly Ser Ala Gly Ser Gly Gly Ser Asp Ile Val Met
                    260                 265                 270

Thr Gln Ser His Lys Phe Met Ser Thr Ser Val Gly Asp Arg Val Ser
                275                 280                 285

Ile Thr Cys Lys Ala Ser Gln Asp Val Asn Thr Ala Val Val Trp Tyr
    290                 295                 300

Gln Gln Lys Pro Gly Gln Ser Pro Lys Leu Leu Ile Tyr Trp Ala Ser
    305                 310                 315                 320

Thr Arg His Thr Gly Val Pro Asp Arg Phe Thr Gly Ser Gly Ser Gly
                    325                 330                 335

Thr Asp Phe Thr Leu Thr Ile Ser Ser Val Gln Ala Glu Asp Leu Ala
                    340                 345                 350

Leu Tyr Tyr Cys Gln Gln His Tyr Thr Ser Pro Trp Thr Phe Gly Gly
                355                 360                 365

Gly Thr Lys Leu Glu Ile Lys Arg Thr Val Ala Ala Pro Ser Val Phe
    370                 375                 380

Ile Phe Pro Pro Ser Asp Glu Gln Leu Lys Ser Gly Thr Ala Ser Val
    385                 390                 395                 400

Val Cys Leu Leu Asn Asn Phe Tyr Pro Arg Glu Ala Lys Val Gln Trp
                    405                 410                 415

Lys Val Asp Asn Ala Leu Gln Ser Gly Asn Ser Gln Glu Ser Val Thr
                    420                 425                 430

Glu Gln Asp Ser Lys Asp Ser Thr Tyr Ser Leu Ser Ser Thr Leu Thr
                435                 440                 445

Leu Ser Lys Ala Asp Tyr Glu Lys His Lys Val Tyr Ala Cys Glu Val
    450                 455                 460

Thr His Gln Gly Leu Ser Ser Pro Val Thr Lys Ser Phe Asn Arg Gly
    465                 470                 475                 480

Glu Cys

<210> SEQ ID NO 19
<211> LENGTH: 715
<212> TYPE: PRT
<213> ORGANISM: Artificial Sequence
<220> FEATURE:
<223> OTHER INFORMATION: 952-scFv-KZ52-HCC (heavy chain C-terminal
      fusion) (human-mouse hybrid sequence)
<220> FEATURE:
<221> NAME/KEY: misc_feature
<222> LOCATION: (15)..(15)
<223> OTHER INFORMATION: Xaa can be any naturally occurring amino acid

<400> SEQUENCE: 19

Asp Val Gln Leu Gln Glu Ser Gly Pro Asp Leu Val Lys Pro Xaa Gln
    1               5                   10                  15

Ser Leu Ser Leu Thr Cys Thr Val Thr Gly Tyr Ser Ile Thr Ser Gly
                    20                  25                  30

Tyr Ser Trp His Trp Ile Arg Gln Phe Pro Gly Asn Arg Leu Glu Trp
                35                  40                  45

Met Asp Tyr Ile His Tyr Ser Gly Ser Ile Asn Tyr Asn Pro Ser Leu
    50                  55                  60
```

-continued

```
Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Ala Arg Trp Gly Ala Thr Gly Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Arg Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Ser Ala Gly Ser Ala Gly Ser Ala Gly Ser Gly Gly Ser Glu Val
    450                 455                 460

Gln Leu Leu Glu Ser Gly Gly Gly Leu Val Lys Pro Gly Gly Ser Leu
465                 470                 475                 480

Arg Leu Ser Cys Ala Ala Ser Gly Phe Thr Leu Ile Asn Tyr Arg Met
```

```
            485                 490                 495
Asn Trp Val Arg Gln Ala Pro Gly Lys Gly Leu Glu Trp Val Ser Ser
                500                 505                 510

Ile Ser Ser Ser Ser Ser Tyr Ile His Tyr Ala Asp Ser Val Lys Gly
            515                 520                 525

Arg Phe Thr Ile Ser Arg Asp Asn Ala Glu Asn Ser Leu Tyr Leu Gln
            530                 535                 540

Met Asn Ser Leu Arg Ala Glu Asp Thr Ala Val Tyr Tyr Cys Val Arg
545                 550                 555                 560

Glu Gly Pro Arg Ala Thr Gly Tyr Ser Met Ala Asp Val Phe Asp Ile
                565                 570                 575

Trp Gly Gln Gly Thr Met Val Thr Val Ser Ser Gly Gly Gly Gly Ser
                580                 585                 590

Gly Gly Gly Gly Ser Gly Gly Gly Ser Glu Leu Val Met Thr Gln
            595                 600                 605

Ser Pro Asp Ser Leu Ala Val Ser Leu Gly Glu Arg Ala Thr Ile Asn
            610                 615                 620

Cys Lys Ser Ser Gln Ser Val Leu Tyr Ser Ser Asn Asn Lys Ser Tyr
625                 630                 635                 640

Leu Ala Trp Tyr Gln Gln Lys Pro Gly Gln Pro Pro Lys Leu Leu Ile
                645                 650                 655

Tyr Trp Ala Ser Thr Arg Glu Ser Gly Val Pro Asp Arg Phe Ser Gly
                660                 665                 670

Ser Gly Ser Gly Thr Asp Phe Thr Leu Thr Ile Ser Ser Leu Gln Ala
            675                 680                 685

Glu Asp Val Ala Val Tyr Tyr Cys Gln Gln Tyr Tyr Ser Ala Pro Leu
            690                 695                 700

Thr Phe Gly Gly Gly Thr Lys Val Glu Ile Lys
705                 710                 715

<210> SEQ ID NO 20
<211> LENGTH: 482
<212> TYPE: PRT
<213> ORGANISM: Artificial Sequence
<220> FEATURE:
<223> OTHER INFORMATION: 952-scFv-KZ52-LCC (light chain C-terminal
      fusion) (human-mouse hybrid sequence)

<400> SEQUENCE: 20

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Val Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Val Gln Ala
65                  70                  75                  80

Glu Asp Leu Ala Leu Tyr Tyr Cys Gln Gln His Tyr Thr Ser Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ser Ala Gly Ser Ala Gly Ser Ala
210                 215                 220

Gly Ser Gly Gly Ser Glu Val Gln Leu Leu Glu Ser Gly Gly Gly Leu
225                 230                 235                 240

Val Lys Pro Gly Gly Ser Leu Arg Leu Ser Cys Ala Ala Ser Gly Phe
                245                 250                 255

Thr Leu Ile Asn Tyr Arg Met Asn Trp Val Arg Gln Ala Pro Gly Lys
            260                 265                 270

Gly Leu Glu Trp Val Ser Ser Ile Ser Ser Ser Ser Tyr Ile His
        275                 280                 285

Tyr Ala Asp Ser Val Lys Gly Arg Phe Thr Ile Ser Arg Asp Asn Ala
290                 295                 300

Glu Asn Ser Leu Tyr Leu Gln Met Asn Ser Leu Arg Ala Glu Asp Thr
305                 310                 315                 320

Ala Val Tyr Tyr Cys Val Arg Glu Gly Pro Arg Ala Thr Gly Tyr Ser
                325                 330                 335

Met Ala Asp Val Phe Asp Ile Trp Gly Gln Gly Thr Met Val Thr Val
            340                 345                 350

Ser Ser Gly Gly Gly Ser Gly Gly Gly Ser Gly Gly Gly Gly
        355                 360                 365

Ser Glu Leu Val Met Thr Gln Ser Pro Asp Ser Leu Ala Val Ser Leu
370                 375                 380

Gly Glu Arg Ala Thr Ile Asn Cys Lys Ser Ser Gln Ser Val Leu Tyr
385                 390                 395                 400

Ser Ser Asn Asn Lys Ser Tyr Leu Ala Trp Tyr Gln Gln Lys Pro Gly
                405                 410                 415

Gln Pro Pro Lys Leu Leu Ile Tyr Trp Ala Ser Thr Arg Glu Ser Gly
            420                 425                 430

Val Pro Asp Arg Phe Ser Gly Ser Gly Thr Asp Phe Thr Leu
        435                 440                 445

Thr Ile Ser Ser Leu Gln Ala Glu Asp Val Ala Val Tyr Tyr Cys Gln
450                 455                 460

Gln Tyr Tyr Ser Ala Pro Leu Thr Phe Gly Gly Thr Lys Val Glu
465                 470                 475                 480

Ile Lys

<210> SEQ ID NO 21
<211> LENGTH: 589
<212> TYPE: PRT
<213> ORGANISM: Artificial Sequence
<220> FEATURE:
<223> OTHER INFORMATION: 401-NPC2-HCC (NPC2 C-terminal fusion to heavy
      chain of 401 IgG1) (human-mouse hybrid sequence)

<400> SEQUENCE: 21
```

```
Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Glu Tyr Asp Thr Lys Phe
 50                  55                  60

Gln Gly Lys Ala Thr Ile Thr Ala Asp Thr Ser Asn Thr Ala Tyr
 65                  70                  75                  80

Leu Gln Leu Ser Ser Leu Thr Ser Glu Asp Thr Ala Val Tyr Tyr Cys
                85                  90                  95

Ser Arg Gly Tyr Tyr Trp Gly Arg Gly Thr Thr Leu Thr Val Ser Ser
            100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
            130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
            165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
            195                 200                 205

Lys Val Glu Pro Lys Ser Cys Asp Lys Thr His Thr Cys Pro Pro Cys
            210                 215                 220

Pro Ala Pro Glu Leu Leu Gly Arg Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
            275                 280                 285

Glu Gln Tyr Asn Ser Thr Tyr Arg Val Val Ser Val Leu Thr Val Leu
            290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
            325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
```

```
                420              425                430
Gln Lys Ser Leu Ser Leu Ser Pro Gly Lys Gly Gly Ser Ala Gly Ser
            435                 440             445

Ala Gly Ser Ala Gly Ser Gly Gly Ser Glu Pro Val Gln Phe Lys Asp
    450             455                 460

Cys Gly Ser Val Asp Gly Val Ile Lys Glu Val Asn Val Ser Pro Cys
465             470              475                 480

Pro Thr Gln Pro Cys Gln Leu Ser Lys Gly Gln Ser Tyr Ser Val Asn
                485             490                 495

Val Thr Phe Thr Ser Asn Ile Gln Ser Lys Ser Lys Ala Val Val
            500             505             510

His Gly Ile Leu Met Gly Val Pro Val Pro Phe Pro Ile Pro Glu Pro
            515             520             525

Asp Gly Cys Lys Ser Gly Ile Asn Cys Pro Ile Gln Lys Asp Lys Thr
            530             535             540

Tyr Ser Tyr Leu Asn Lys Leu Pro Val Lys Ser Glu Tyr Pro Ser Ile
545             550             555                 560

Lys Leu Val Val Glu Trp Gln Leu Gln Asp Asp Lys Asn Gln Ser Leu
                565             570             575

Phe Cys Trp Glu Ile Pro Val Gln Ile Val Ser His Leu
            580             585
```

<210> SEQ ID NO 22
<211> LENGTH: 589
<212> TYPE: PRT
<213> ORGANISM: Artificial Sequence
<220> FEATURE:
<223> OTHER INFORMATION: 548-NPC2-HCC (NPC2 C-terminal fusion to heavy
      chain of 548 IgG1) (human-mouse hybrid sequence)

<400> SEQUENCE: 22

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Glu Gly Leu Glu Trp Ile
        35                  40                  45

Gly Arg Ile Asp Pro Ala Asp Gly Asn Thr Glu Tyr Val Pro Lys Phe
    50                  55                  60

Gln Gly Lys Ala Thr Ile Thr Ala Asp Thr Phe Ser Asn Thr Val Tyr
65                  70                  75                  80

Leu Gln Leu Ser Gly Leu Thr Ser Glu Asp Thr Ala Val Tyr Tyr Cys
                85                  90                  95

Ser Arg Gly Tyr Tyr Trp Gly Gln Gly Thr Thr Leu Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190
```

```
Tyr Ile Cys Asn Val Asn His Lys Pro Ser Asn Thr Lys Val Asp Lys
            195                 200                 205

Lys Val Glu Pro Lys Ser Cys Asp Lys Thr His Thr Cys Pro Pro Cys
210                 215                 220

Pro Ala Pro Glu Leu Leu Gly Arg Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
            275                 280                 285

Glu Gln Tyr Asn Ser Thr Tyr Arg Val Val Ser Val Leu Thr Val Leu
        290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
                340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430

Gln Lys Ser Leu Ser Leu Ser Pro Gly Lys Gly Gly Ser Ala Gly Ser
            435                 440                 445

Ala Gly Ser Ala Gly Ser Gly Gly Ser Glu Pro Val Gln Phe Lys Asp
450                 455                 460

Cys Gly Ser Val Asp Gly Val Ile Lys Glu Val Asn Val Ser Pro Cys
465                 470                 475                 480

Pro Thr Gln Pro Cys Gln Leu Ser Lys Gly Gln Ser Tyr Ser Val Asn
                485                 490                 495

Val Thr Phe Thr Ser Asn Ile Gln Ser Lys Ser Ser Lys Ala Val Val
            500                 505                 510

His Gly Ile Leu Met Gly Val Pro Val Pro Phe Pro Ile Pro Glu Pro
            515                 520                 525

Asp Gly Cys Lys Ser Gly Ile Asn Cys Pro Ile Gln Lys Asp Lys Thr
530                 535                 540

Tyr Ser Tyr Leu Asn Lys Leu Pro Val Lys Ser Glu Tyr Pro Ser Ile
545                 550                 555                 560

Lys Leu Val Val Glu Trp Gln Leu Gln Asp Asp Lys Asn Gln Ser Leu
                565                 570                 575

Phe Cys Trp Glu Ile Pro Val Gln Ile Val Ser His Leu
            580                 585

<210> SEQ ID NO 23
<211> LENGTH: 10
<212> TYPE: PRT
```

```
<213> ORGANISM: Homo sapiens

<400> SEQUENCE: 23

Asp Phe Phe Val Tyr Ala Asp Tyr His Thr
1               5                   10

<210> SEQ ID NO 24
<211> LENGTH: 30
<212> TYPE: PRT
<213> ORGANISM: Homo sapiens

<400> SEQUENCE: 24

Leu Asn Tyr Phe Gln Asn Ser His Ser Val Leu Asp His Lys Lys Gly
1               5                   10                  15

Asp Asp Phe Phe Val Tyr Ala Asp Tyr His Thr His Phe Leu
            20                  25                  30

<210> SEQ ID NO 25
<211> LENGTH: 30
<212> TYPE: PRT
<213> ORGANISM: Macaca mulatta

<400> SEQUENCE: 25

Leu Asn Tyr Phe Gln Asn Ser His Ser Val Leu Asp His Lys Lys Gly
1               5                   10                  15

Asp Asp Phe Phe Val Tyr Ala Asp Tyr His Thr His Phe Leu
            20                  25                  30

<210> SEQ ID NO 26
<211> LENGTH: 30
<212> TYPE: PRT
<213> ORGANISM: Colobus guereza

<400> SEQUENCE: 26

Leu Asn Tyr Phe Gln Asn Ser His Ser Val Leu Asp His Lys Lys Gly
1               5                   10                  15

Asp Asp Phe Phe Val Tyr Ala Asp Tyr His Thr His Phe Leu
            20                  25                  30

<210> SEQ ID NO 27
<211> LENGTH: 30
<212> TYPE: PRT
<213> ORGANISM: Macaca fascicularis

<400> SEQUENCE: 27

Leu Asn Tyr Phe Gln Asn Ser His Ser Val Leu Asp His Lys Lys Gly
1               5                   10                  15

Asp Asp Phe Phe Val Tyr Ala Asp Tyr His Thr His Phe Leu
            20                  25                  30
```